US012787641B2

(12) United States Patent
Oh et al.

(10) Patent No.: US 12,787,641 B2
(45) Date of Patent: Nov. 3, 2026

(54) COMPOUND AND COMPOSITION FOR ORGANIC OPTOELECTRONIC DEVICE, ORGANIC OPTOELECTRONIC DEVICE, AND DISPLAY DEVICE

(71) Applicant: SAMSUNG SDI CO., LTD., Yongin-si (KR)

(72) Inventors: Jae-Jin Oh, Suwon-si (KR); Gi-Wook Kang, Suwon-si (KR); Eui-Su Kang, Suwon-si (KR); Youn-Hwan Kim, Suwon-si (KR); Hun Kim, Suwon-si (KR); Yong-Tak Yang, Suwon-si (KR); Eun-Sun Yu, Suwon-si (KR); Nam-Heon Lee, Suwon-si (KR); Han-Ill Lee, Suwon-si (KR); Pyeong-Seok Cho, Suwon-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 0 days.

(21) Appl. No.: 18/760,566

(22) Filed: Jul. 1, 2024

(65) Prior Publication Data

US 2024/0352627 A1 Oct. 24, 2024

Related U.S. Application Data

(63) Continuation of application No. 14/902,225, filed as application No. PCT/KR2013/008790 on Oct. 1, 2013, now abandoned.

(30) Foreign Application Priority Data

Sep. 6, 2013 (KR) ........................ 10-2013-0107391

(51) Int. Cl.
*H10K 85/60* (2023.01)
*B65H 51/015* (2006.01)
(Continued)

(52) U.S. Cl.
CPC ......... *H10K 85/654* (2023.02); *B65H 51/015* (2013.01); *B65H 54/2896* (2013.01);
(Continued)

(58) Field of Classification Search
CPC .. C07D 209/86; C07D 251/24; C07D 401/04; C07D 401/14; C07D 405/04;
(Continued)

(56) References Cited

U.S. PATENT DOCUMENTS

| | | | | |
|---|---|---|---|---|
| 8,367,850 B2 | 2/2013 | Ma et al. | | |
| 2002/0076576 A1* | 6/2002 | Li | ........................ | H10K 85/342 428/917 |

(Continued)

FOREIGN PATENT DOCUMENTS

| | | |
|---|---|---|
| CN | 102532105 A | 7/2012 |
| CN | 102597158 A | 7/2012 |

(Continued)

OTHER PUBLICATIONS

WO-2011081423-A1 machine translation (Year: 2011).*

(Continued)

*Primary Examiner* — Elizabeth M. Dahlburg
(74) *Attorney, Agent, or Firm* — Lee IP Law, P.C.

(57) ABSTRACT

Disclosed is a composition for an organic optoelectronic device including at least one kind of a first host compound and at least one kind of a second host compound represented by Chemical Formula 2-I and an organic optoelectronic device and a display device including the composition.

6 Claims, 1 Drawing Sheet

(51) Int. Cl.

| | |
|---|---|
| ***B65H 54/28*** | (2006.01) |
| ***C07D 209/86*** | (2006.01) |
| ***C07D 251/24*** | (2006.01) |
| ***C07D 401/04*** | (2006.01) |
| ***C07D 401/14*** | (2006.01) |
| ***C07D 405/04*** | (2006.01) |
| ***C07D 405/14*** | (2006.01) |
| ***C07D 409/04*** | (2006.01) |
| ***C07D 409/14*** | (2006.01) |
| ***C09K 11/06*** | (2006.01) |
| ***D01F 9/127*** | (2006.01) |
| ***D01G 99/00*** | (2010.01) |
| ***D01H 1/04*** | (2006.01) |
| ***D01H 1/14*** | (2006.01) |
| ***D01H 5/72*** | (2006.01) |
| ***D01H 13/04*** | (2006.01) |
| ***D02G 3/16*** | (2006.01) |
| ***H10K 50/11*** | (2023.01) |
| *H10K 101/00* | (2023.01) |
| *H10K 101/10* | (2023.01) |

(52) U.S. Cl.

CPC ......... *C07D 209/86* (2013.01); *C07D 251/24* (2013.01); *C07D 401/04* (2013.01); *C07D 401/14* (2013.01); *C07D 405/04* (2013.01); *C07D 405/14* (2013.01); *C07D 409/04* (2013.01); *C07D 409/14* (2013.01); *C09K 11/06* (2013.01); *D01F 9/127* (2013.01); *D01G 99/00* (2013.01); *D01H 1/04* (2013.01); *D01H 1/14* (2013.01); *D01H 5/72* (2013.01); *D01H 13/04* (2013.01); *D02G 3/16* (2013.01); *H10K 85/622* (2023.02); *H10K 85/6572* (2023.02); *B65H 2701/314* (2013.01); *C09K 2211/1007* (2013.01); *C09K 2211/1011* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *C09K 2211/185* (2013.01); *D10B 2101/122* (2013.01); *H10K 50/11* (2023.02); *H10K 2101/10* (2023.02); *H10K 2101/90* (2023.02)

(58) Field of Classification Search

CPC .. C07D 405/14; C07D 409/04; C07D 409/14; H10K 50/11; H10K 85/622; H10K 85/654; H10K 85/6572; H10K 2101/10; H10K 2101/90; C09K 11/06; C09K 2211/1007; C09K 2211/1011; C09K 2211/1029; C09K 2211/1044; C09K 2211/1059; C09K 2211/1088; C09K 2211/1092

See application file for complete search history.

(56) References Cited

U.S. PATENT DOCUMENTS

| | | | |
|---|---|---|---|
| 2006/0103298 | A1 | 5/2006 | Lee |
| 2012/0181518 | A1 | 7/2012 | Ogiwara et al. |
| 2012/0211736 | A1 | 8/2012 | Kim et al. |
| 2012/0223295 | A1 | 9/2012 | Inoue et al. |
| 2012/0273764 | A1 | 11/2012 | Yu et al. |
| 2012/0273794 | A1 | 11/2012 | Saito et al. |
| 2013/0048964 | A1 | 2/2013 | Takeda et al. |
| 2013/0221332 | A1 | 8/2013 | Xia et al. |
| 2014/0284584 | A1 | 9/2014 | Zheng |
| 2014/0367645 | A1 | 12/2014 | Seo |
| 2014/0367654 | A1 | 12/2014 | Kim et al. |
| 2015/0001489 | A1 | 1/2015 | Lee |
| 2015/0214489 | A1 | 7/2015 | Parham et al. |

FOREIGN PATENT DOCUMENTS

| | | | |
|---|---|---|---|
| CN | 102869659 | A | 1/2013 |
| JP | 3139321 | B2 | 2/2001 |
| JP | 2005-276801 | A | 10/2005 |
| JP | 4388590 | B2 | 12/2009 |
| JP | 2012-059904 | A | 3/2012 |
| JP | 2012-080093 | A | 4/2012 |
| JP | 2012-216819 | A | 11/2012 |
| KR | 10-2005-0123409 | A | 12/2005 |
| KR | 10-2006-0055767 | A | 5/2006 |
| KR | 10-2006-0097313 | A | 9/2006 |
| KR | 10-2009-0050485 | A | 6/2009 |
| KR | 10-2010-0063713 | A | 6/2010 |
| KR | 10-2011-0041729 | A | 4/2011 |
| KR | 10-2011-0048840 | A | 5/2011 |
| KR | 10-2011-0077909 | A | 7/2011 |
| KR | 10-2011-0122051 | A | 11/2011 |
| KR | 10-2011-0130904 | A | 12/2011 |
| KR | 10-2012-0012431 | A | 2/2012 |
| KR | 10-2012-0034648 | A | 4/2012 |
| KR | 10-2012-0046778 | A | 5/2012 |
| KR | 10-1183722 | B1 | 9/2012 |
| KR | 10-2012-0116282 | A | 10/2012 |
| KR | 10-2012-0130074 | A | 11/2012 |
| KR | 10-2012-0130102 | A | 11/2012 |
| KR | 10-2012-0140140 | A | 12/2012 |
| KR | 10-1212670 | B1 | 12/2012 |
| KR | 10-2013-0020398 | A | 2/2013 |
| KR | 10-1247626 | B1 | 3/2013 |
| KR | 10-2013-0060157 | A | 6/2013 |
| KR | 10-1288567 | B1 | 7/2013 |
| KR | 10-1433822 | | 8/2014 |
| KR | 10-2014-0135524 | A | 11/2014 |
| KR | 10-2015-0003599 | A | 1/2015 |
| WO | WO 2009-136596 | A1 | 11/2009 |
| WO | WO 2010-098246 | A1 | 9/2010 |
| WO | WO 2011-055933 | A2 | 5/2011 |
| WO | WO 2011-081423 | A2 | 7/2011 |
| WO | WO 2011-137072 | A1 | 11/2011 |
| WO | WO 2011-149240 | A2 | 12/2011 |
| WO | WO 2011/162162 | A1 | 12/2011 |
| WO | WO 2012-023947 | A1 | 2/2012 |
| WO | WO 2012/033061 | A1 | 3/2012 |
| WO | WO 2012/133652 | A1 | 4/2012 |
| WO | WO 2012-108388 | A1 | 8/2012 |
| WO | WO 2013-085243 | A1 | 6/2013 |
| WO | WO 2013/112557 | A1 | 8/2013 |

OTHER PUBLICATIONS

Sasabe, et al., "3,3'-Bicarbazole-Based Host Materials for High-Efficiency Blue Phosphorescent OLEDs with Extremely Low Driving Voltage," Adv. Mater. 2012, 24, 3212-3217 (2012).

Chinese Search Report dated Sep. 29, 2016 in Corresponding Chinese Patent Application No. 201380078272.7.

Extended European Search Report dated Mar. 14, 2017, of the corresponding European Patent Application No. 13893165.4.

Chinese Registration Certificate mailed Sep. 26, 2017.

* cited by examiner

【FIG. 1】
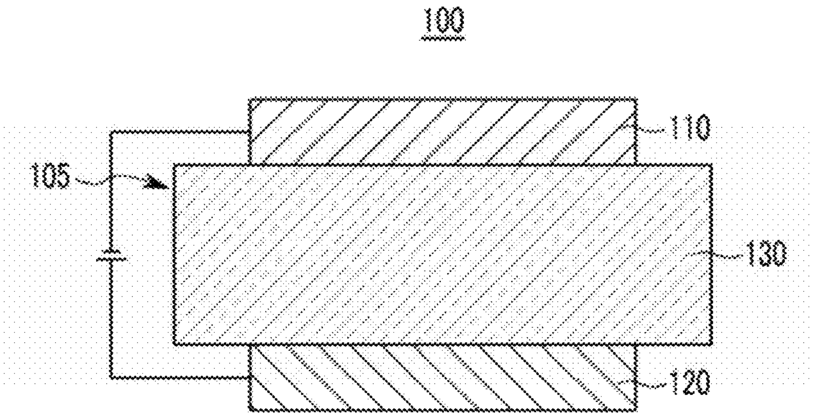
【FIG. 2】
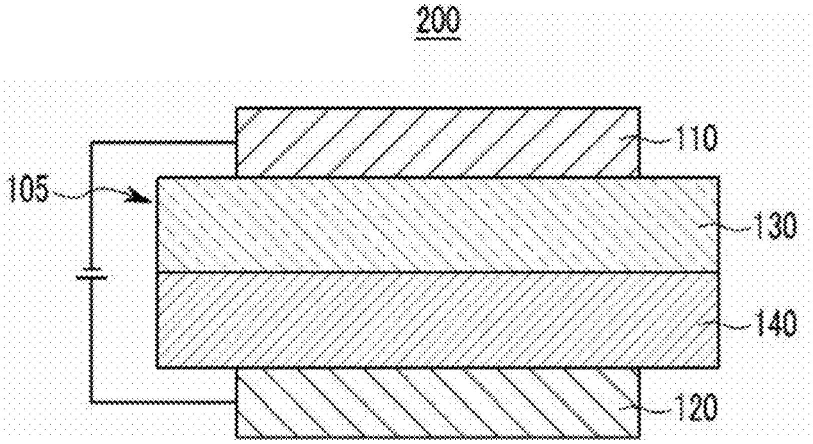

COMPOUND AND COMPOSITION FOR ORGANIC OPTOELECTRONIC DEVICE, ORGANIC OPTOELECTRONIC DEVICE, AND DISPLAY DEVICE

CROSS REFERENCE TO RELATED APPLICATIONS

This is a continuation application based on pending application Ser. No. 14/902,225, filed Dec. 30, 2015, the entire contents of which is hereby incorporated by reference.

Application Ser. No. 14/902,225 is the U.S. national phase application based on PCT Application No. PCT/KR2013/008790, filed Oct. 1, 2013, which is based on Korean Patent Application No. 10-2013-0107391, filed Sep. 6, 2013, the entire contents of all of which are hereby incorporated by reference.

TECHNICAL FIELD

A composition for an organic optoelectric device, an organic optoelectric device and a display device using the same are disclosed.

BACKGROUND ART

An organic optoelectric device is a device that converts electrical energy into photoenergy, and vice versa.

An organic optoelectric device may be classified as follows in accordance with its driving principles. One is an electronic device where excitons generated by photoenergy are separated into electrons and holes and the electrons and holes are transferred to different electrodes respectively and electrical energy is generated, and the other is a light emitting device to generate photoenergy from electrical energy by supplying a voltage or a current to electrodes.

Examples of the organic optoelectric device include an organic photoelectric device, an organic light emitting diode, an organic solar cell, and an organic photo-conductor drum, and the like.

Among them, the organic light emitting diode (OLED) has recently drawn attention due to an increase in demand for flat panel displays. The organic light emitting diode converts electrical energy into light by applying current to an organic light emitting material, and has a structure in which an organic layer is interposed between an anode and a cathode. Herein, the organic layer may include an emission layer, and optionally an auxiliary layer, and the auxiliary layer may include at least one layer selected from, for example a hole injection layer, a hole transport layer, an electron blocking layer, an electron transport layer, an electron injection layer, and a hole blocking layer in order to improve efficiency and stability of an organic light emitting diode.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

DISCLOSURE

Technical Object

One embodiment provides a composition for an organic optoelectric device capable of realizing an organic optoelectric device having high efficiency, a long life-span, and the like.

Another embodiment provides an organic optoelectric device including the composition.

Yet another embodiment provides a display device including the organic optoelectric device.

Technical Solving Method

According to one embodiment, a composition for an organic optoelectric device including at least one of a first host compound represented by the following Chemical Formula 1 and at least one kind of a second host compound represented by the following Chemical Formula 2 is provided.

[Chemical Formula 1]

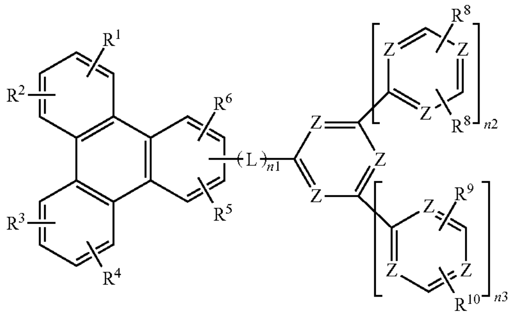

In the above Chemical Formula 1,

Z is independently N or $CR^a$, at least one of Z is N, $R^1$ to $R^{10}$ and $R^a$ are independently hydrogen, deuterium, a substituted or unsubstituted C1 to C10 alkyl group, a substituted or unsubstituted C6 to C12 aryl group, or a combination thereof, in the above Chemical Formula 1, the total number of 6-membered rings substituting the triphenylene group is less than or equal to 6, L is a substituted or unsubstituted phenylene group, a substituted or unsubstituted biphenylene group or a substituted or unsubstituted terphenylene group, n1 to n3 are independently 0 or 1, and $n1+n2+n3>1$.

[Chemical Formula 2]

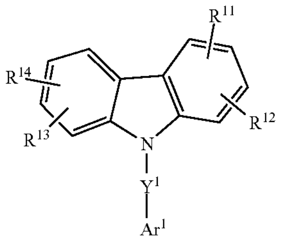

In the above Chemical Formula 2, $Y^1$ is a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof, $Ar^1$ is a substituted or unsubstituted C6 to C30 aryl group, a substituted or unsubstituted C2 to C30 heteroaryl group, or a combination thereof, $R^{11}$ to $R^{14}$ are independently hydrogen, deuterium, a substituted or unsubstituted C1 to C20 alkyl group, a substituted or unsubstituted C6 to C50 aryl group, a substituted or unsubstituted C2 to C50 heteroaryl group, or a combination thereof, and at least one of $R^1$ to $R^4$ and $Ar^1$ includes a substituted or unsubstituted triphenylene group or a substituted or unsubstituted carbazole group.

According to another embodiment, an organic optoelectric device includes an anode and a cathode facing each other, and at least one organic layer interposed between the anode and the cathode, wherein the organic layer includes the composition.

According to yet another embodiment, a display device including the organic optoelectric device is provided.

Advantageous Effect

An organic optoelectric device having high efficiency and long life-span may be realized.

DESCRIPTION OF DRAWINGS

FIGS. 1 and 2 are cross-sectional views of each organic light emitting diode according to one embodiment.

BEST MODE

Hereinafter, embodiments of the present invention are described in detail. However, these embodiments are exemplary, and this disclosure is not limited thereto.

As used herein, when a definition is not otherwise provided, the term "substituted" refers to one substituted with a deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C3 to C30 cycloalkyl group, a C3 to C30 heterocycloalkyl group, a C6 to C30 aryl group, a C6 to C30 heteroaryl group, a C1 to C20 alkoxy group, a fluoro group, a C1 to C10 trifluoroalkyl group such as a trifluoromethyl group, and the like, or a cyano group, instead of at least one hydrogen of a substituent or a compound.

In addition, two adjacent substituents of the substituted halogen, hydroxy group, amino group, substituted or unsubstituted C1 to C20 amine group, a nitro group, substituted or unsubstituted C3 to C40 silyl group, C1 to C30 alkyl group, C1 to C10 alkylsilyl group, C3 to C30 cycloalkyl group, C3 to C30 heterocycloalkyl group, C6 to C30 aryl group, C6 to C30 heteroaryl group, C1 to C20 alkoxy group, fluoro group, C1 to C10 trifluoroalkyl group such as trifluoromethyl group and the like, or cyano group may be fused with each other to form a ring. For example, the substituted C6 to C30 aryl group may be fused with another adjacent substituted C6 to C30 aryl group to form a substituted or unsubstituted fluorene ring.

In the present specification, when specific definition is not otherwise provided, the term "hetero" refers to one including 1 to 3 hetero atoms selected from N, O, S, P, and Si, and remaining carbons in one compound or substituent.

As used herein, when a definition is not otherwise provided, the term "alkyl group" may refer to an aliphatic hydrocarbon group. The alkyl group may refer to "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group includes 1 to 4 carbons in alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

As used herein, the term "aryl group" refers to a substituent including all element of the cycle having p-orbitals which form conjugation, and may be monocyclic, polycyclic or fused ring polycyclic (i.e., rings sharing adjacent pairs of carbon atoms) functional group.

As used herein, the term "heteroaryl group" may refer to aryl group including 1 to 3 hetero atoms selected from N, O, S, P, and Si and remaining carbons in one functional group. The heteroaryl group may be a fused ring where each ring may include the 1 to 3 heteroatoms.

More specifically, the substituted or unsubstituted C6 to C30 aryl group and/or the substituted or unsubstituted C2 to C30 heteroaryl group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzothiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted fluorenyl group, a substituted or unsubstituted dibenzofuranyl group, a substituted or unsubstituted dibenzothiopheneyl group, a substituted or unsubstituted carbazole group, or a combination thereof, but are not limited thereto.

In the specification, hole characteristics refer to characteristics capable of donating an electron to form a hole when electric field is applied, and characteristics that hole formed in the anode is easily injected into the emission layer and transported in the emission layer due to conductive characteristics according to HOMO level.

In addition, electron characteristics refer to characteristics capable of accepting an electron when electric field is applied, and characteristics that electron formed in the cathode is easily injected into the emission layer and transported in the emission layer due to conductive characteristics according to LUMO level.

Hereinafter, a composition according to one embodiment is described.

The composition according to one embodiment includes at least two kinds of host compounds and a dopant, and the host compounds include a first host compound having bipolar characteristics having relatively stronger electron characteristics and a second host compound having bipolar characteristics having relatively stronger hole characteristics.

The first host compound is a compound having bipolar characteristics having relatively stronger electron characteristics, and represented by the following Chemical Formula 1.

[Chemical Formula 1]

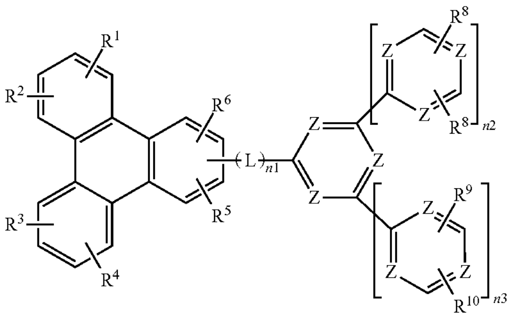

In the above Chemical Formula 1,

Z is independently N or $CR^a$, at least one of Z is N, $R^1$ to $R^{10}$ and $R^a$ are independently hydrogen, deuterium, a substituted or unsubstituted C1 to C10 alkyl group, a substituted or unsubstituted C6 to C12 aryl group, or a combination thereof, in the above Chemical Formula 1, the total number of 6-membered rings substituting the triphenylene group is less than or equal to 6, L is a substituted or unsubstituted phenylene group, a substituted or unsubstituted biphenylene group or a substituted or unsubstituted terphenylene group, n1 to n3 are independently 0 or 1, and n1+n2+n3>1.

The 6-membered rings substituting the triphenylene group indicate all the 6-membered rings directly or indirectly linked to the triphenylene group and include 6-membered rings consisting of a carbon atom, a nitrogen atom, or a combination thereof.

The first host compound may be represented by for example the following Chemical Formula 1-I or 1-II depending on the bonding position of the triphenylene group.

[Chemical Formula 1-I]

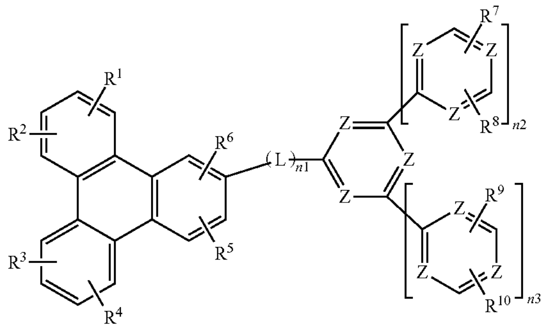

[Chemical Formula 1-II]

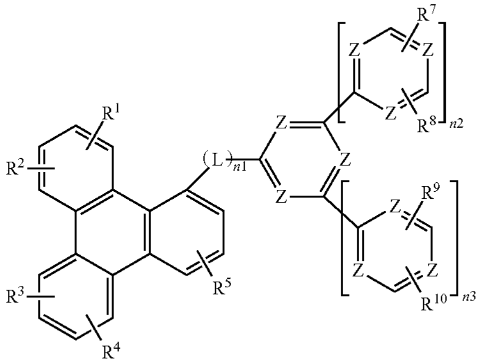

In the above Chemical Formula 1-I or 1-II, Z, $R^1$ to $R^{10}$, L and n1 to n3 are the same as described above.

The first host compound includes the triphenylene group and at least one nitrogen-containing heteroaryl group.

The first host compound includes at least one nitrogen-containing ring and thereby, may have a structure of easily accepting electrons when an electric field is applied thereto and thus, decrease a driving voltage of an organic optoelectric device including the first host compound.

In addition, the first host compound has a bipolar structure by including both a triphenylene moiety of easily accepting holes and a nitrogen-containing ring moiety of easily accepting electrons and may appropriately balance a flow of the holes and the electrons, and accordingly, improve efficiency of an organic optoelectric device when applied thereto.

The first host compound represented by the above Chemical Formula 1 has at least one kink structure as a center of an arylene group and/or a heteroarylene group.

The kink structure is a structure that two linking parts of the arylene group and/or the heteroarylene group are not a linear structure. For example, as for phenylene, ortho phenylene o-phenylene) and meta phenylene (m-phenylene) have the kink structure where two linking parts do not form a linear structure, while para phenylene (p-phenylene) has no kink structure because where two linking parts form a linear structure.

In the above Chemical Formula 1, the kink structure may be formed as a center of a linking group (L) and/or an arylene group/a heteroarylene group.

For example, when n1 in the above Chemical Formula 1 is 0, that is, there is no linking group (L), a kink structure may be formed as a center of an arylene group/a heteroarylene group, and for example, the compound may be represented by the following Chemical Formula 1a or 1b.

[Chemical Formula 1a]

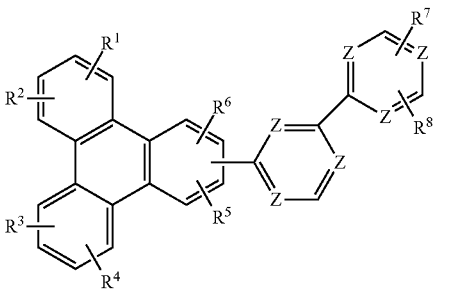

[Chemical Formula 1b]

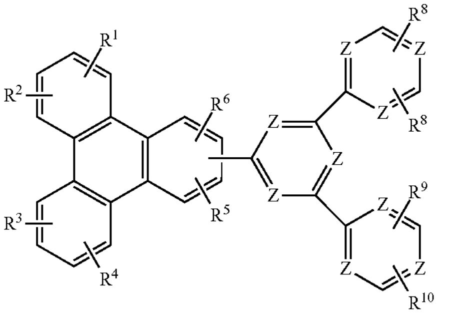

In the above Chemical Formula 1a or 1b, Z, $R^1$ to $R^{10}$ and L are the same as described above.

For example, when n1 in the above Chemical Formula 1 is 1, a kink structure may be formed as a center of a linking group (L), and for example, the L is may be a substituted or unsubstituted phenylene having the kink structure, a substituted or unsubstituted biphenylene group having the kink structure, or a substituted or unsubstituted terphenylene group having the kink structure. The L may be selected from, for example substituted or unsubstituted groups listed in the following Group 1.

[Group 1]

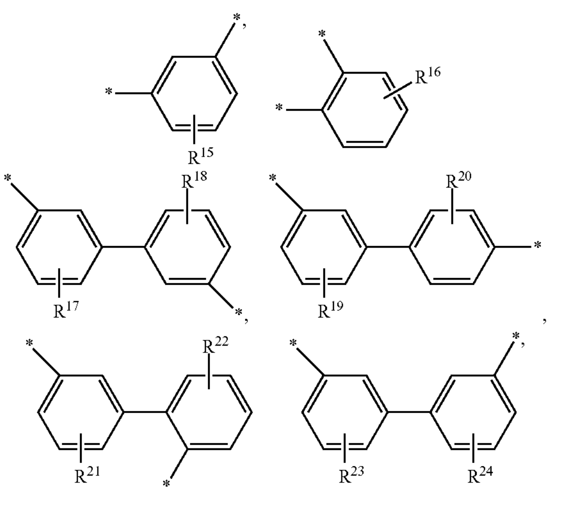

-continued

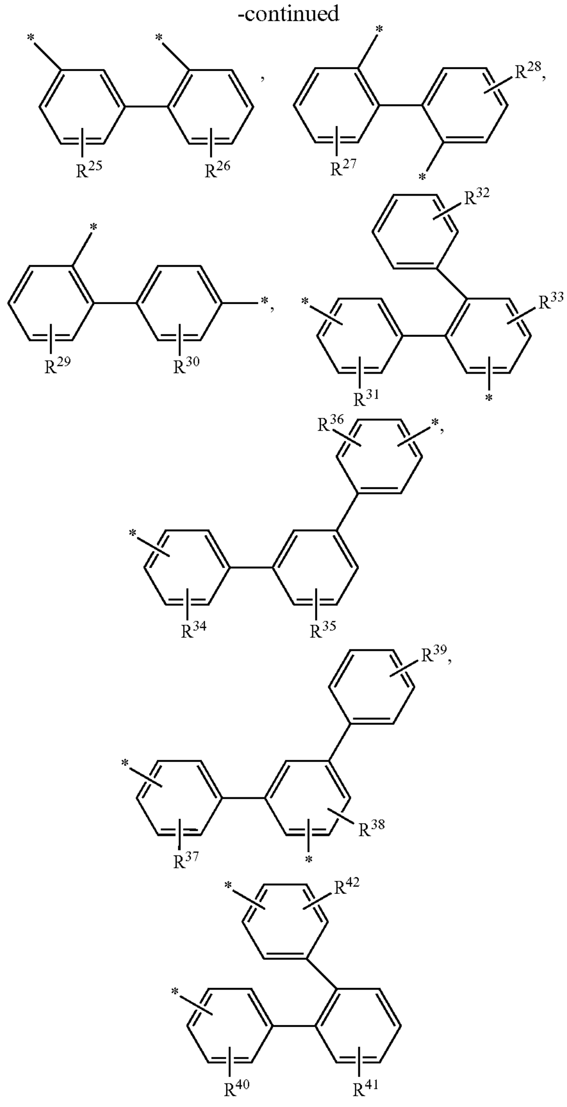

In the Group 1, $R^{15}$ to $R^{42}$ are independently hydrogen, deuterium, a substituted or unsubstituted C1 to C10 alkyl group, a substituted or unsubstituted C3 to C30 cycloalkyl group, a substituted or unsubstituted C3 to C30 heterocycloalkyl group, a substituted or unsubstituted C6 to C30 aryl group, a substituted or unsubstituted C2 to C30 heteroaryl group, a substituted or unsubstituted amine group, a substituted or unsubstituted C6 to C30 arylamine group, a substituted or unsubstituted C6 to C30 heteroarylamine group, a substituted or unsubstituted C1 to C30 alkoxy group, a halogen, a halogen-containing group, a cyano group, a hydroxyl group, an amino group, a nitro group, a carboxyl group, ferrocenyl group, or a combination thereof.

The first host compound may have at least two kink structures and for example, two to four kink structures.

The first host compound may appropriately localize charges, which are electrons and holes, and control a conjugation-system flow due to the above kink structure, and thus improve a life-span of an organic optoelectric device to which the composition is applied.

In addition, in Chemical Formula 1, the total number of 6-membered rings substituting the triphenylene group is limited to be less than or equal to 6, and thereby thermal decomposition of the compound by a high temperature during a deposition process may be decreased.

In addition, the first host compound may be effectively prevented from stacking due to the structure and improve process stability and simultaneously, lower a deposition temperature. This stacking prevention effect may be further increased when the compound includes the linking group (L) of the above Chemical Formula 1.

The first host compound may be represented by one of, for example the following Chemical Formulae 1c to 1t.

[Chemical Formula 1c]

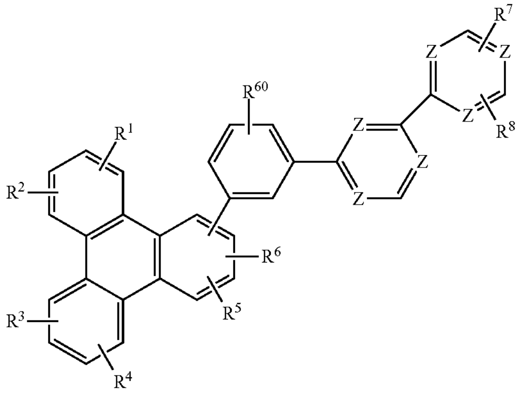

[Chemical Formula 1d]

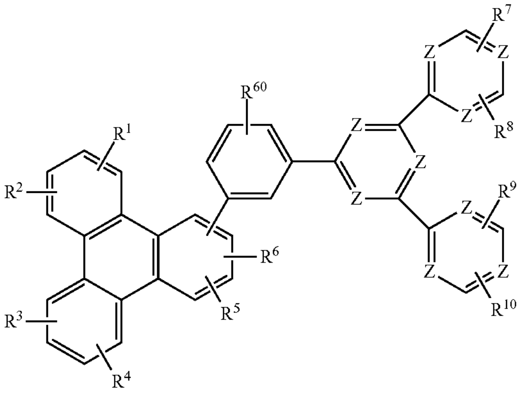

[Chemical Formula 1e]

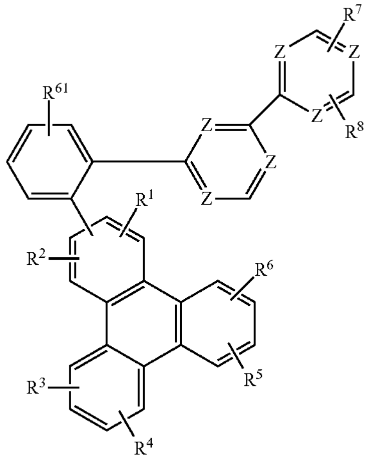

-continued

[Chemical Formula 1f]

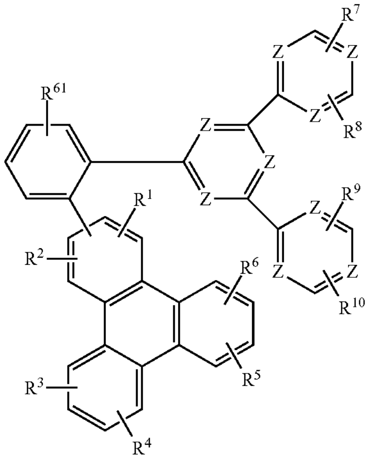

[Chemical Formula 1g]

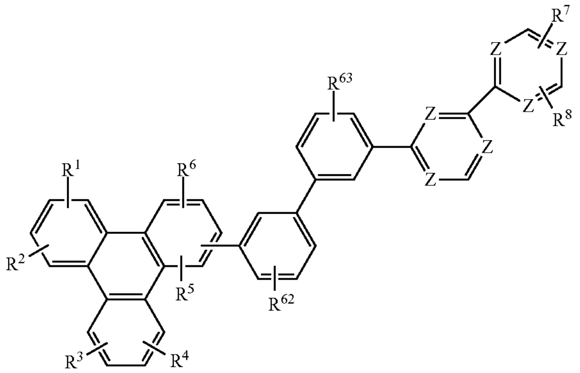

[Chemical Formula 1h]

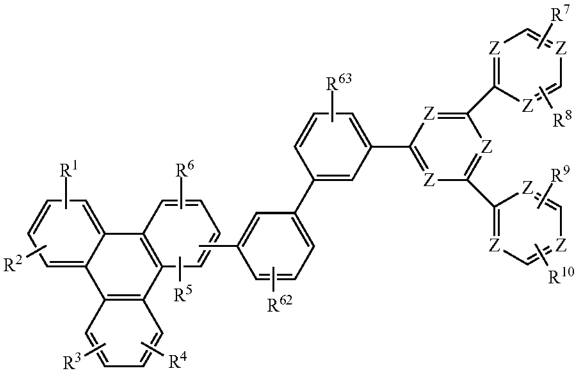

[Chemical Formula 1i]

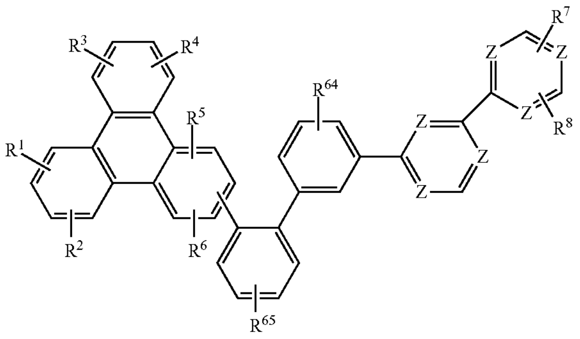

-continued
[Chemical Formula 1j]
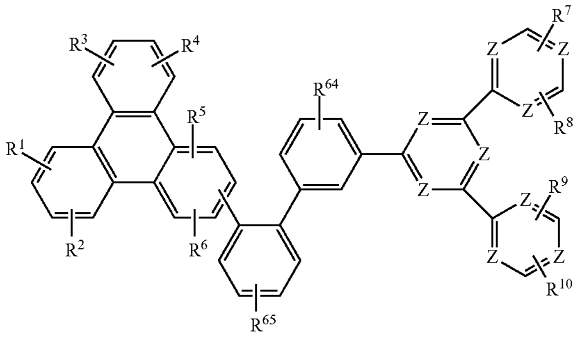
[Chemical Formula 1k]
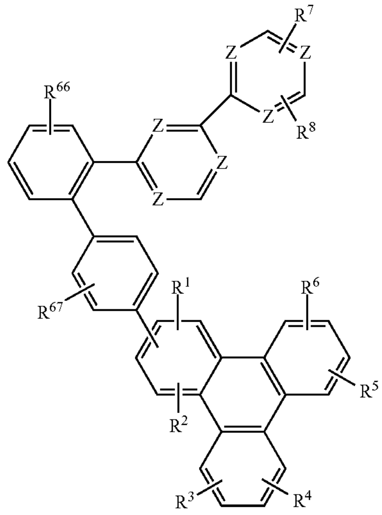
[Chemical Formula 1l]
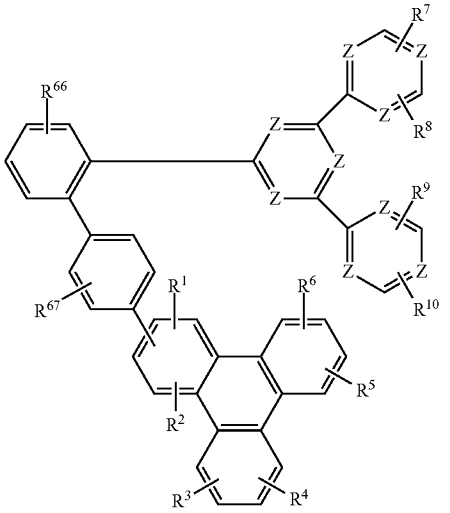
-continued
[Chemical Formula 1m]
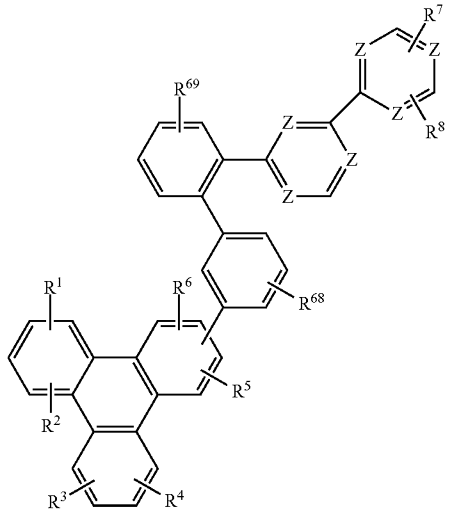
[Chemical Formula 1n]
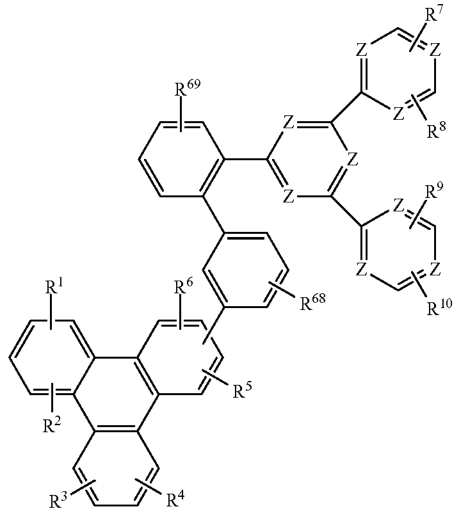
[Chemical Formula 1o]
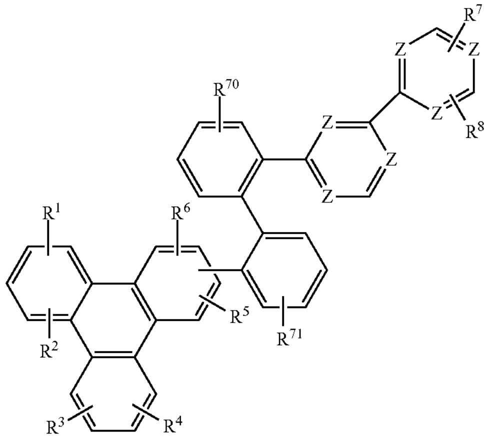

-continued

[Chemical Formula 1p]

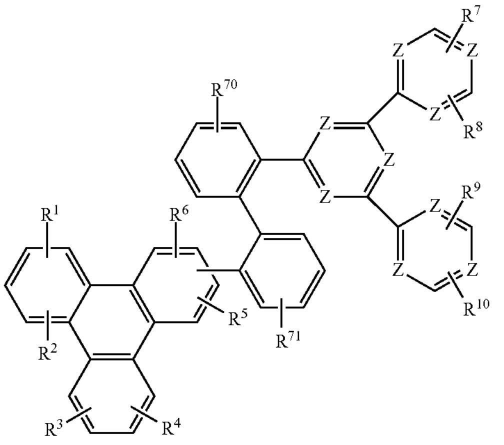

[Chemical Formula 1q]

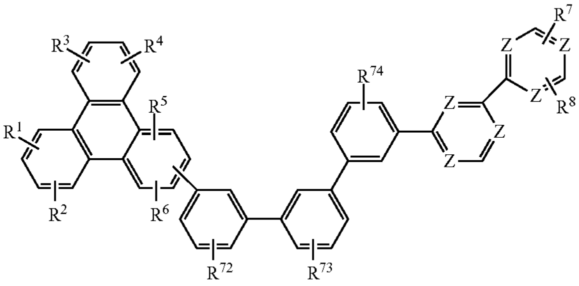

[Chemial Formula 1r]

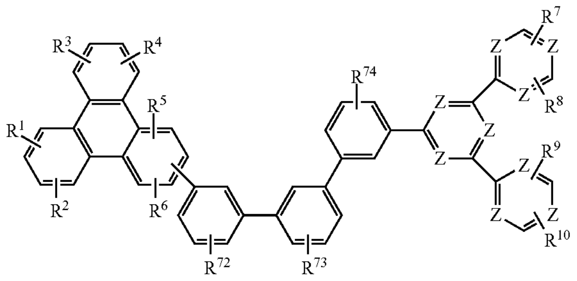

[Chemical Formula 1s]

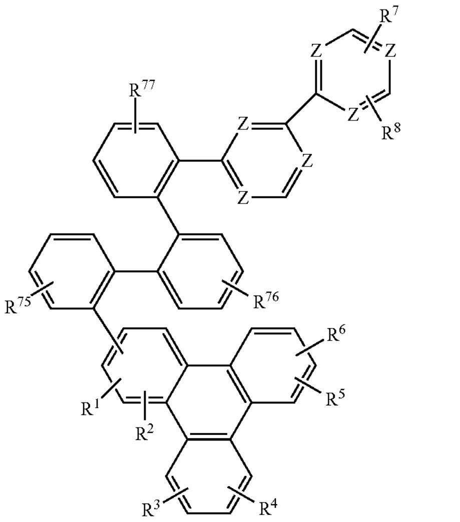

-continued

[Chemical Formula 1t]

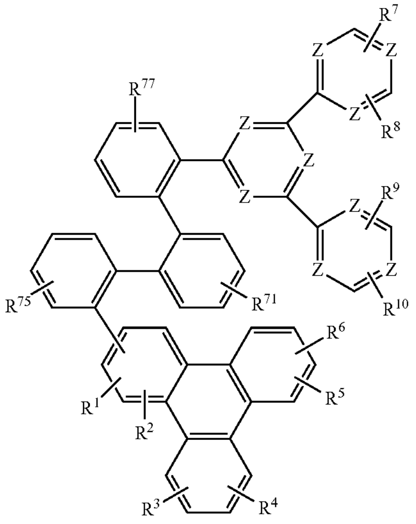

In the above Chemical Formulae 1c to 1t,

Z and $R^1$ to $R^{10}$ are the same as described above, and $R^{60}$ to $R^{77}$ are independently hydrogen, deuterium, a substituted or unsubstituted C1 to C10 alkyl group, a substituted or unsubstituted C3 to C30 cycloalkyl group, a substituted or unsubstituted C3 to C30 heterocycloalkyl group, a substituted or unsubstituted C6 to C30 aryl group, a substituted or unsubstituted C2 to C30 heteroaryl group, a substituted or unsubstituted amine group, a substituted or unsubstituted C6 to C30 arylamine group, a substituted or unsubstituted C6 to C30 heteroarylamine group, a substituted or unsubstituted C1 to C30 alkoxy group, a halogen, a halogen-containing group, a cyano group, a hydroxyl group, an amino group, a nitro group, a carboxyl group, a ferrocenyl group, or a combination thereof.

The first host compound may be, for example, a compound listed in the following Group 2, but is not limited thereto.

[Group 2]

A-1

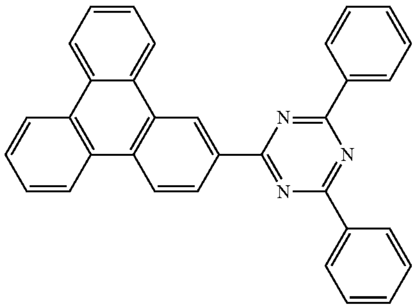

-continued
A-2
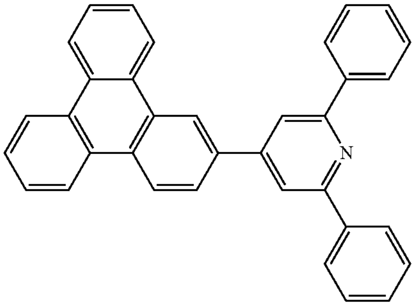
A-3
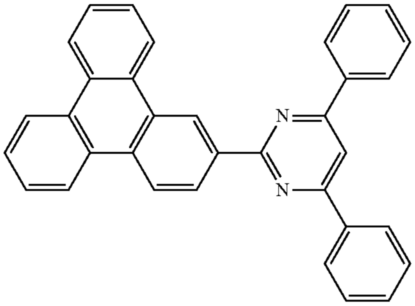
A-4
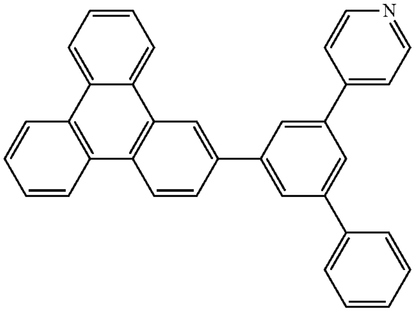
A-5
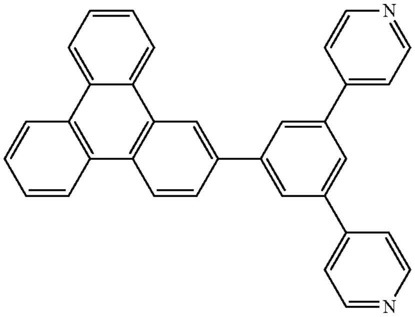
A-6
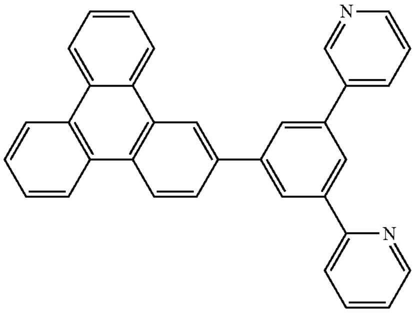
-continued
A-7
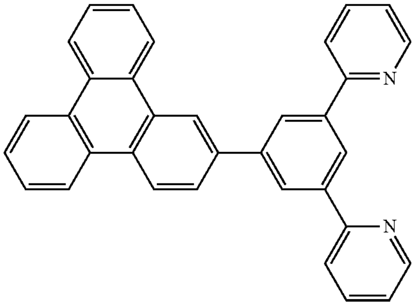
A-8
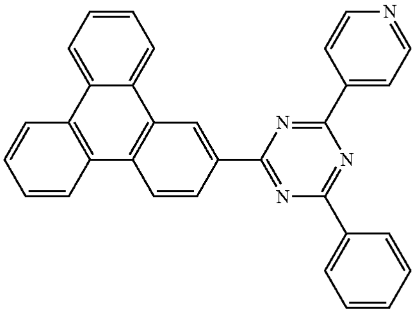
A-9
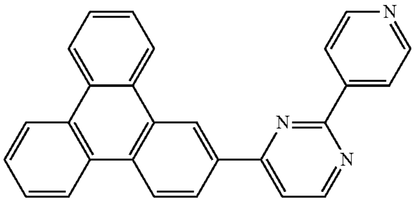
A-10
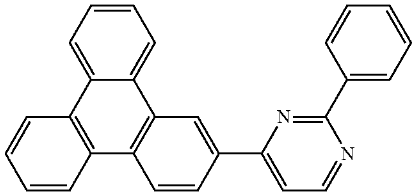
A-11
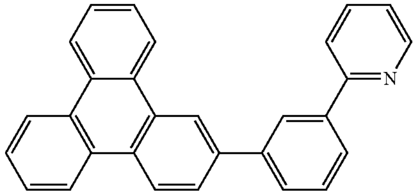
A-12
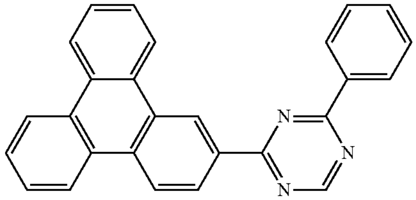

-continued
A-13
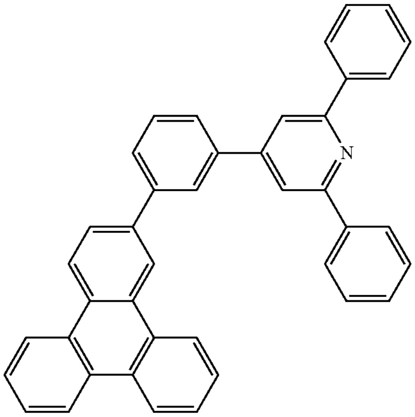
A-14
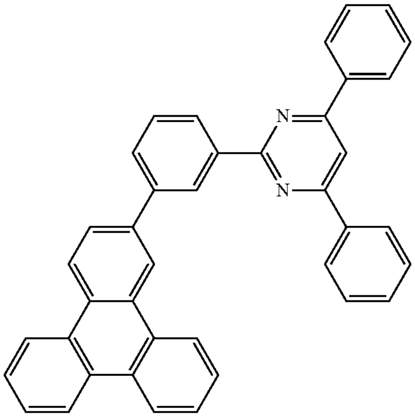
A-15
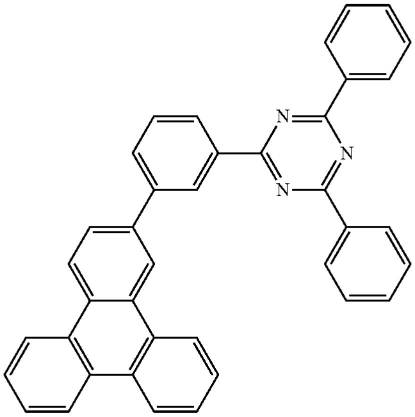
-continued
A-16
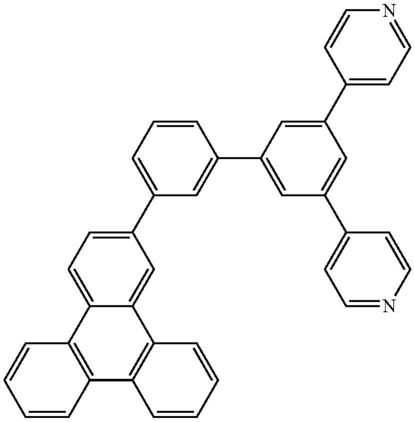
A-17
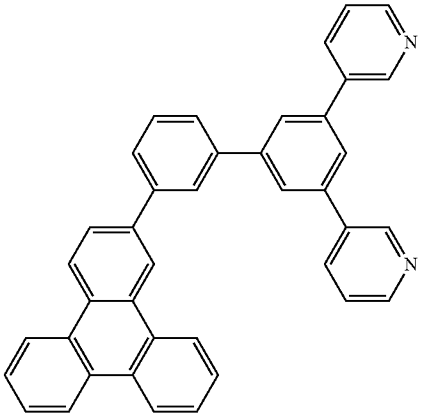
A-18
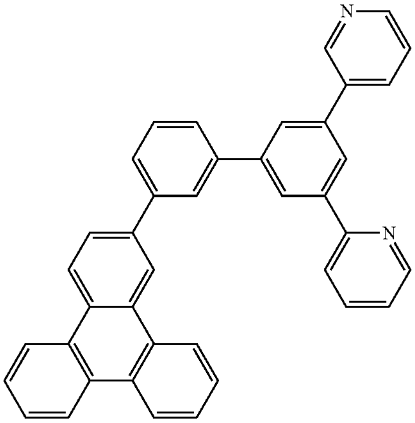

-continued
A-19
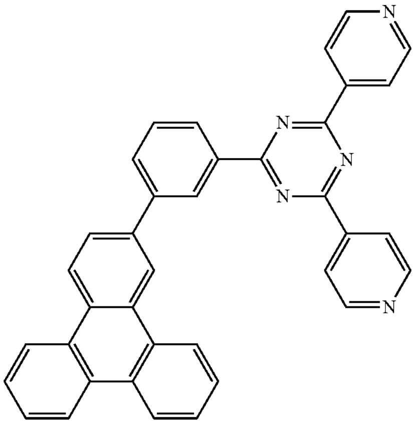
A-20
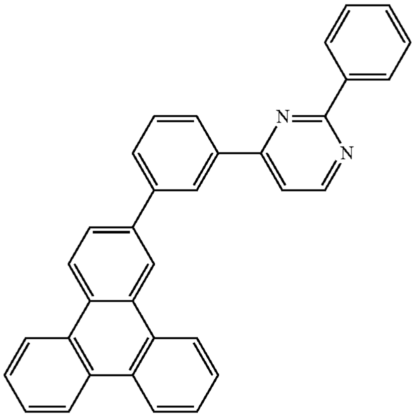
A-21
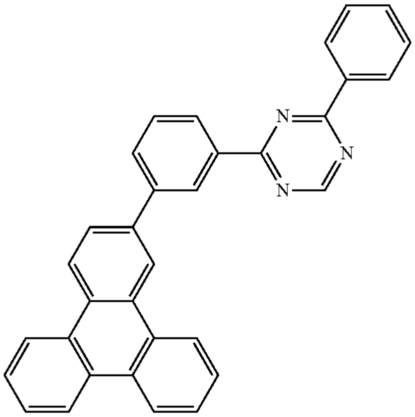
-continued
A-22
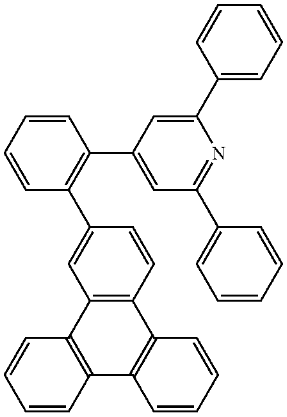
A-23
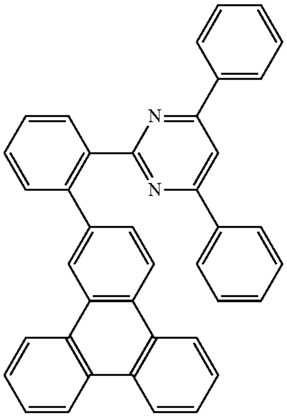
A-24
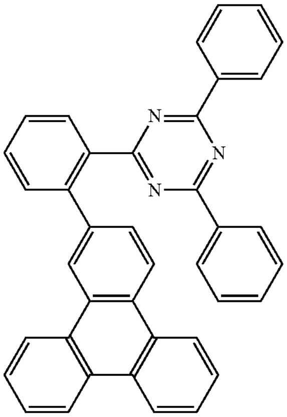

-continued
A-25
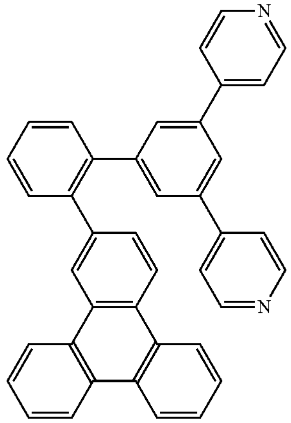
A-26
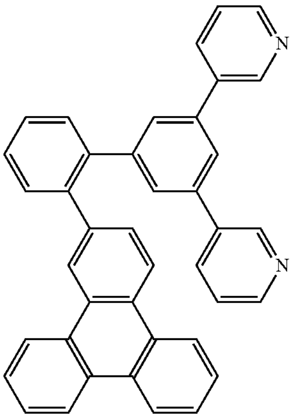
A-27
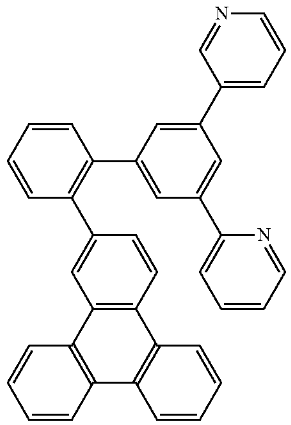
-continued
A-28
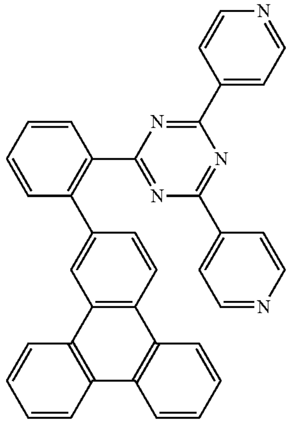
A-29
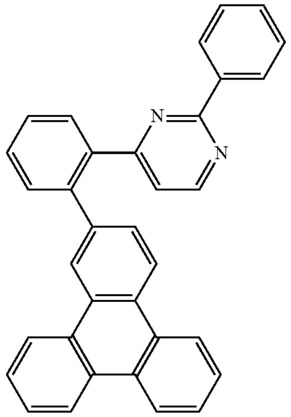
A-30
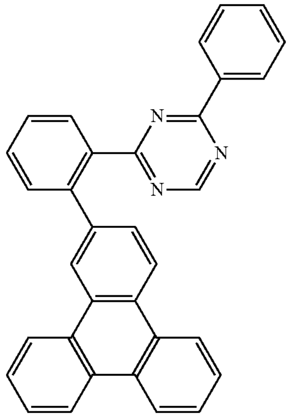

-continued
A-31
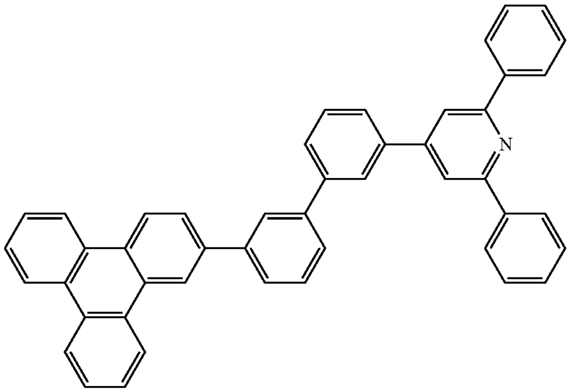
A-32
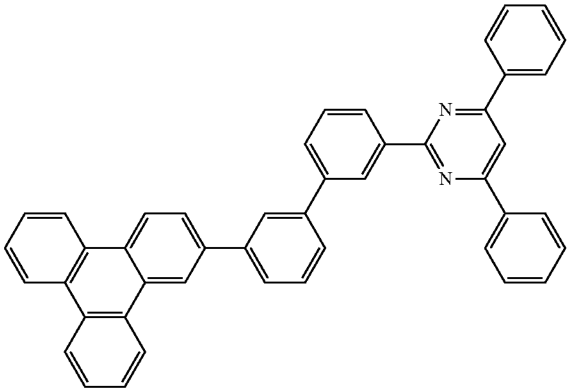
A-33
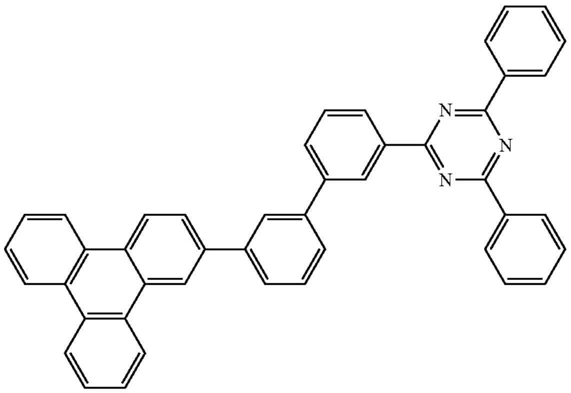
-continued
A-34
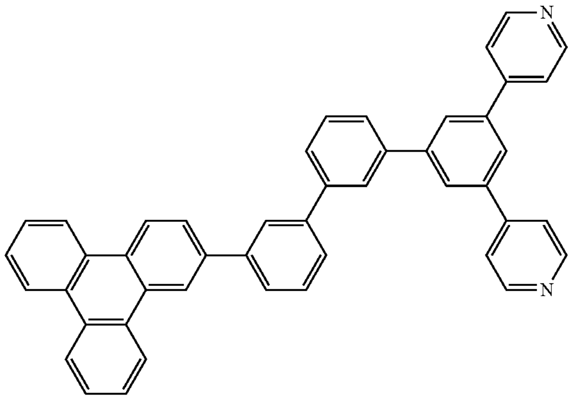
A-35
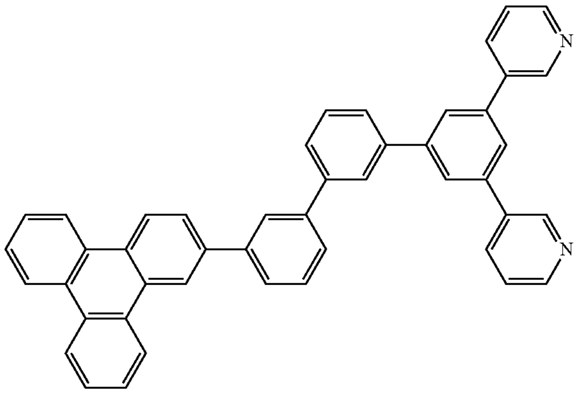
A-36
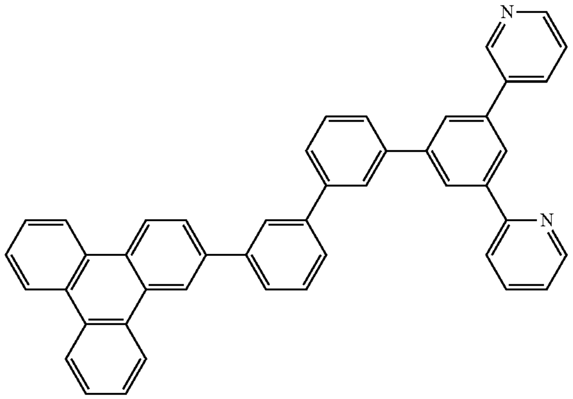

-continued
A-37
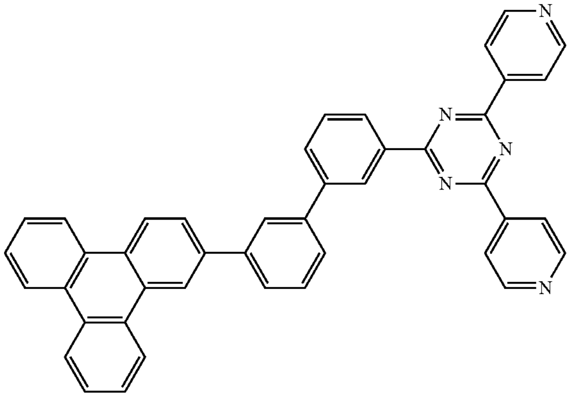
A-38
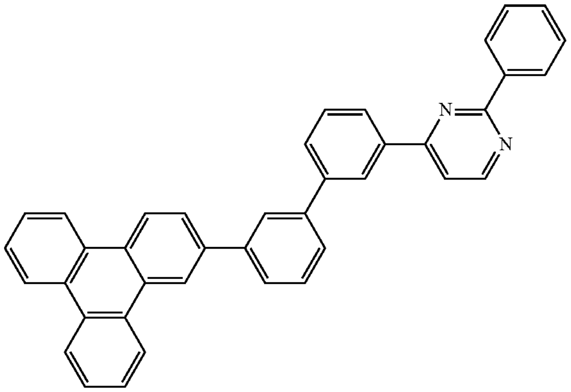
A-39
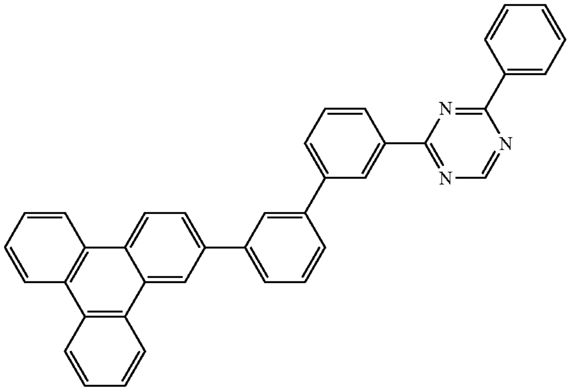
A-40
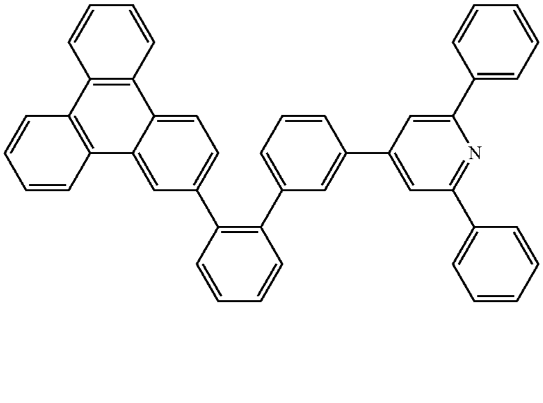
-continued
A-41
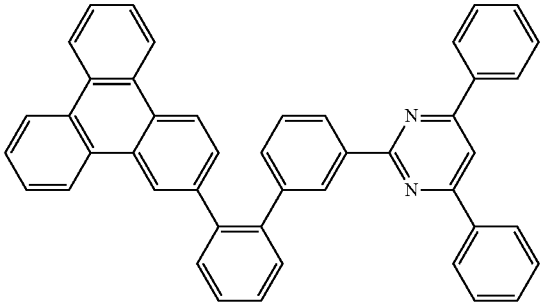
A-42
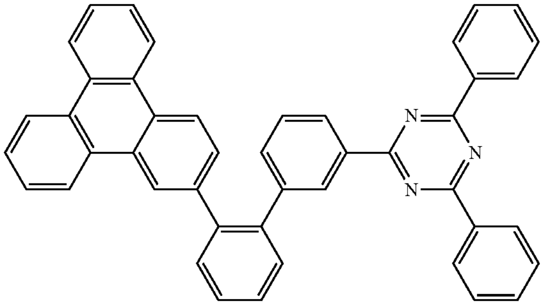
A-43
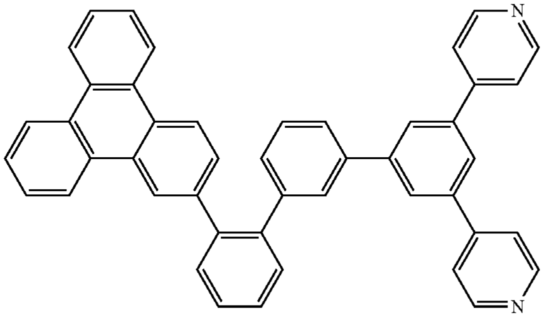
A-44
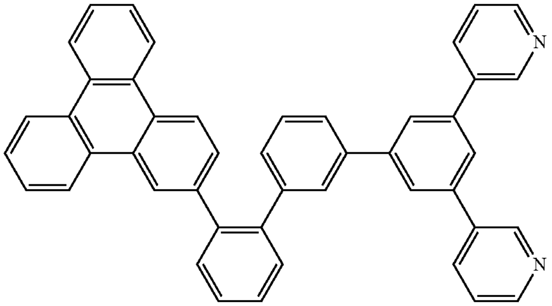

-continued
A-45
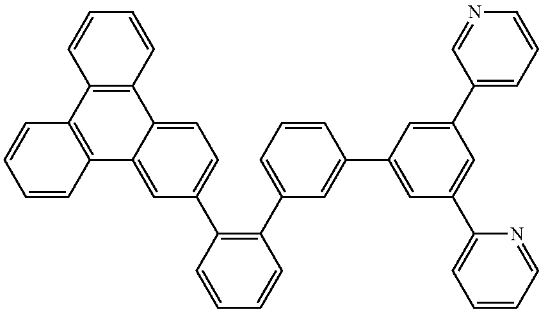
A-46
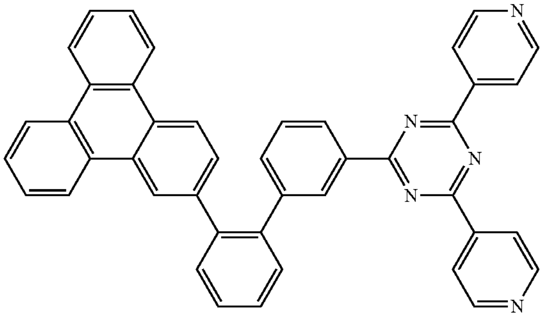
A-47
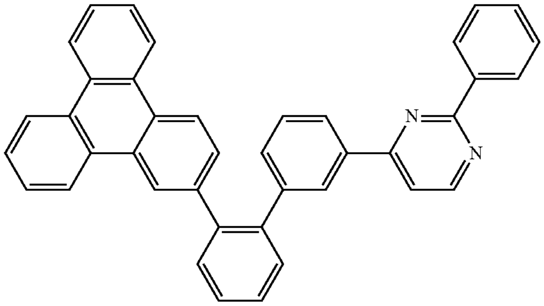
A-48
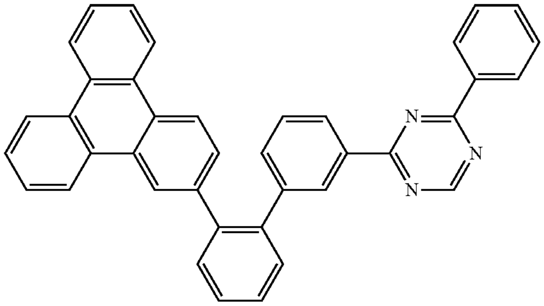
-continued
A-49
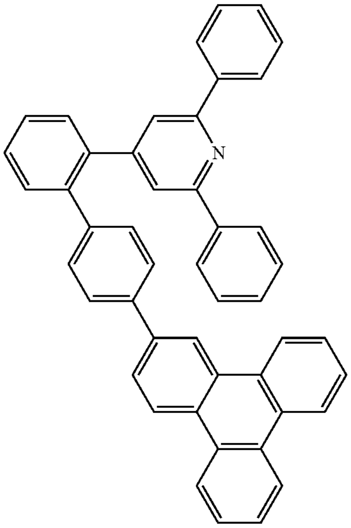
A-50
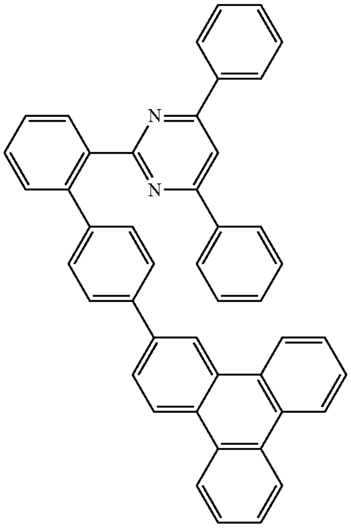
A-51
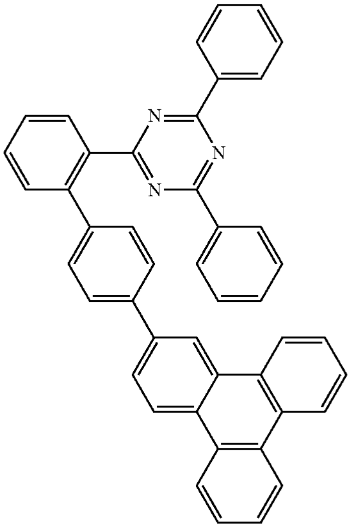

-continued
A-52
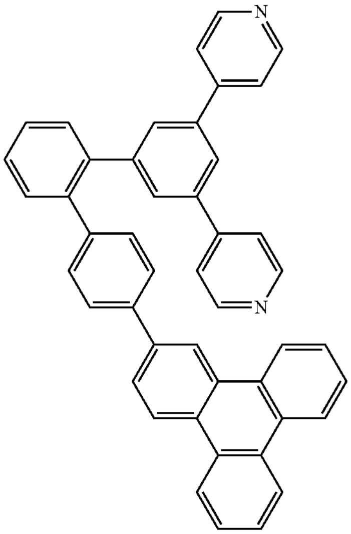
A-53
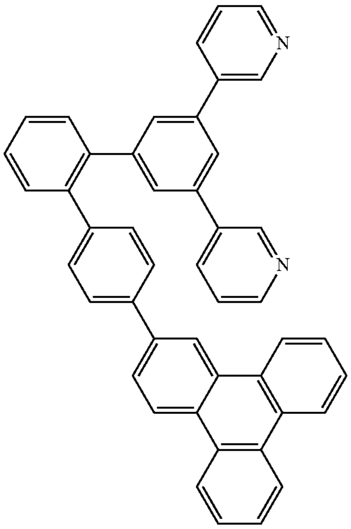
A-54
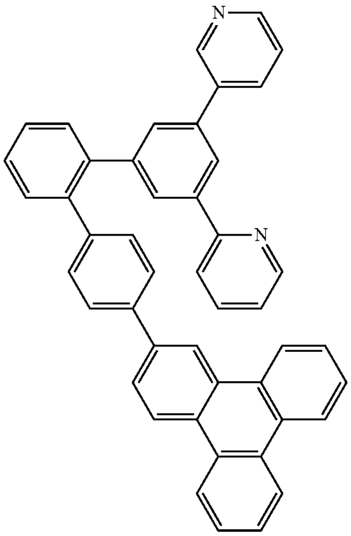
-continued
A-55
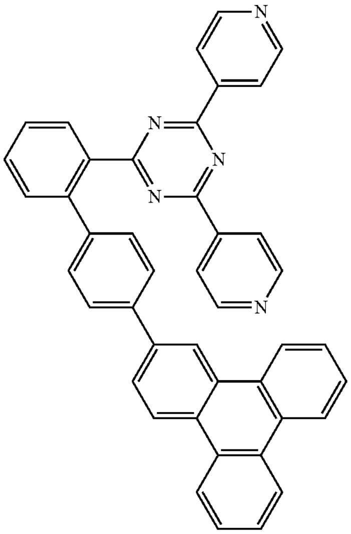
A-56
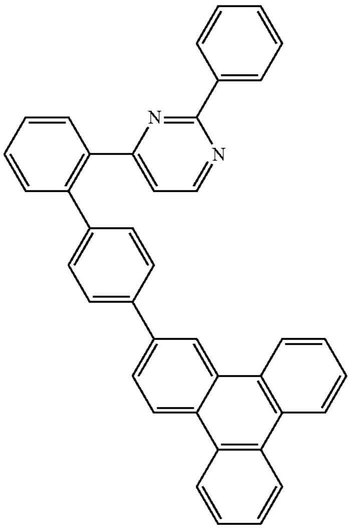
A-57
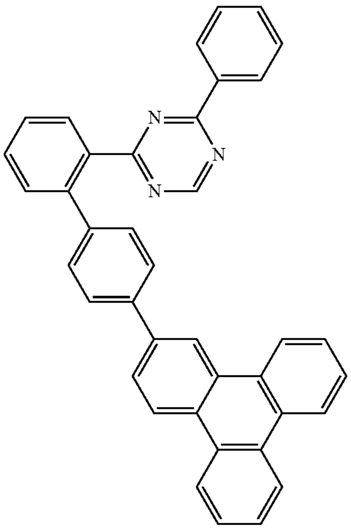

-continued
A-58
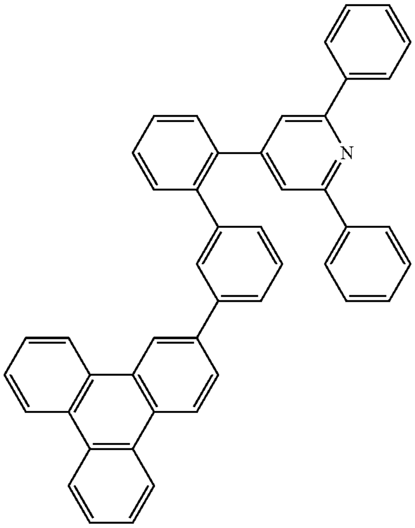
A-59
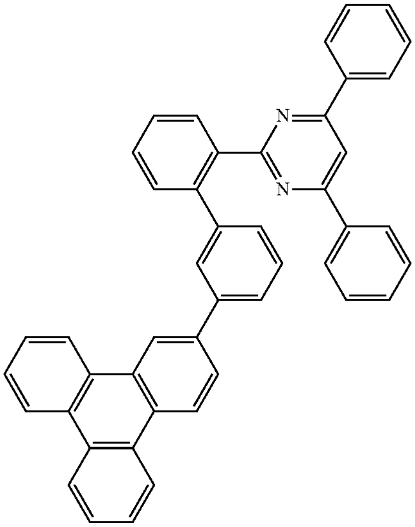
A-60
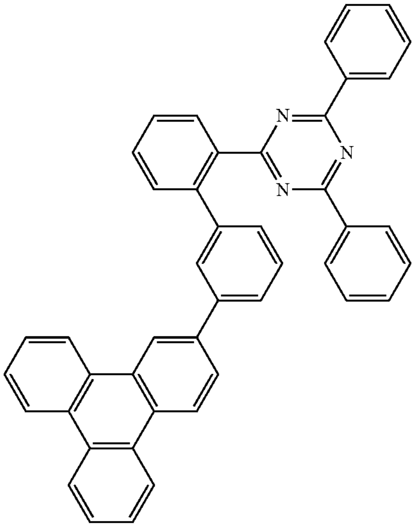
-continued
A-61
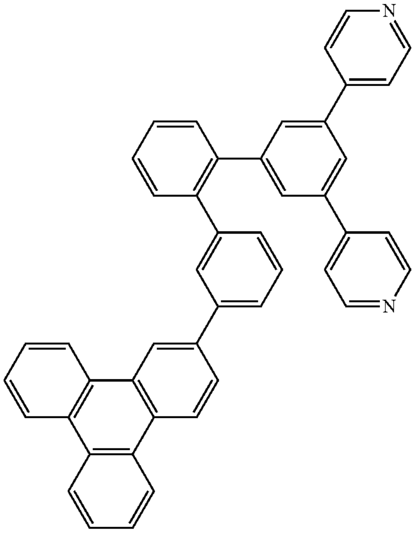
A-62
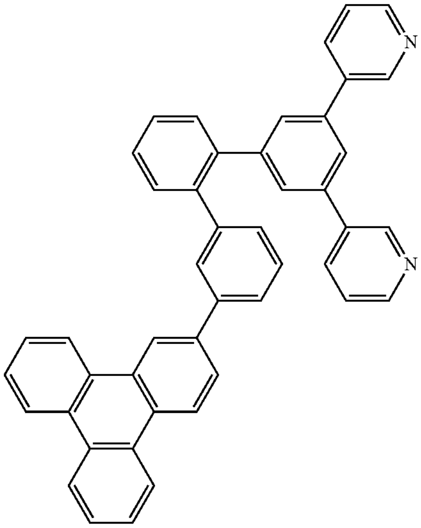
A-63
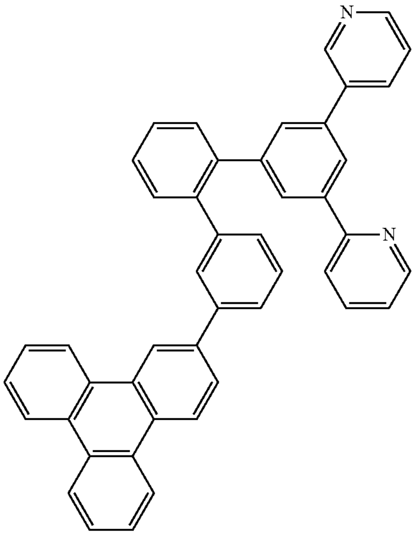

-continued
A-64
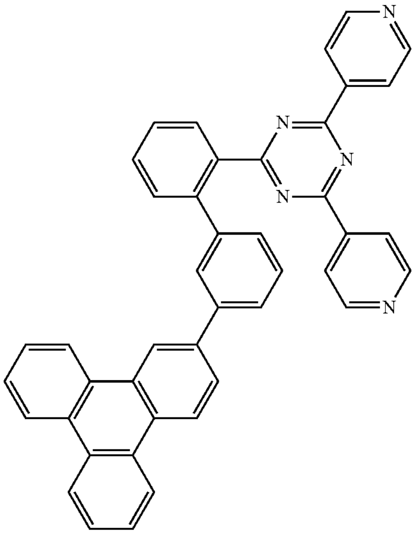
A-65
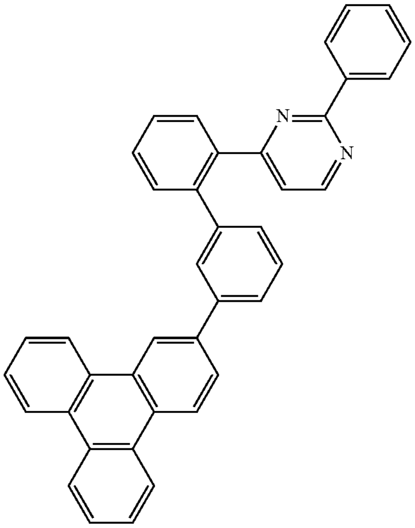
A-66
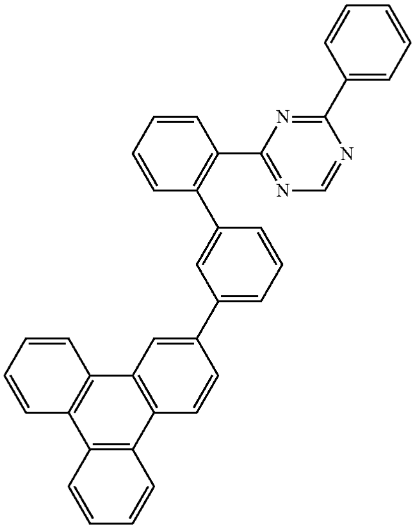
-continued
A-67
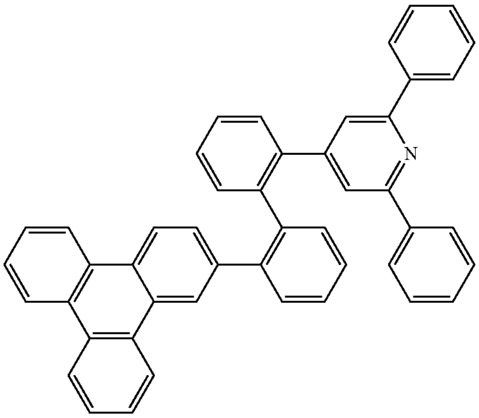
A-68
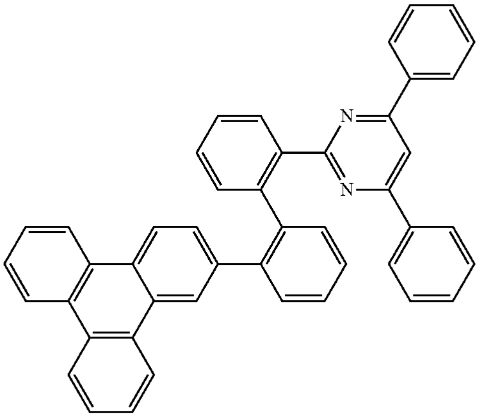
A-69
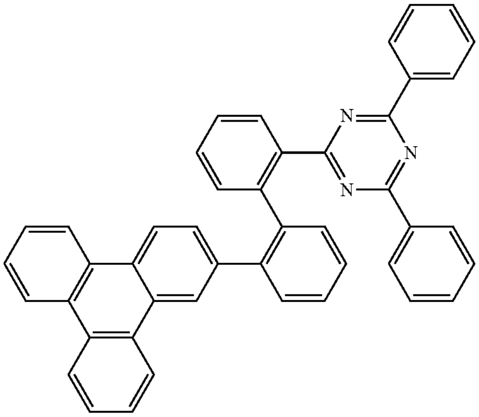

-continued
A-70
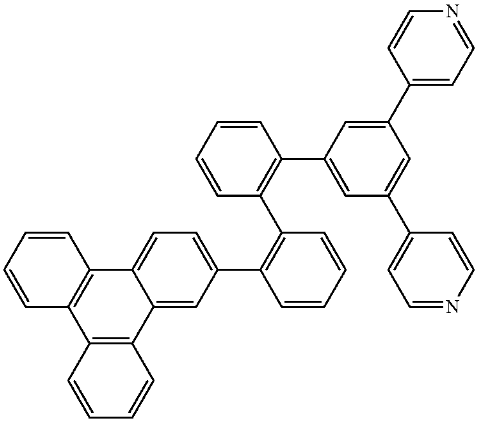
A-71
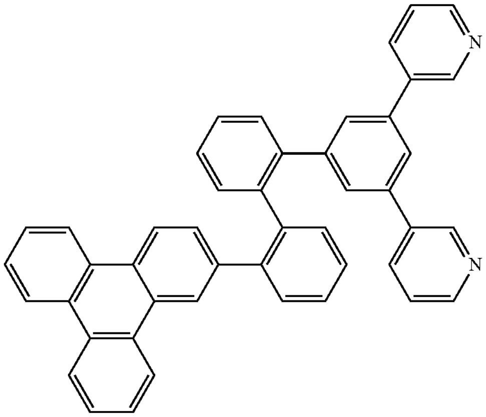
A-72
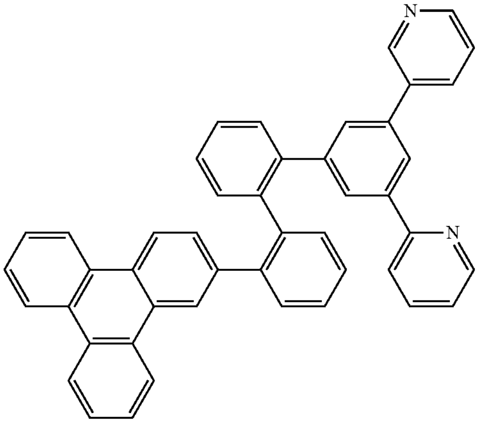
-continued
A-73
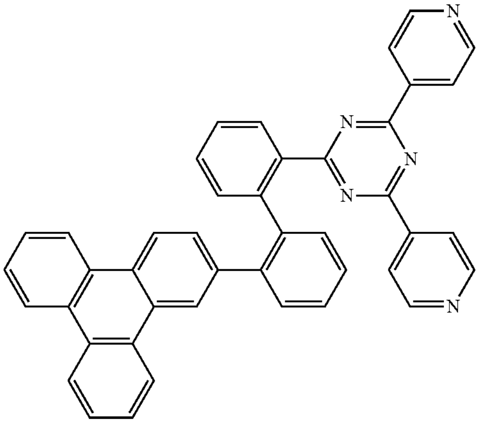
A-74
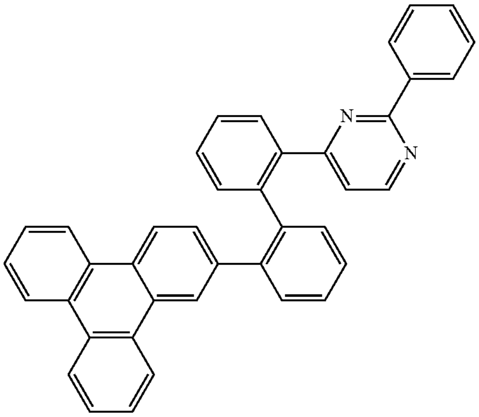
A-75
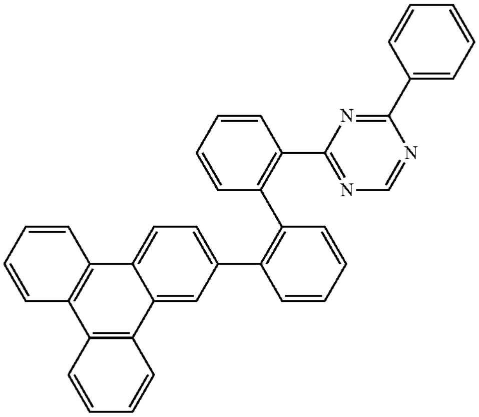
A-76
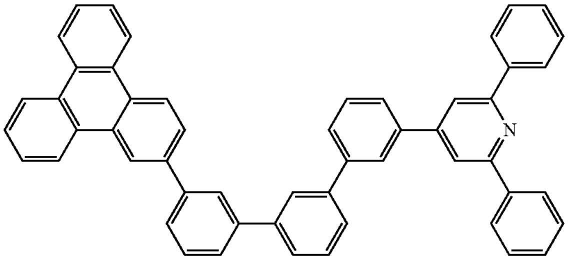

-continued
A-77
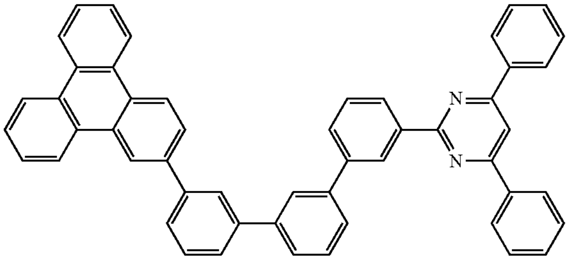
A-78
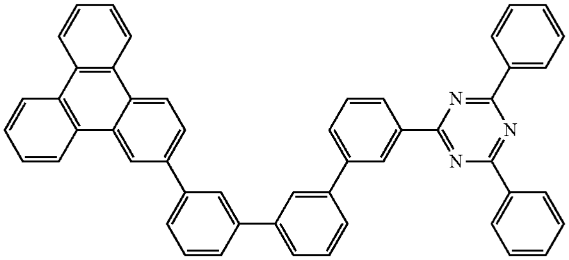
A-79
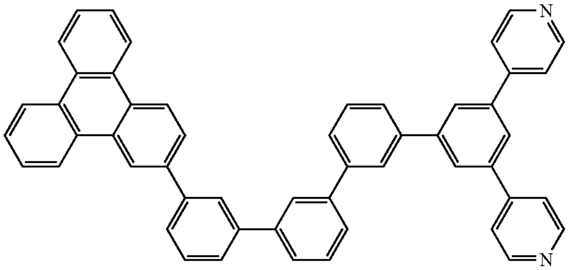
A-80
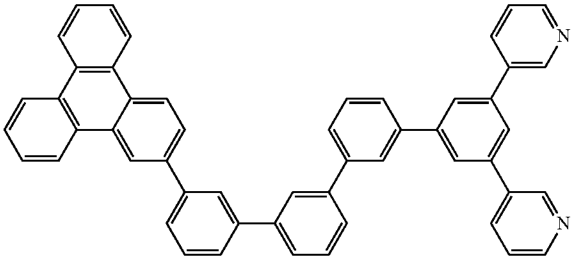
A-81
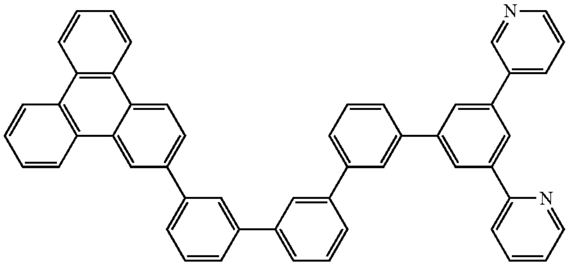
-continued
A-82
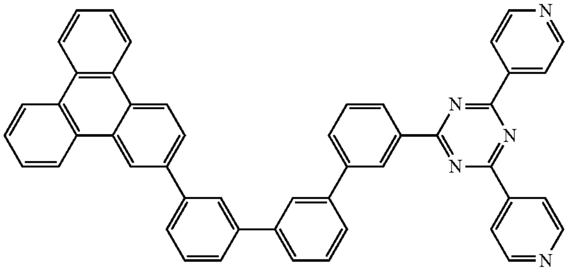
A-83
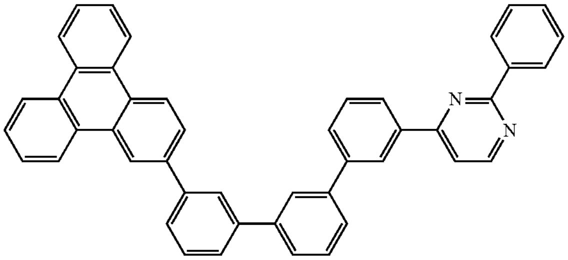
A-84
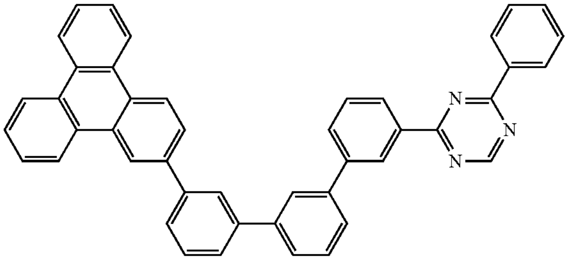
A-85
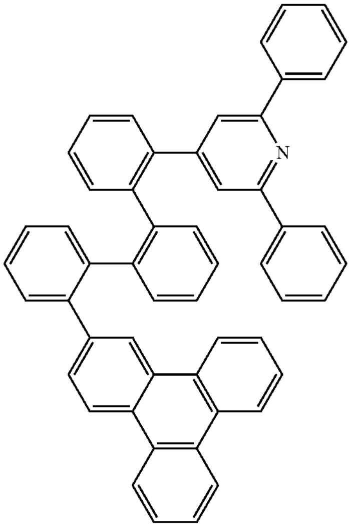

-continued
A-86
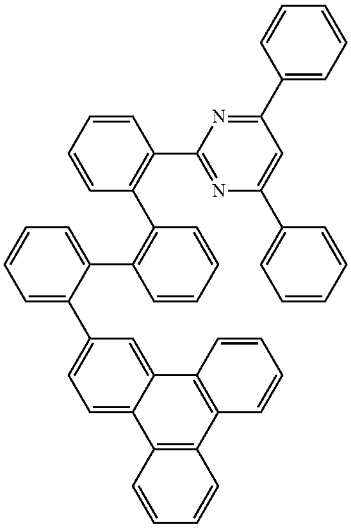
A-87
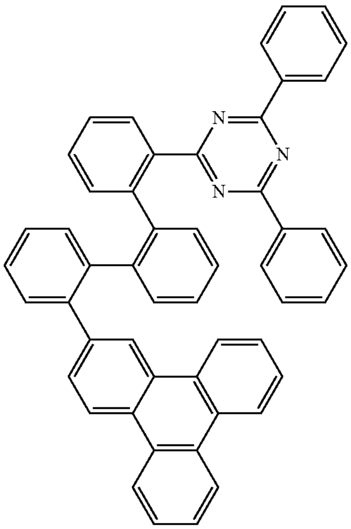
A-88
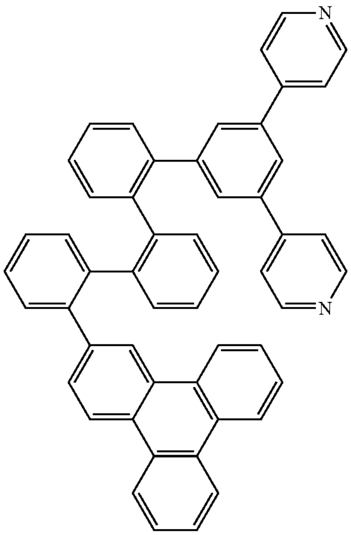
-continued
A-89
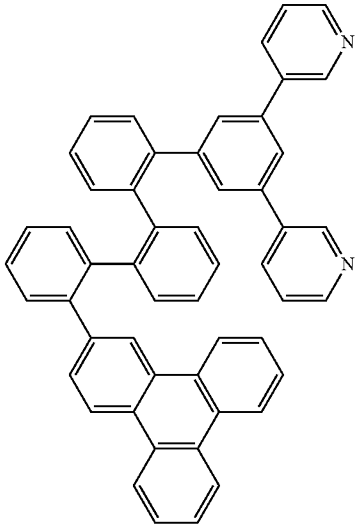
A-90
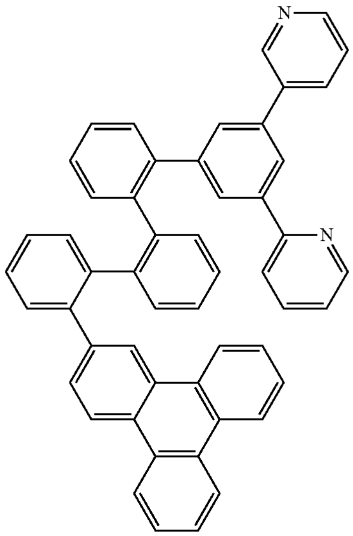
A-91
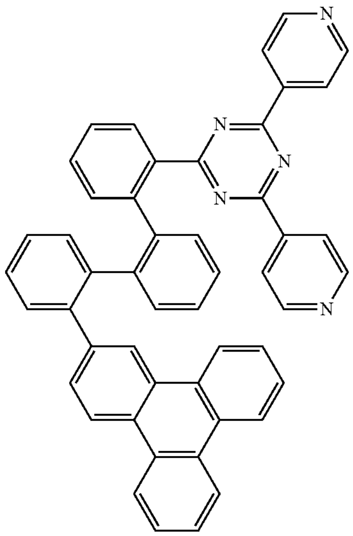

-continued
A-92
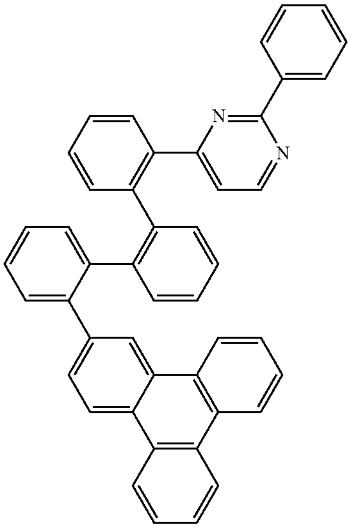
A-93
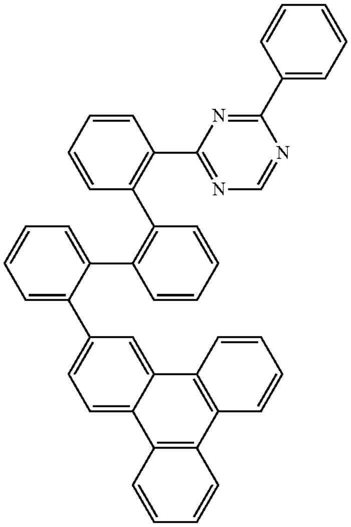
A-94
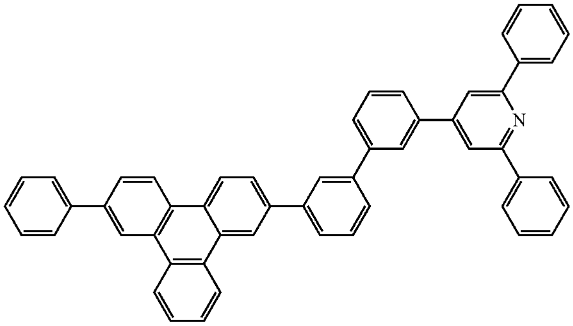
-continued
A-95
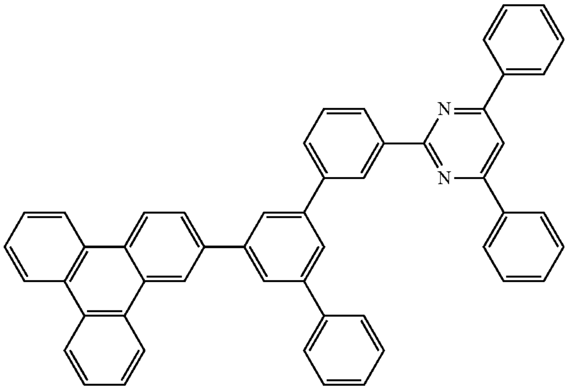
A-96
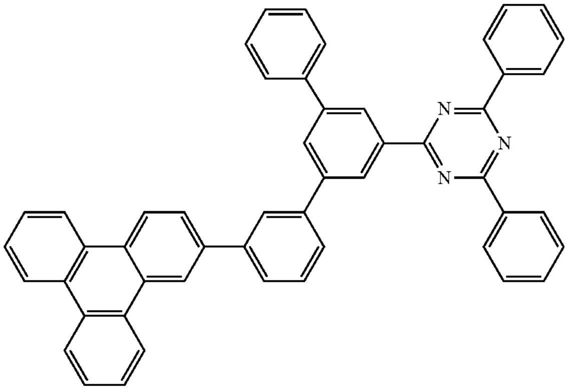
A-97
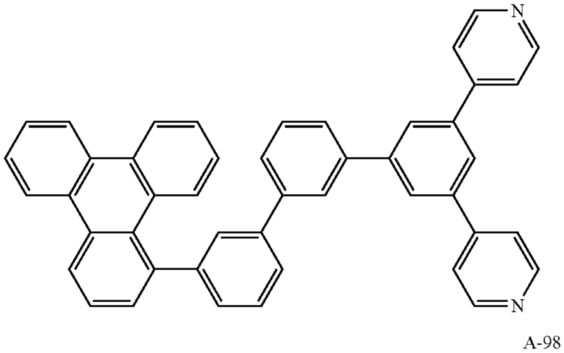
A-98
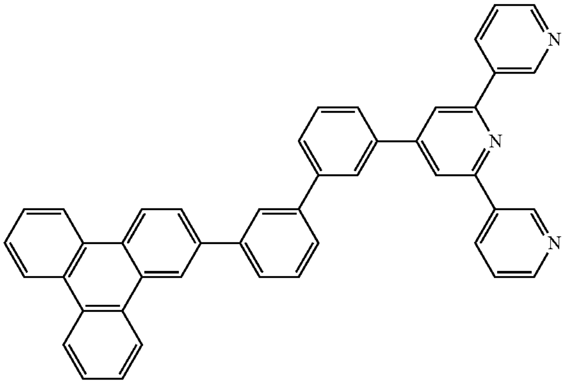

-continued
A-99
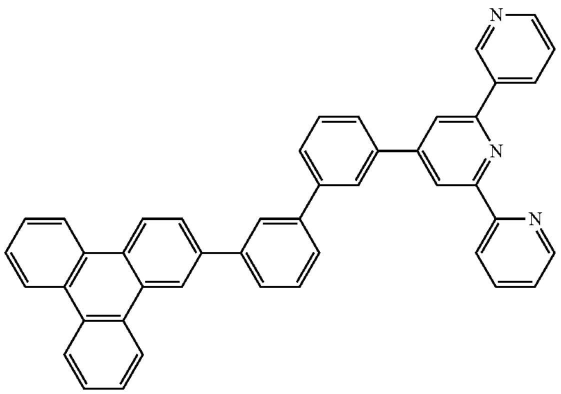
A-100
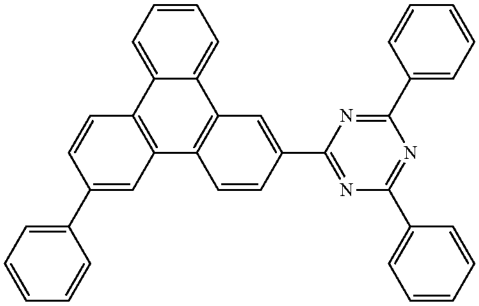
A-101
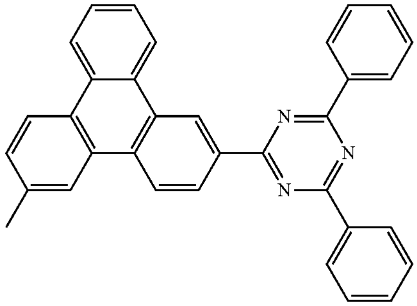
A-102
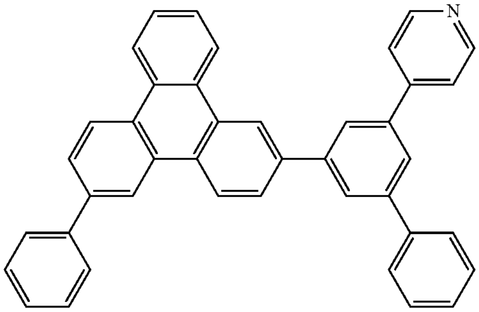
-continued
A-103
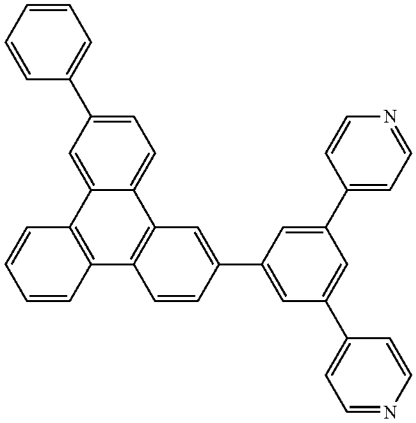
A-104
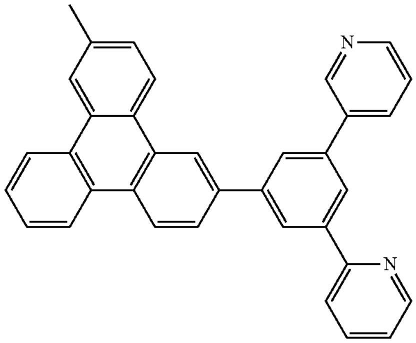
A-105
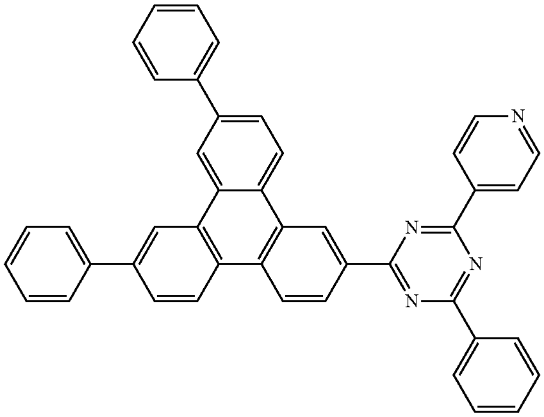
A-106
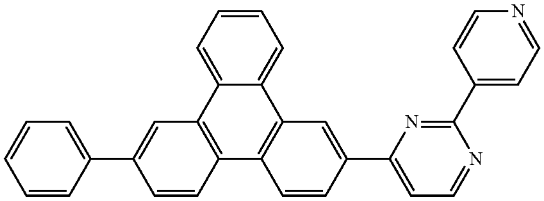

-continued
A-107
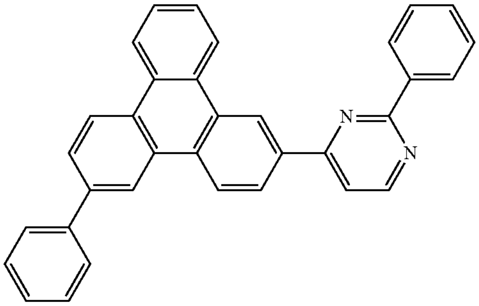
A-108
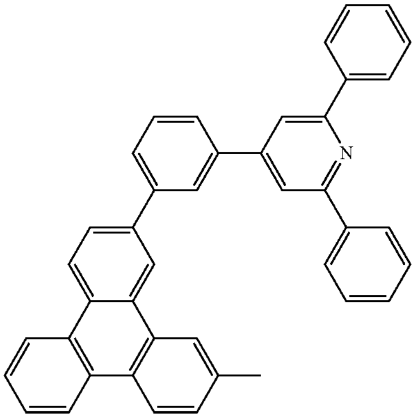
A-109
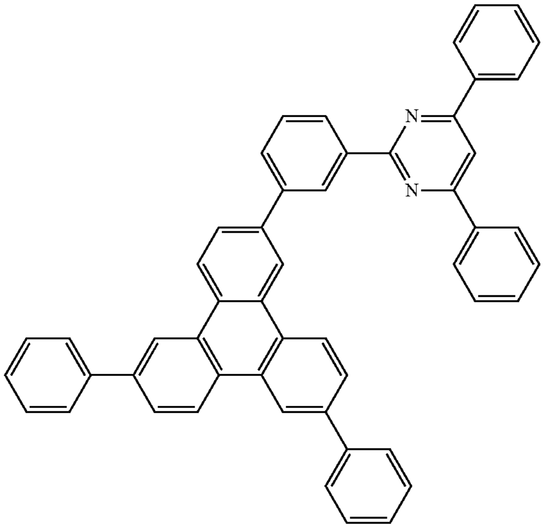
-continued
A-110
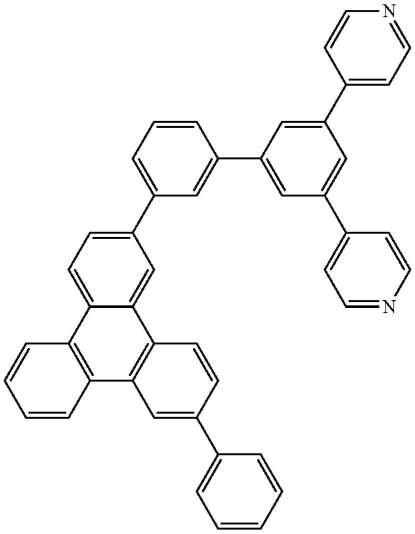
A-111
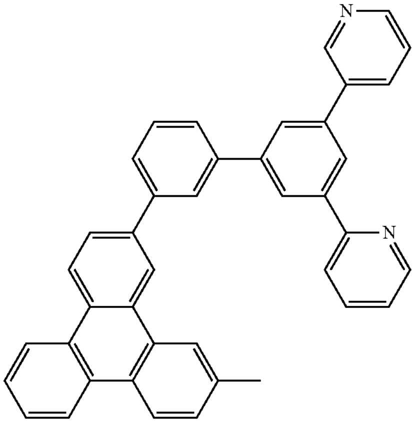
A-112
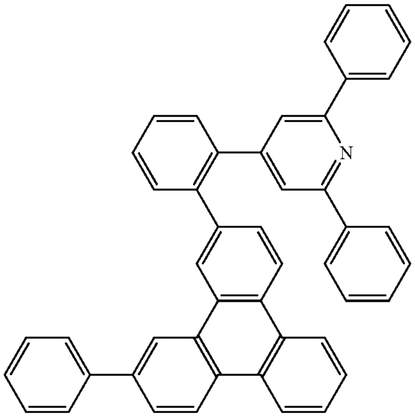

-continued
A-113
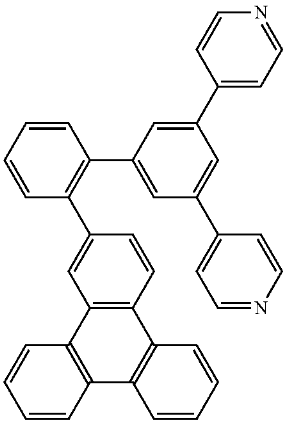
A-114
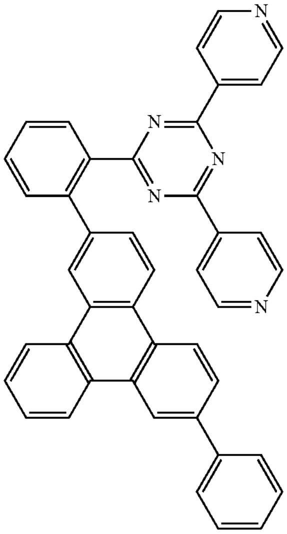
A-115
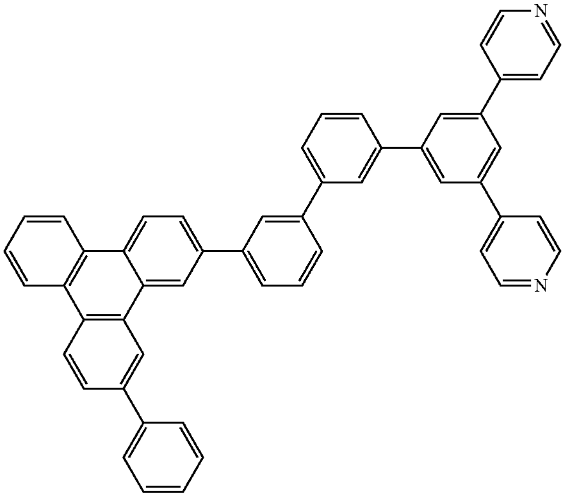
-continued
A-116
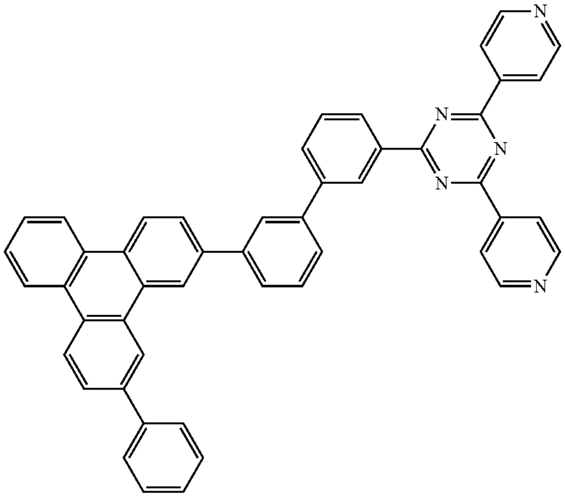
A-117
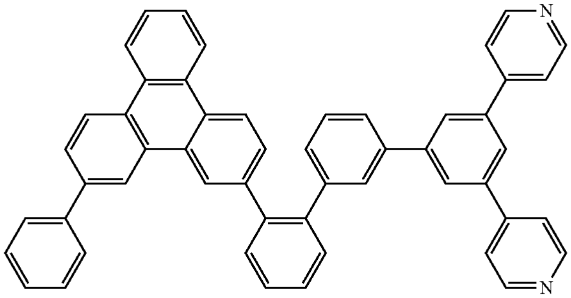
A-118
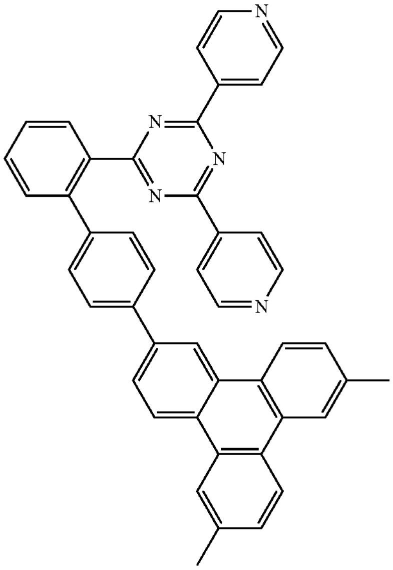

-continued
A-119
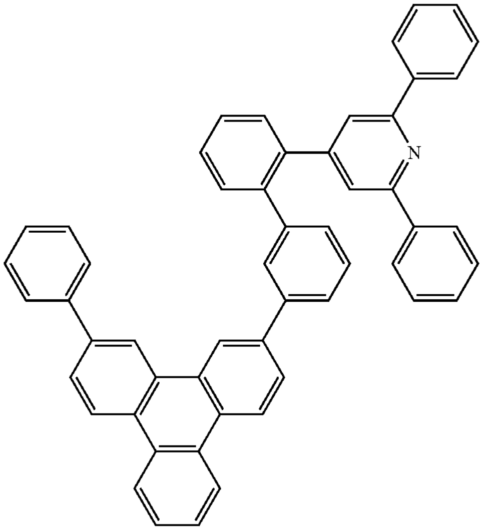
A-120
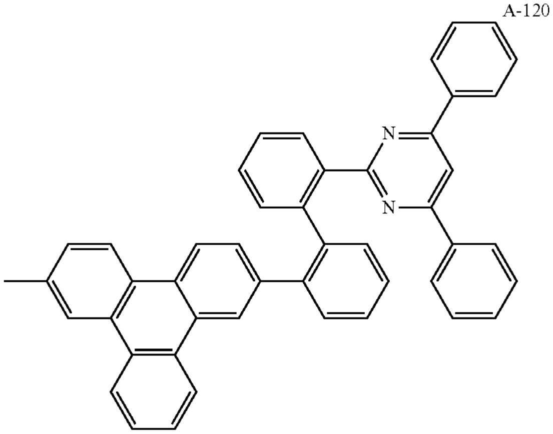
A-121
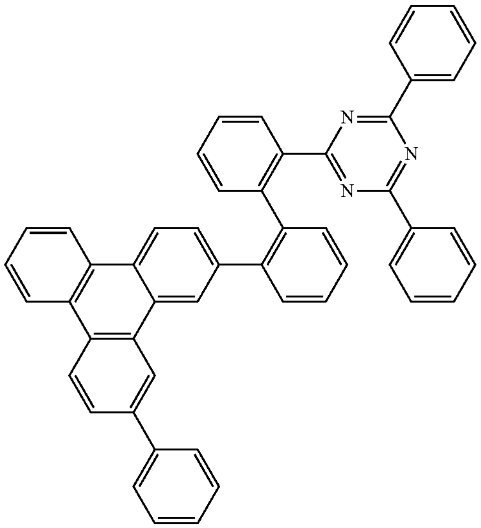
-continued
A-122
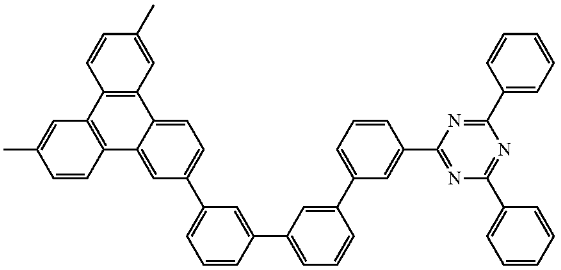
A-123
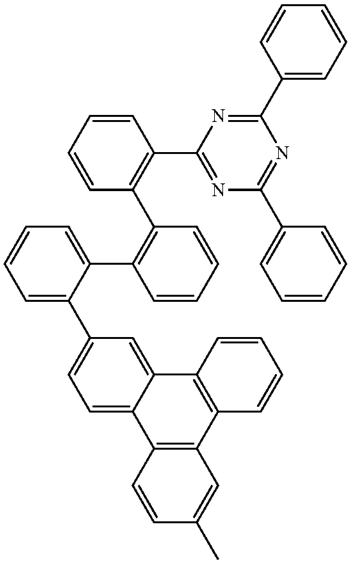
A-124
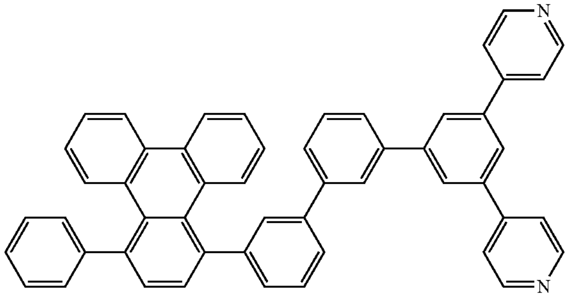
A-125
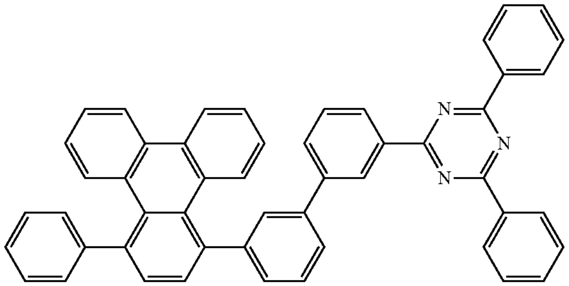
At least one or more kinds of the first host compound may be used.
The second host compound is represented by the following Chemical Formula 2.

[Chemical Formula 2]

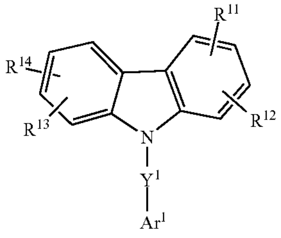

In the above Chemical Formula 2, $Y^1$ is a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof, $Ar^1$ is a substituted or unsubstituted C6 to C30 aryl group, a substituted or unsubstituted C2 to C30 heteroaryl group, or a combination thereof, $R^{11}$ to $R^{14}$ are independently hydrogen, deuterium, a substituted or unsubstituted C1 to C20 alkyl group, a substituted or unsubstituted C6 to C50 aryl group, a substituted or unsubstituted C2 to C50 heteroaryl group, or a combination thereof, and at least one of $R^{11}$ to $R^{14}$ and $Ar^1$ includes a substituted or unsubstituted triphenylene group or a substituted or unsubstituted carbazole group.

The second host compound is a compound having bipolar characteristics in which hole characteristics are relatively stronger than electron characteristics and thus, increases charge mobility and stability when used with the first host compound and resultantly, may improve luminous efficiency and life-span characteristics.

The second host compound may be, for example represented by at least one of the following Chemical Formulae 2-I to 2-III.

[Chemical Formula 2-I]

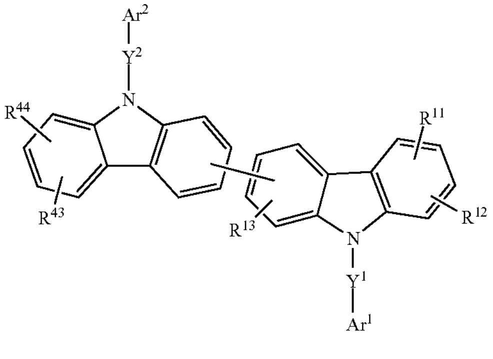

-continued

[Chemical Formula 2-II]

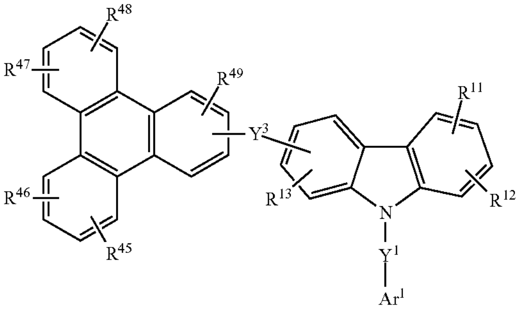

[Chemical Formula 2-III]

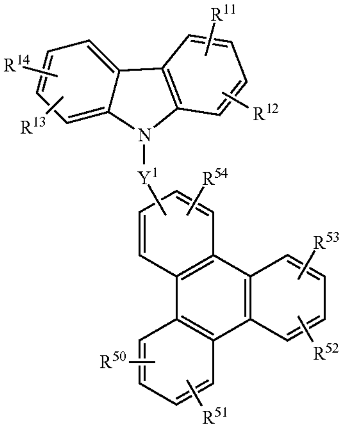

In the above Chemical Formulae 2-I to 2-III, $Y^1$ to $Y^3$ are independently a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof, $Ar^1$ and $Ar^2$ are independently a substituted or unsubstituted C6 to C30 aryl group, a substituted or unsubstituted C2 to C30 heteroaryl group, or a combination thereof, and $R^{11}$ to $R^{14}$ and $R^{43}$ to $R^{54}$ are independently hydrogen, deuterium, a substituted or unsubstituted C1 to C20 alkyl group, a substituted or unsubstituted C6 to C50 aryl group, a substituted or unsubstituted C2 to C50 heteroaryl group, or a combination thereof.

The second host compound represented by the above Chemical Formula 2-I has a structure where two carbazole groups having a substituent are linked to each other.

$Ar^1$ and $Ar^2$ of the above Chemical Formula 2-I are a substituent having electron or hole characteristics, and may be, for example a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted carbazolyl group, a substituted or unsubstituted benzofuranyl group, a substituted or unsubstituted benzothiophenyl group, a substituted or unsubstituted fluorenyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted triphenylene group, a substituted or unsubstituted dibenzofuranyl group, a substituted or unsubstituted dibenzothiopheneyl group, or a combination thereof.

At least one of $Ar^1$ and $Ar^2$ of the above Chemical Formula 2-1 may be, for example a substituent having electron characteristics, and may be, for example a substituent represented by the following Chemical Formula A.

[Chemical Formula A]

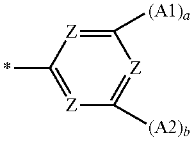

In the above Chemical Formula A,

Z is independently N or $CR^b$,

A1 and A2 are independently a substituted or unsubstituted C6 to C30 aryl group, a substituted or unsubstituted C3 to C30 heteroaryl group, or a combination thereof, at least one of the Z, A1 and A2 includes N, and a and b are independently 0 or 1.

The substituent represented by the above Chemical Formula A may be, for example a functional group listed in the following Group 3.

[Group 3]

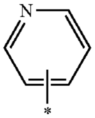
,
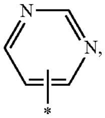
,
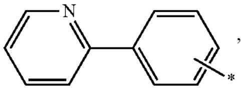
,
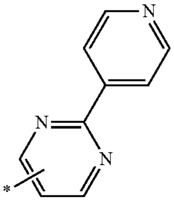
,
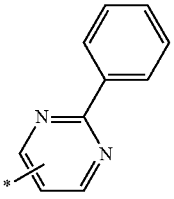
,
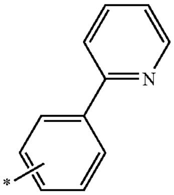
,
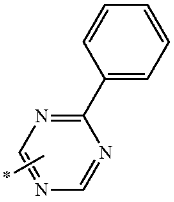
,
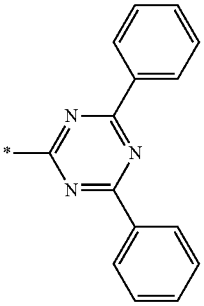
,
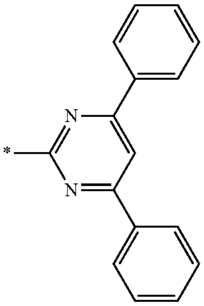
, -continued

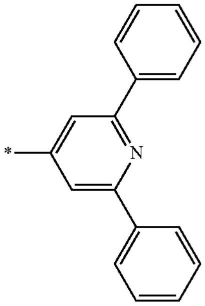
,
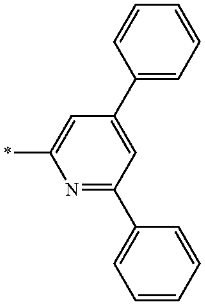
,
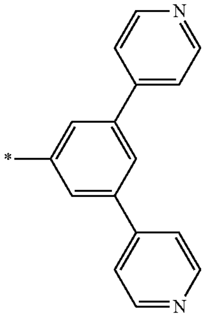
,
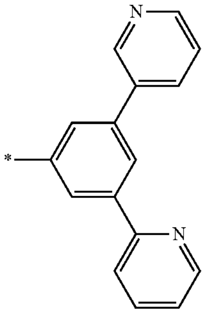
,
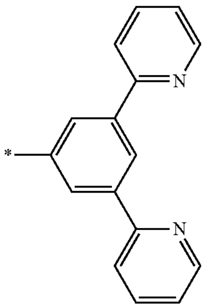
,
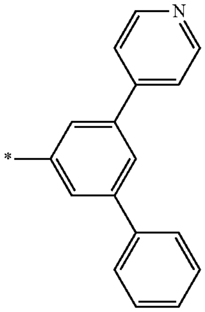
,
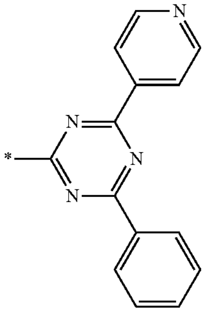
,
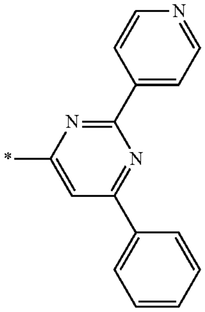
,
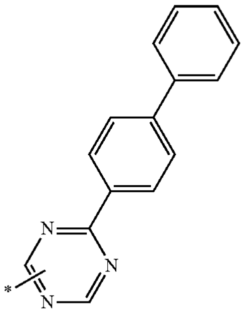

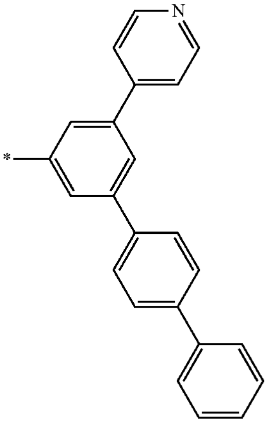
,

-continued
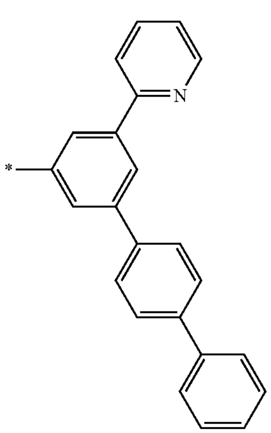
,
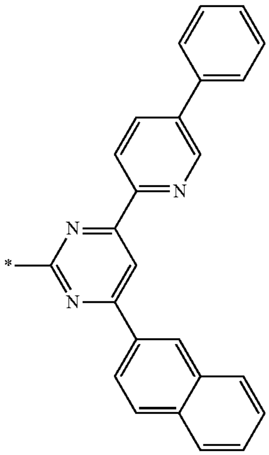
,
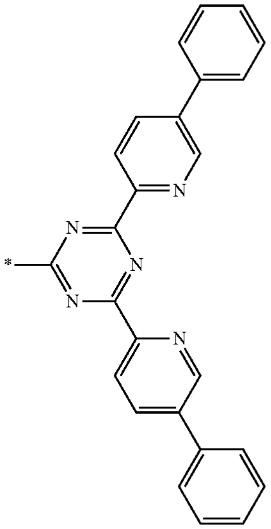
,
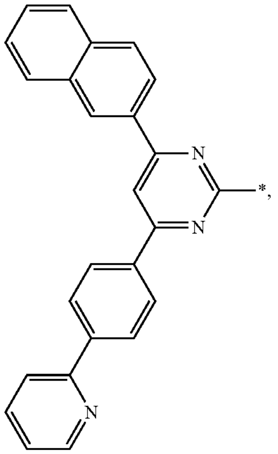
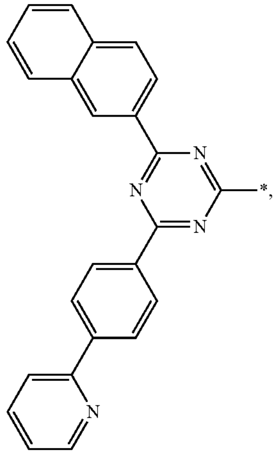
In addition, at least one of $Ar^1$ and $Ar^2$ of the above Chemical Formula 2-I may be, for example a substituent having hole characteristics, and may be, for example substituents listed in the following Group 4.
[Group 4]
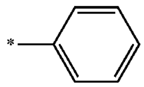
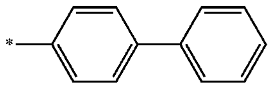
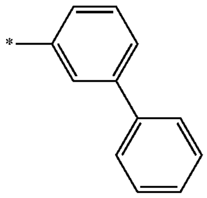
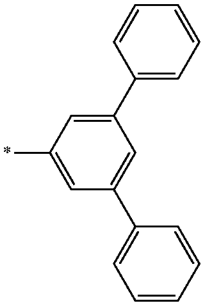
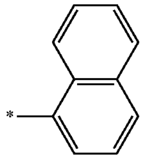
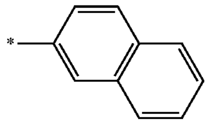
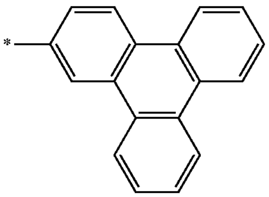
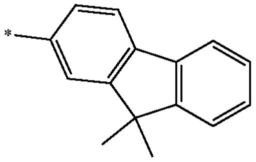
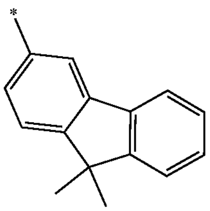
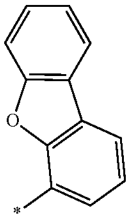
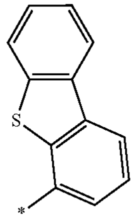
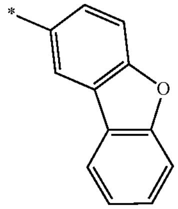
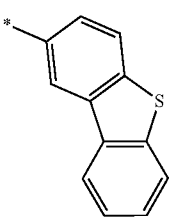
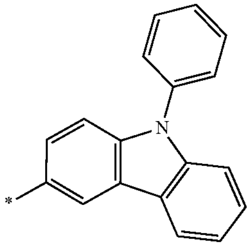
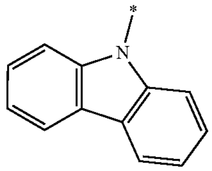

The compound represented by the above Chemical Formula 2-I may be, for example compounds selected from compounds listed in the following Group 5, but is not limited thereto.
[Group 5]
B-10
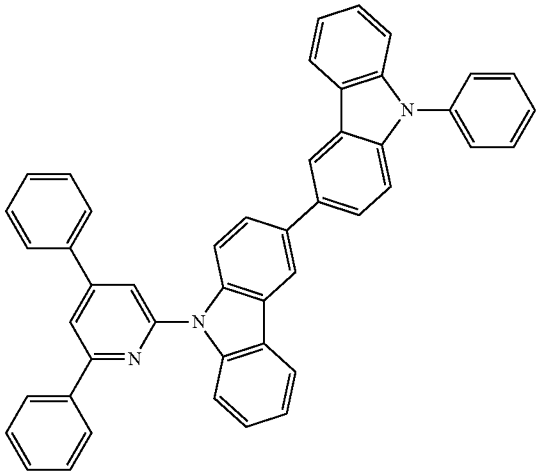
B-11
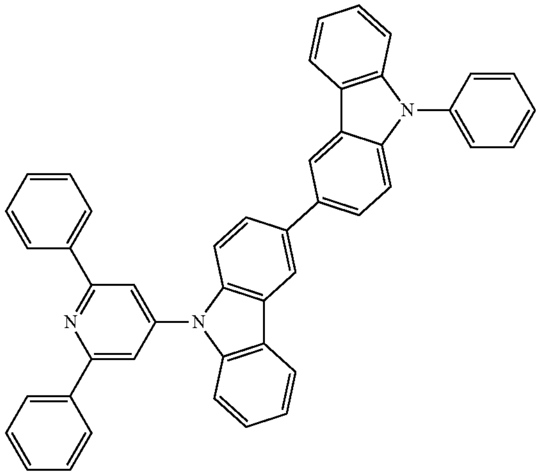
B-12
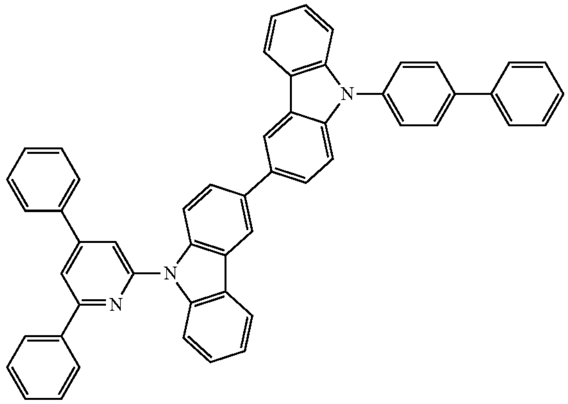
-continued
B-13
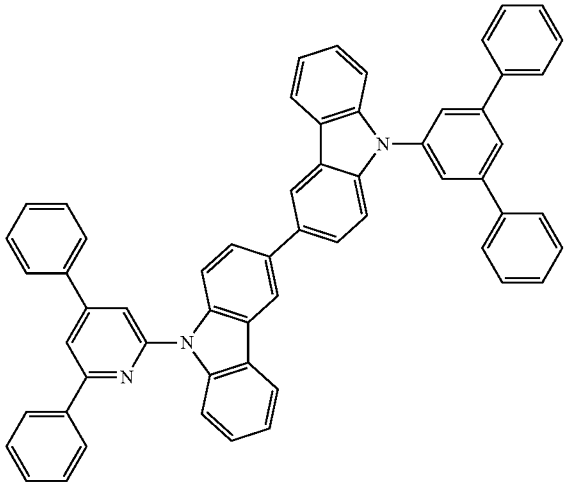
B-14
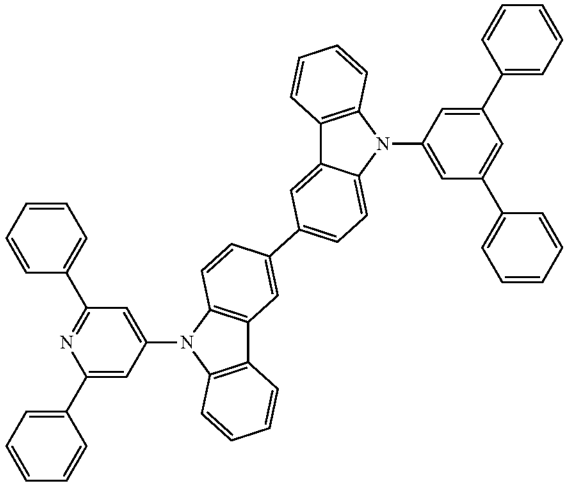
B-15
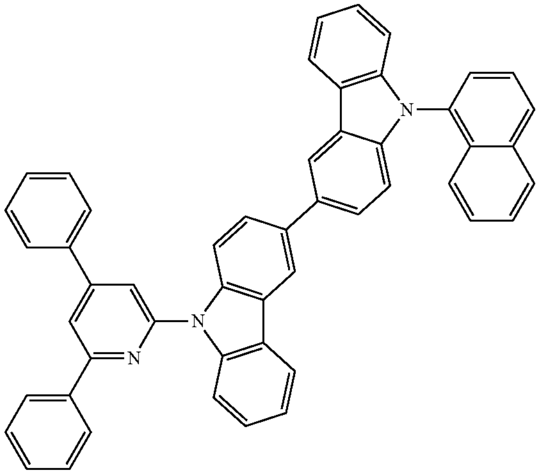

-continued
B-16
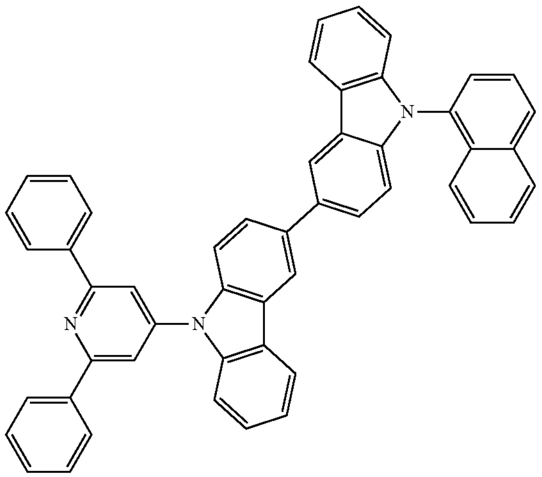
B-17
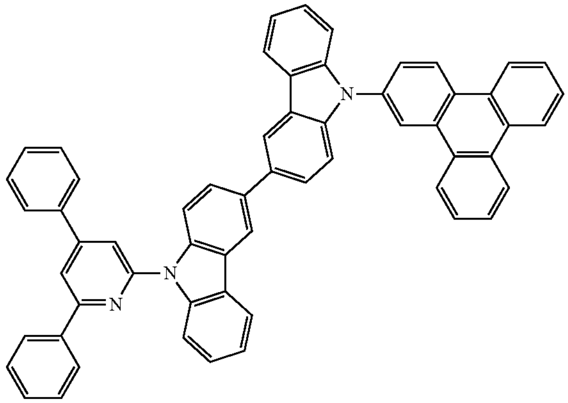
B-18
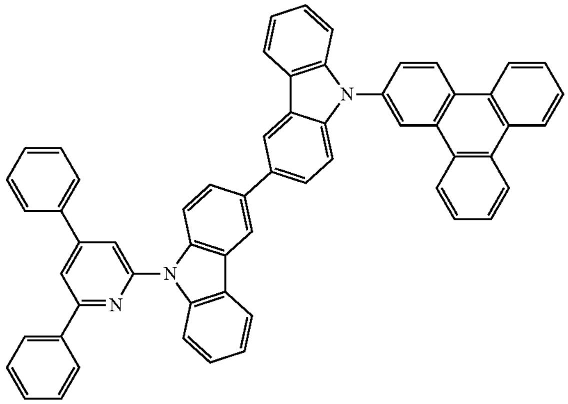
-continued
B-19
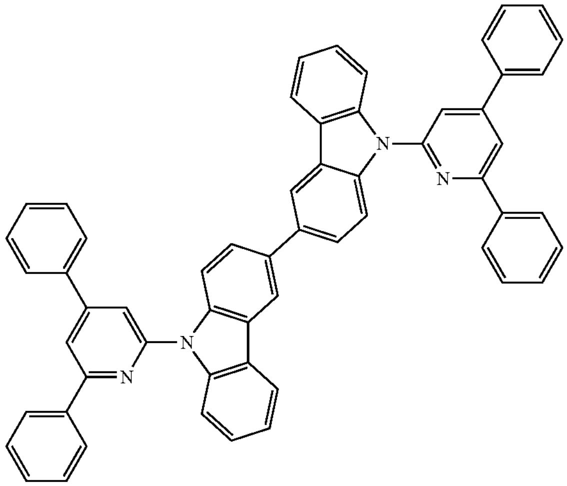
B-20
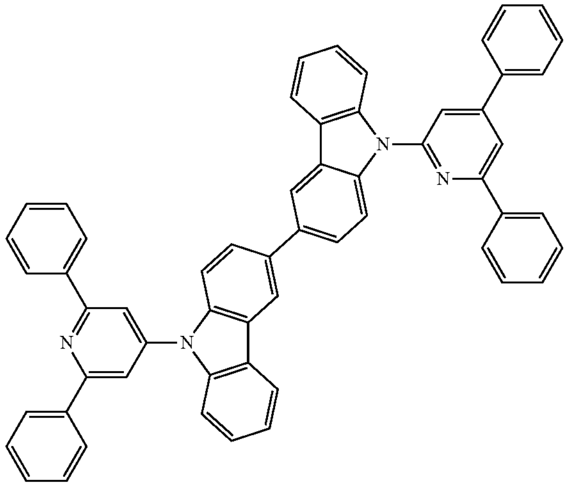
B-21
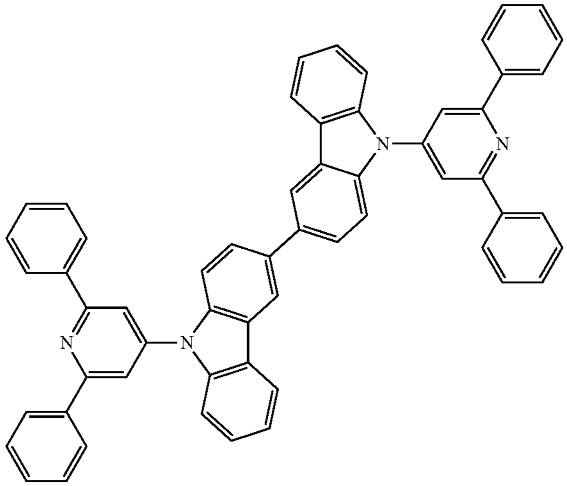

-continued
B-22
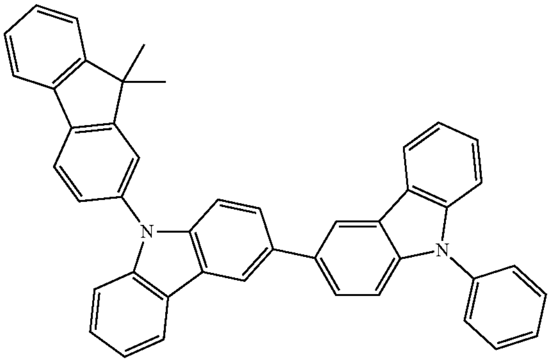
B-23
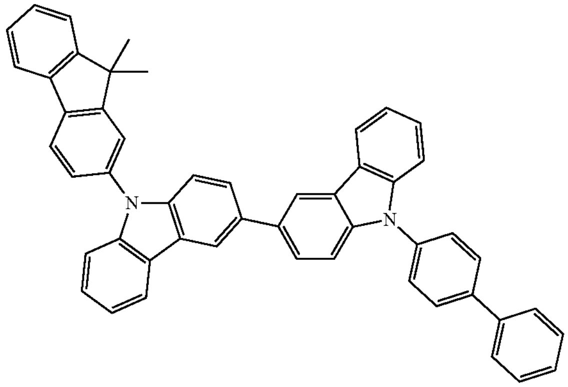
B-24
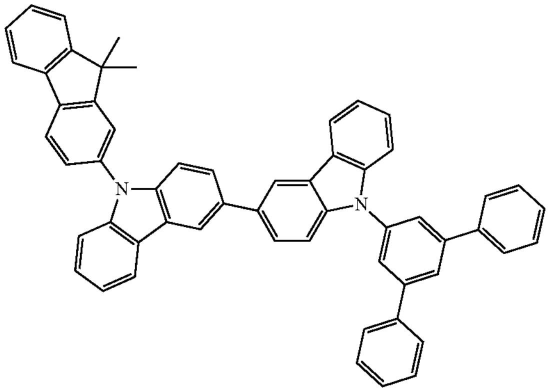
B-25
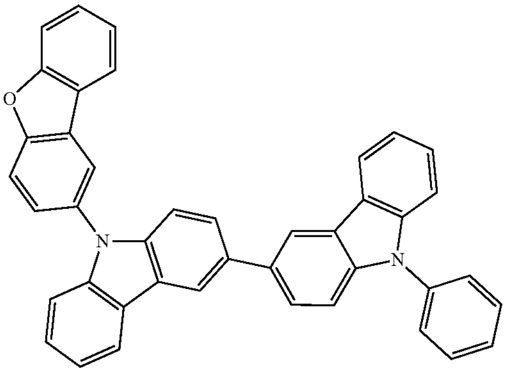
-continued
B-26
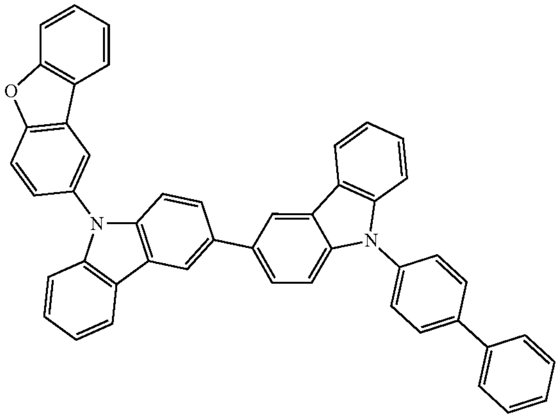
B-27
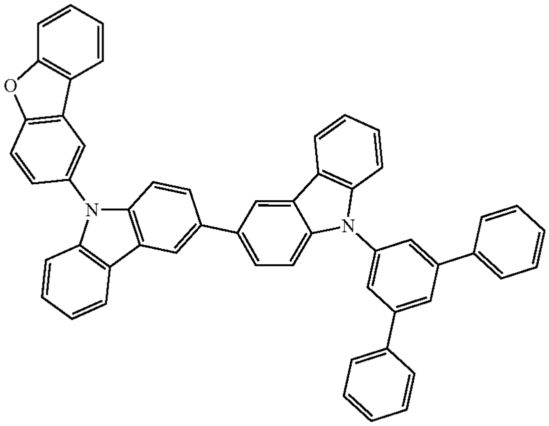
B-28
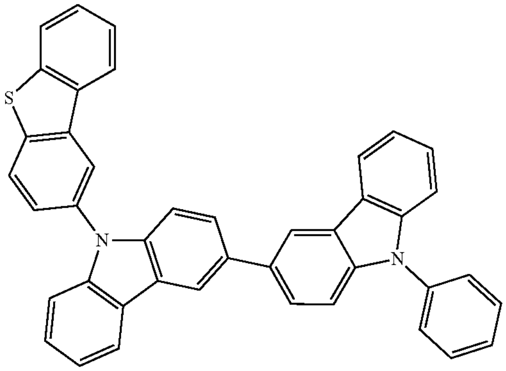

-continued
B-29
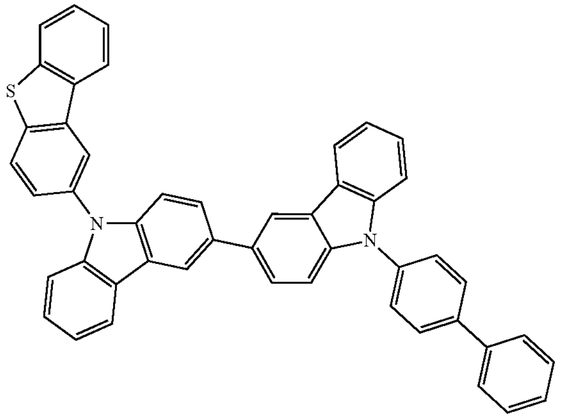
B-30
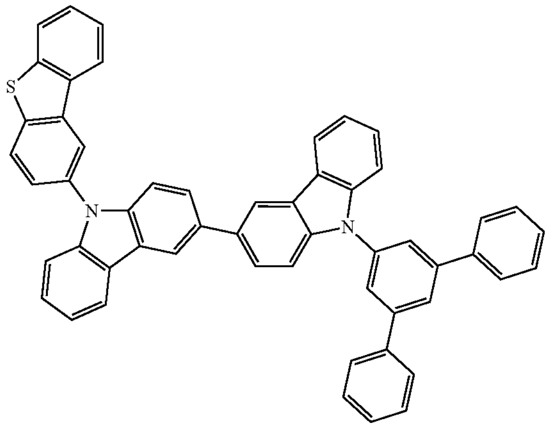
B-31
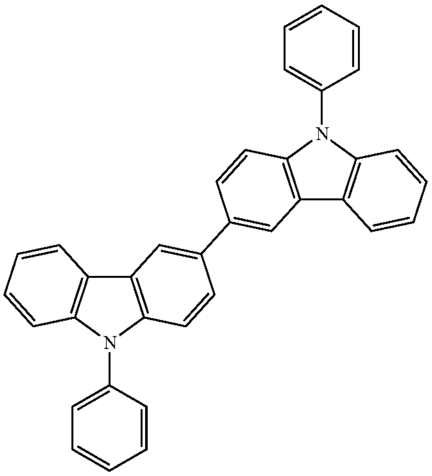
-continued
B-32
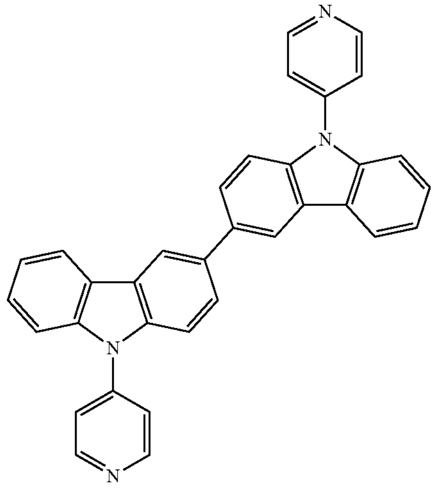
B-33
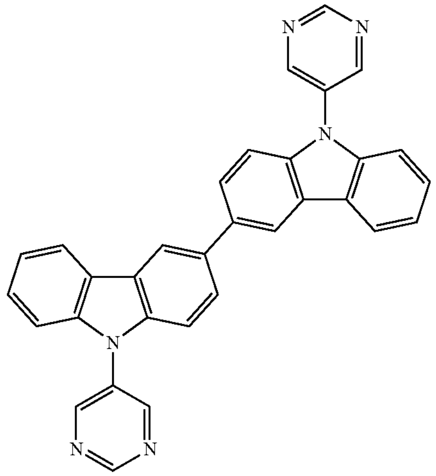
B-34
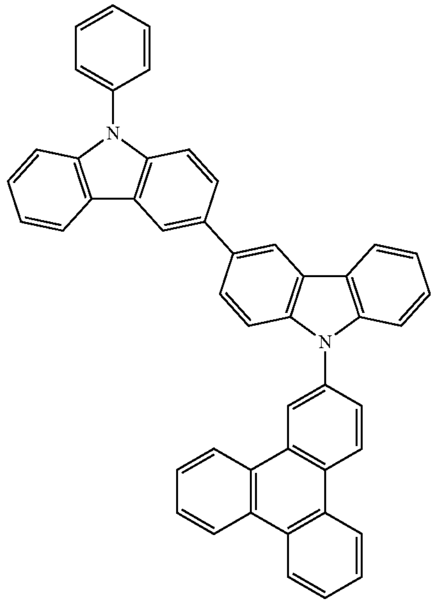

-continued
B-35
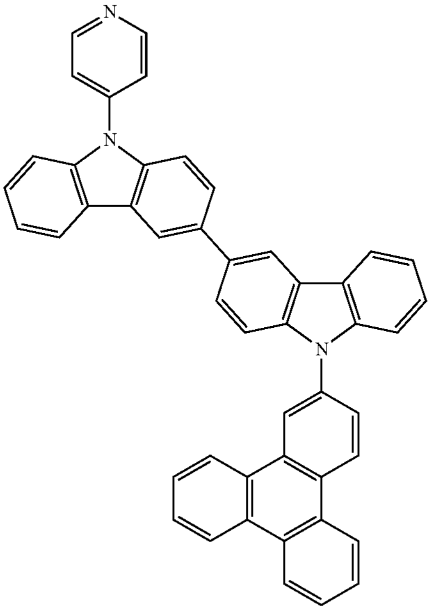
B-37
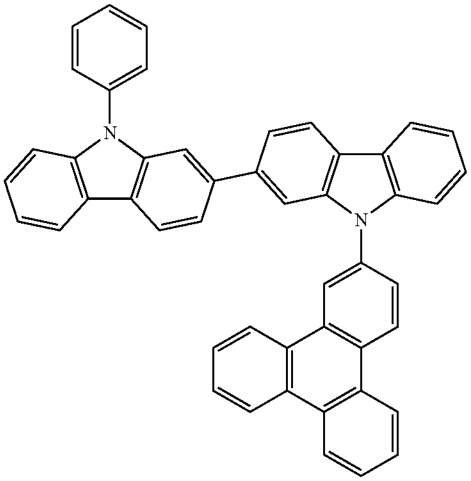
B-38
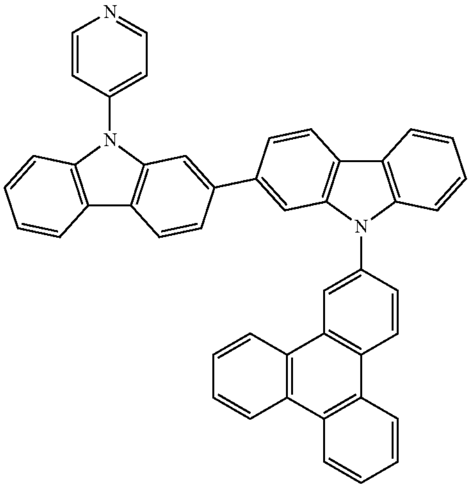
-continued
B-40
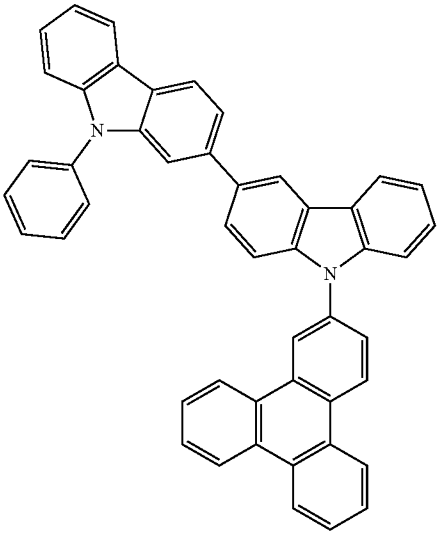
B-41
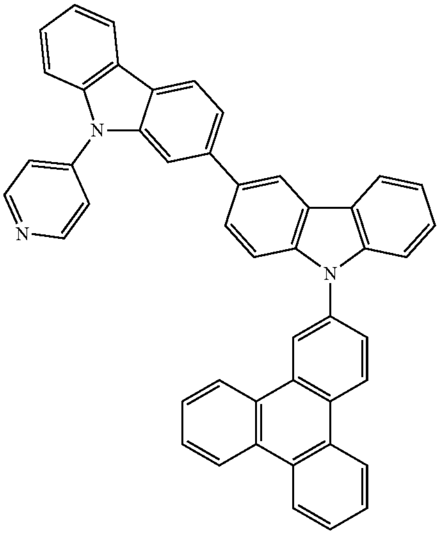

-continued
B-43
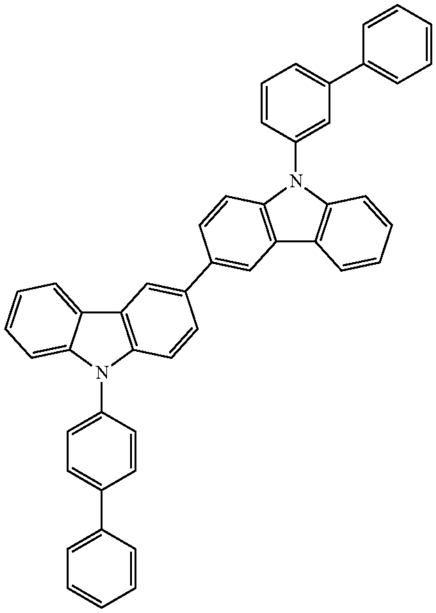
B-44
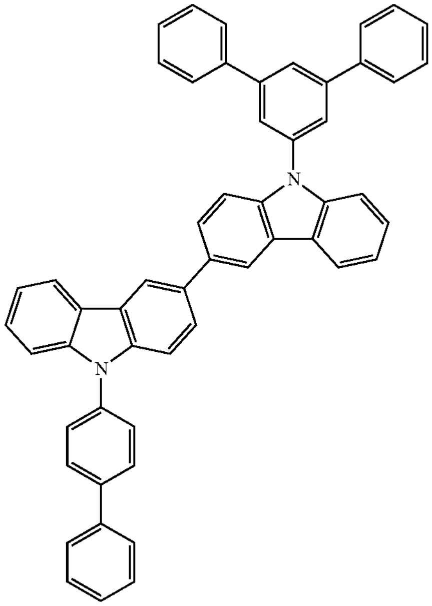
-continued
B-45
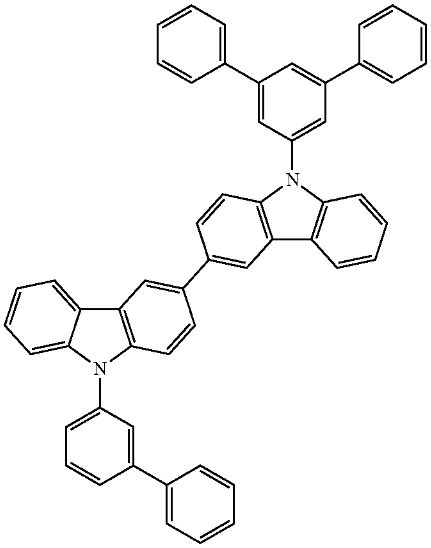
B-46
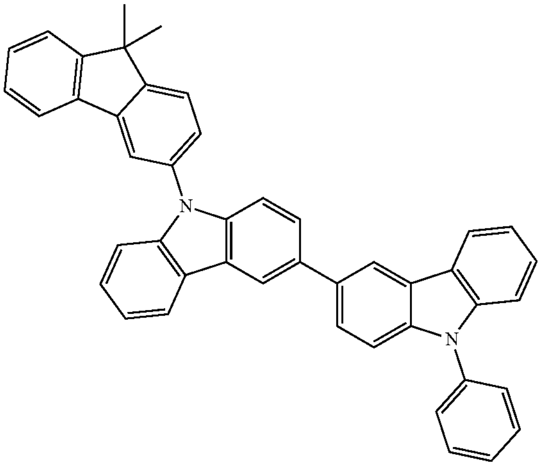
B-47
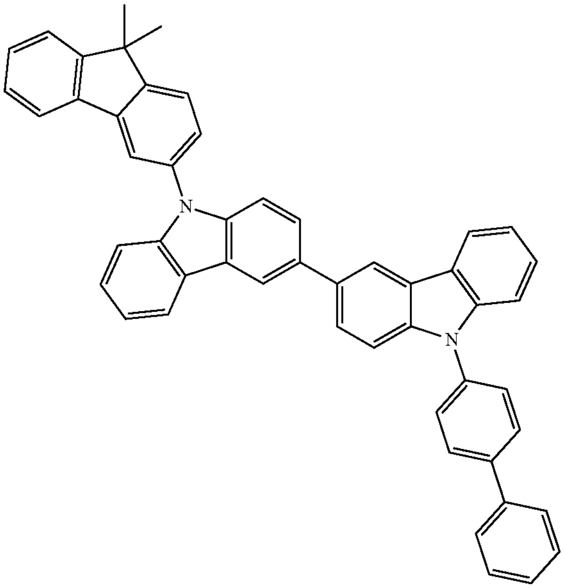

-continued
B-48
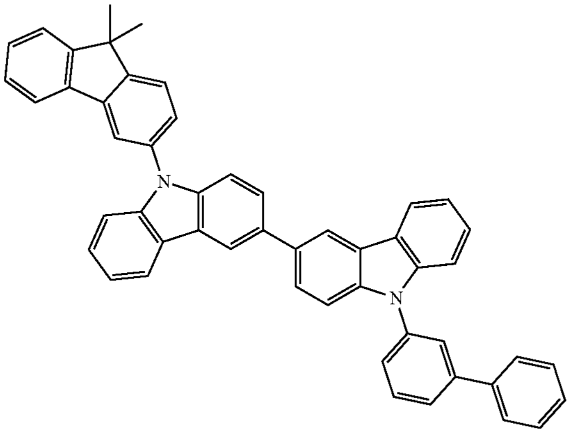
B-49
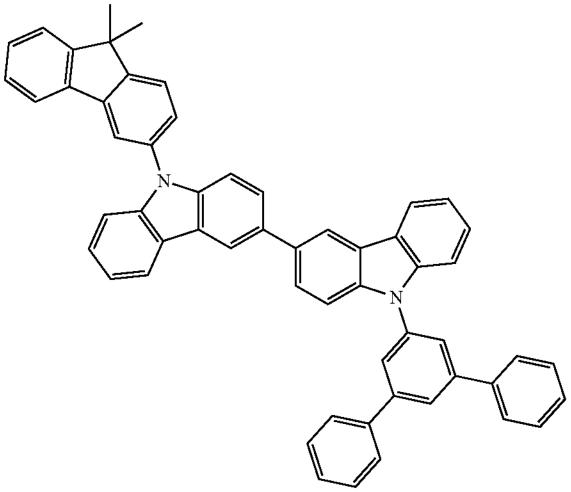
B-50
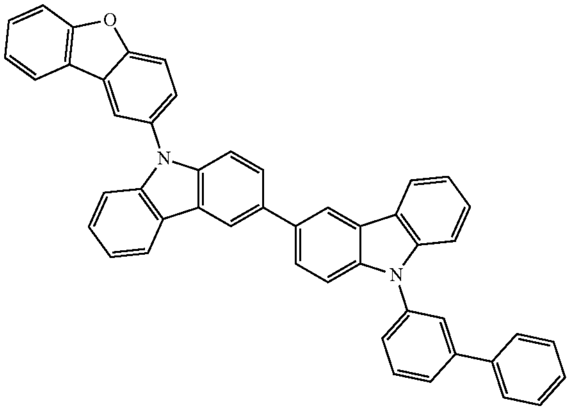
-continued
B-51
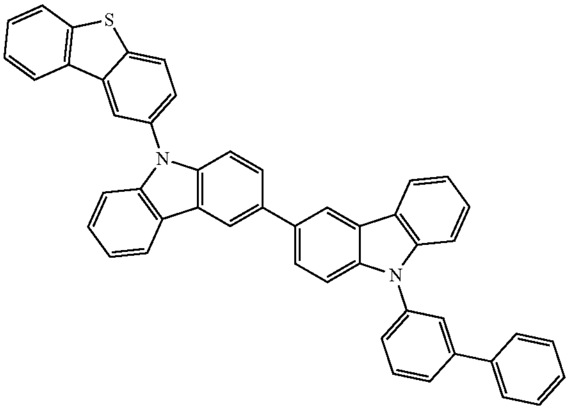
B-52
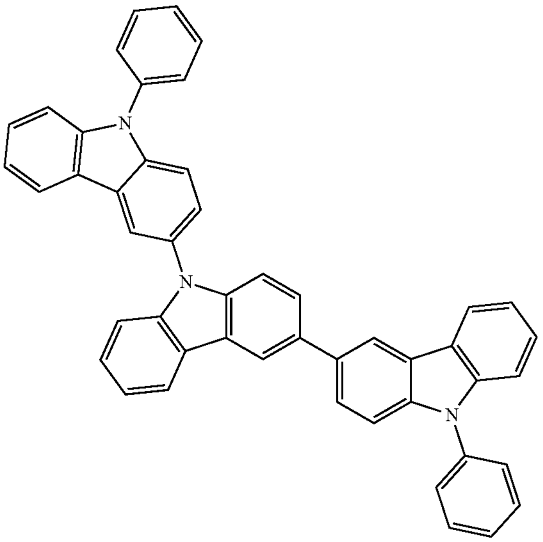
B-53
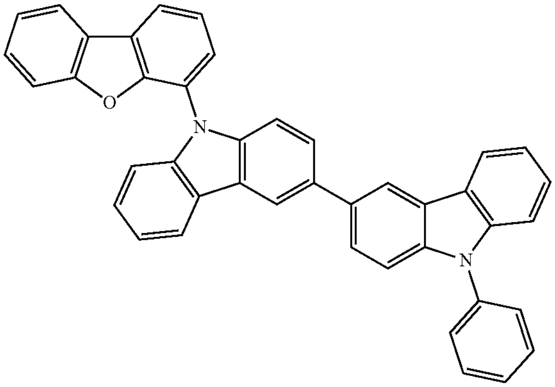

-continued
B-54
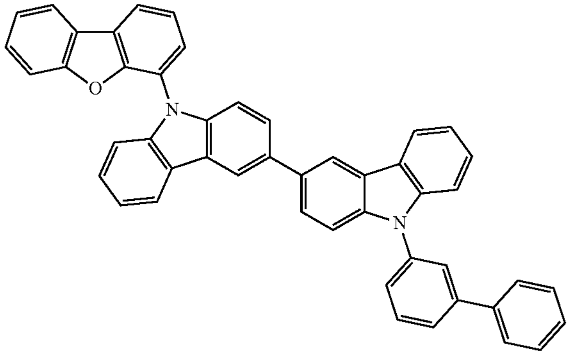
B-55
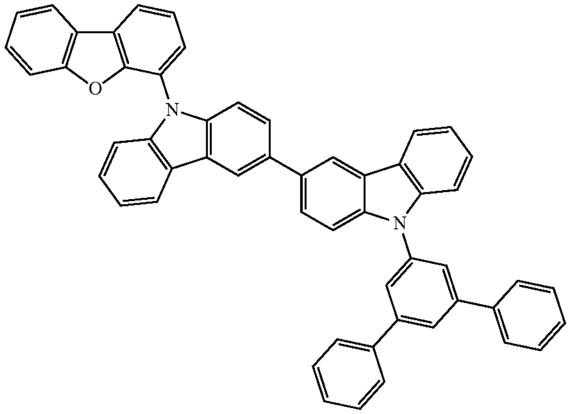
B-56
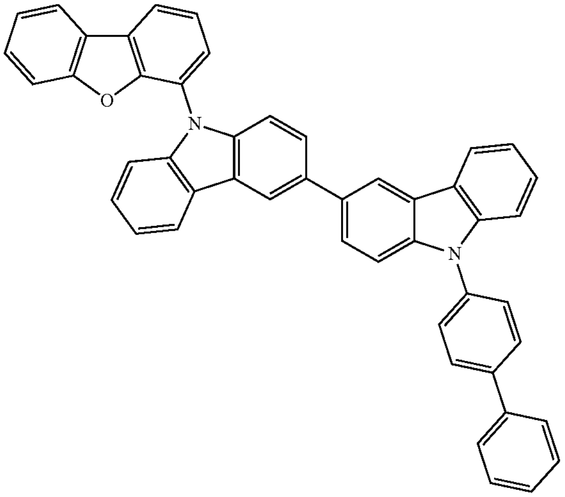
-continued
B-57
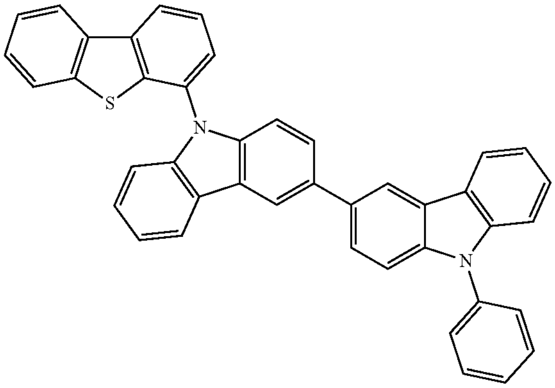
B-58
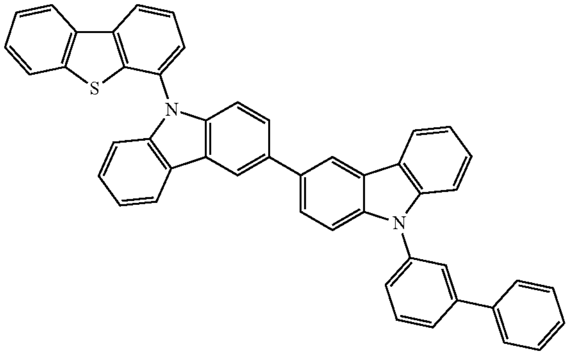
B-59
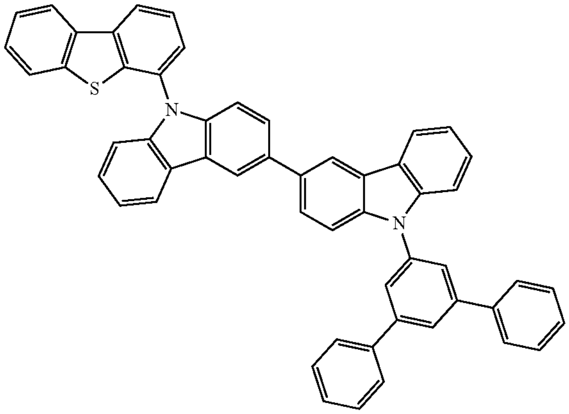

-continued
B-60
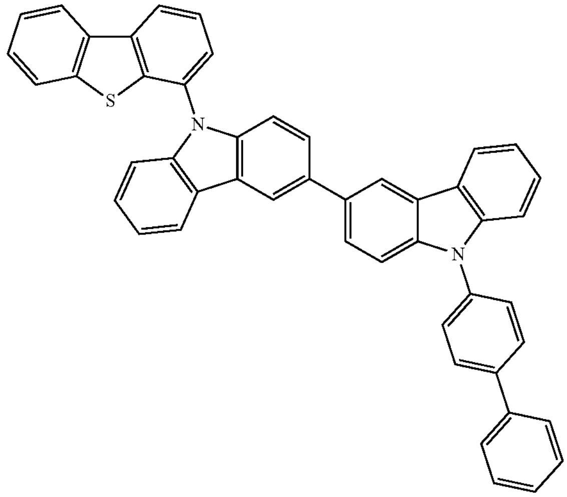
B-61
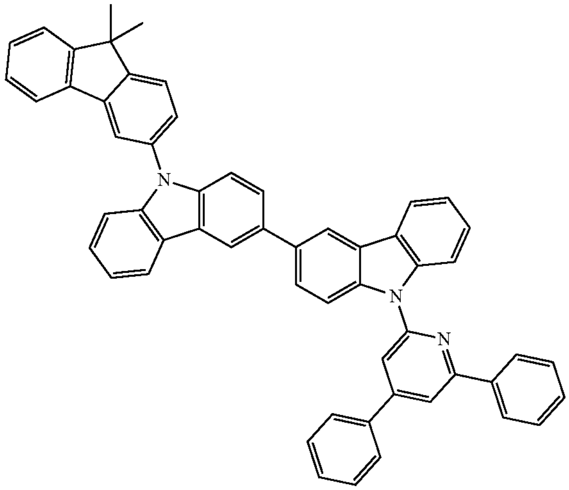
B-62
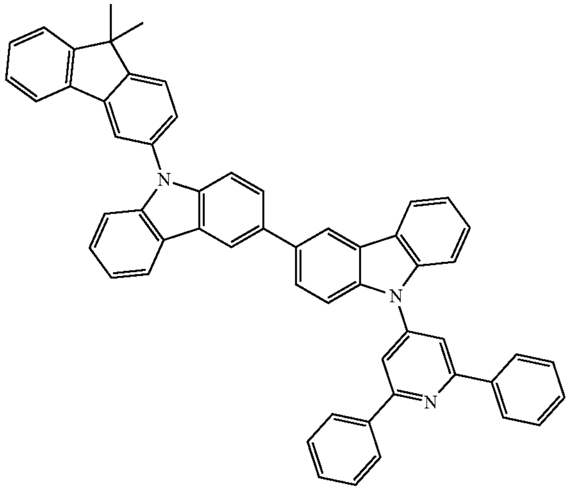
-continued
B-63
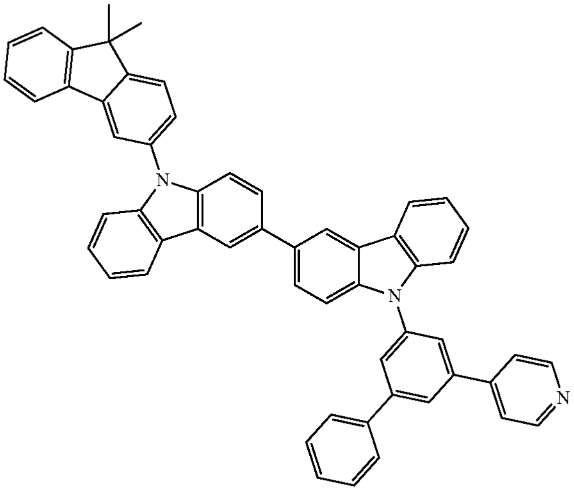
B-64
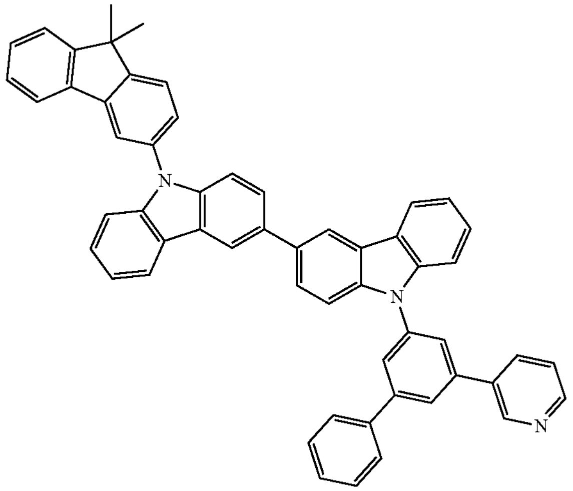
B-65
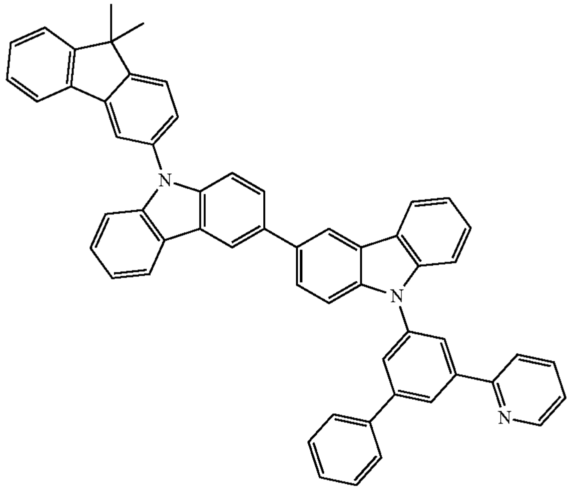

-continued
B-66
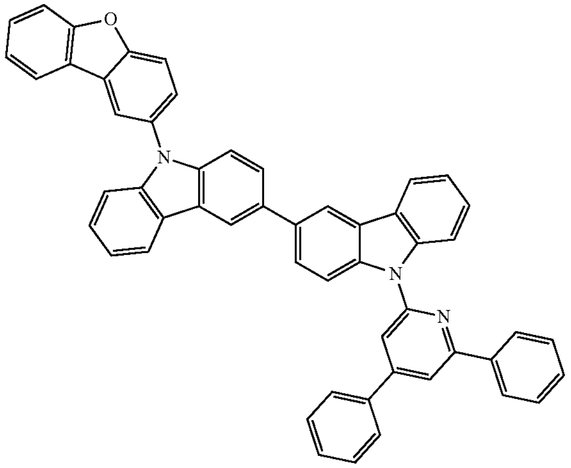
B-67
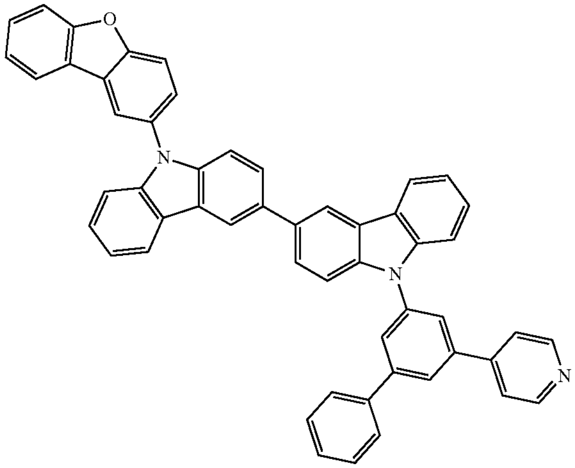
B-68
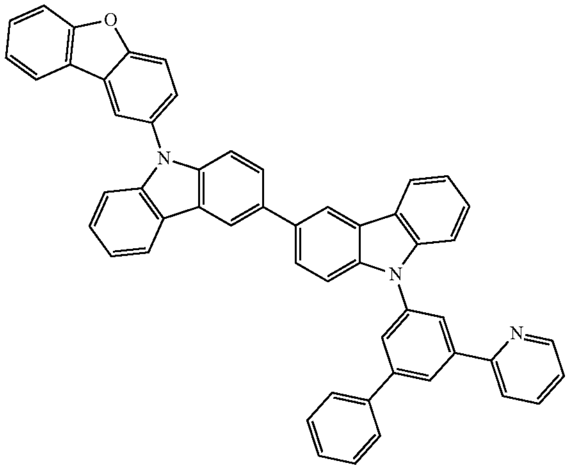
-continued
B-69
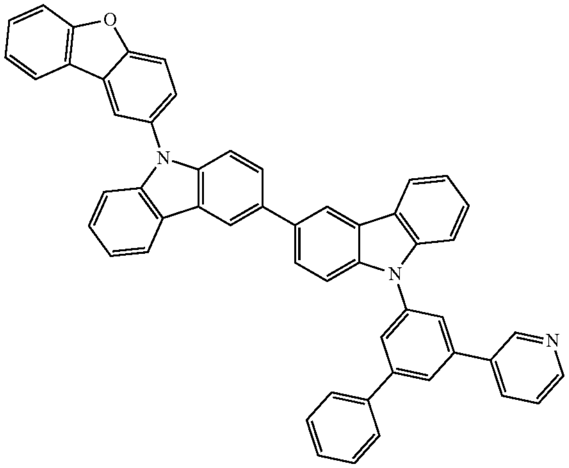
B-70
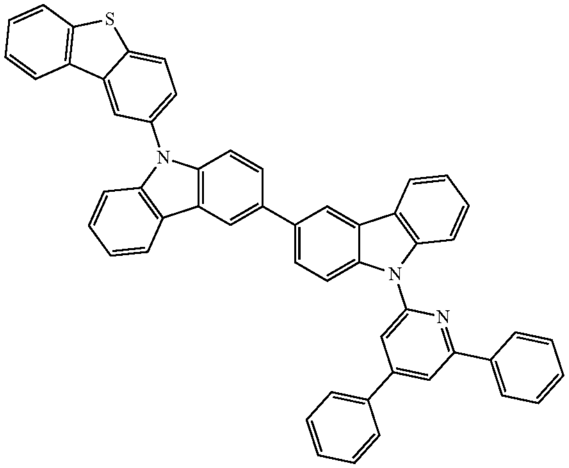
B-71
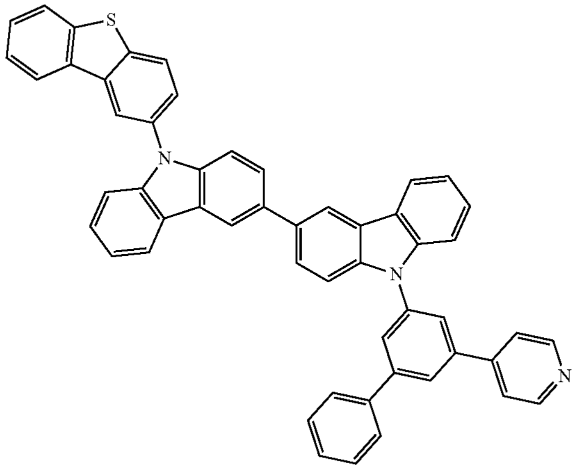

-continued
B-72
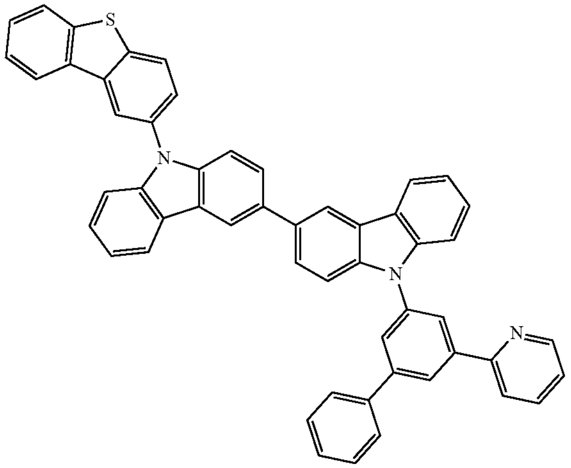
B-73
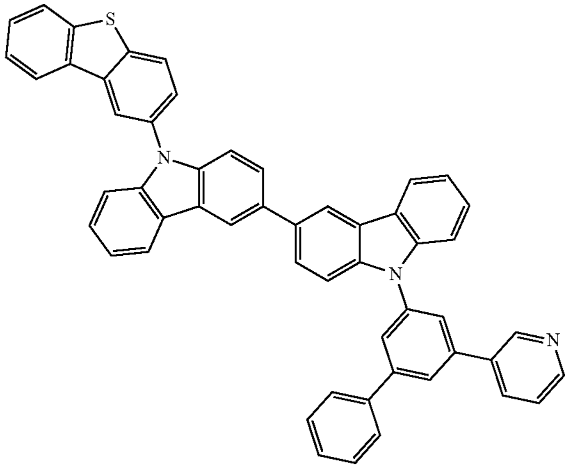
B-74
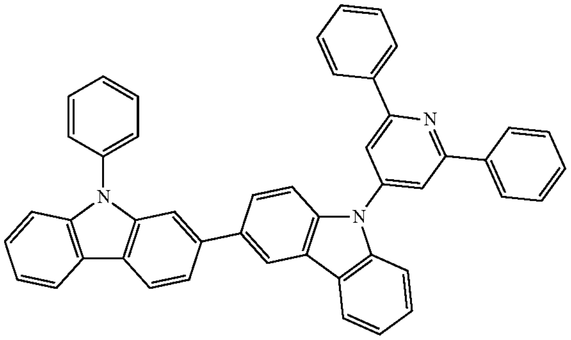
-continued
B-75
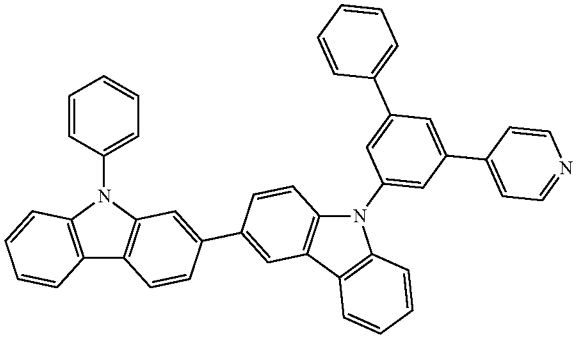
B-76
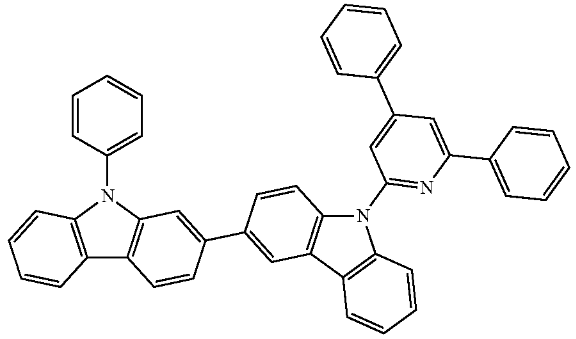
B-77
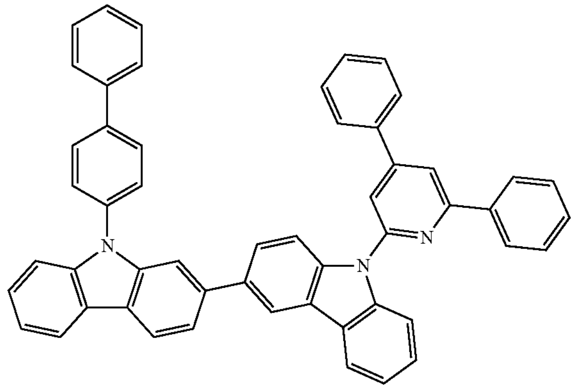
B-78
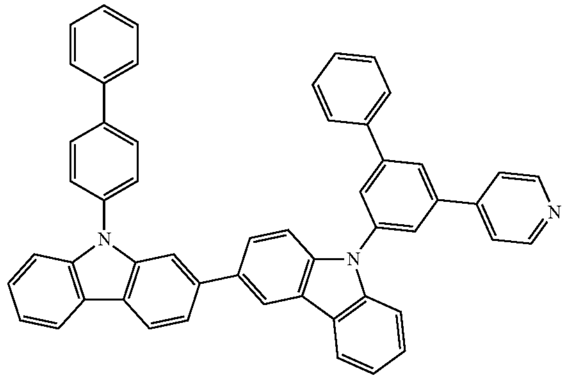

-continued
B-79
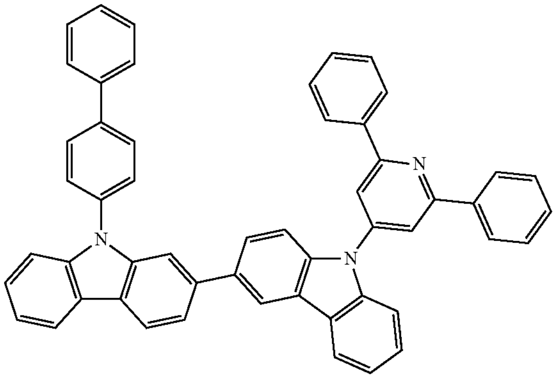
B-80
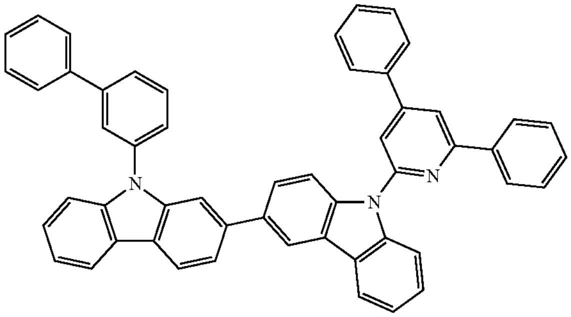
B-81
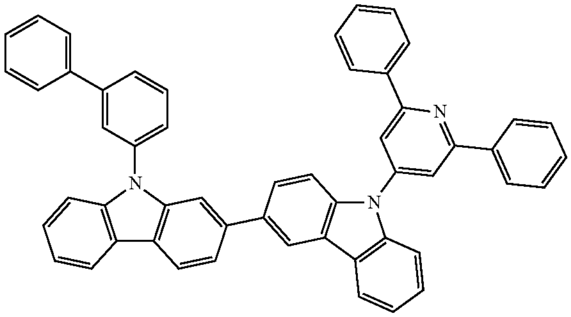
B-82
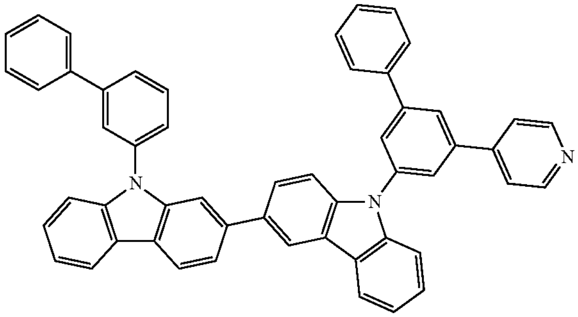
-continued
B-83
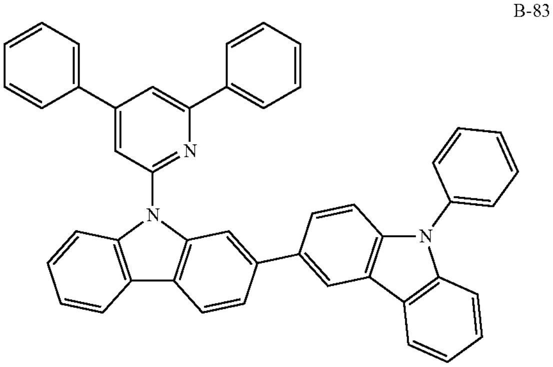
B-84
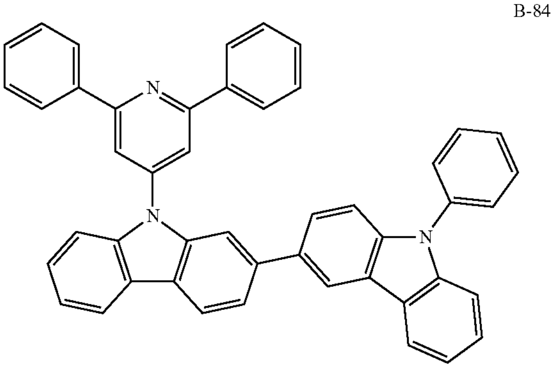
B-85
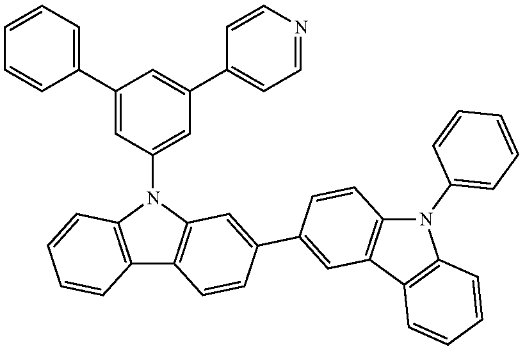
B-86
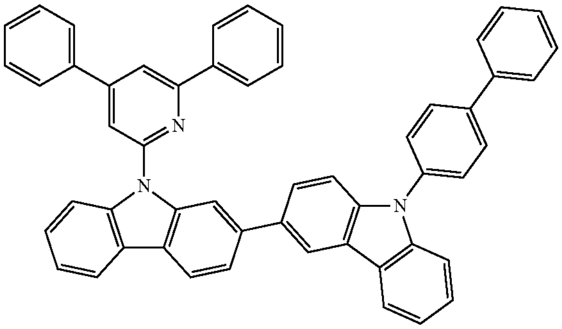

-continued
B-87
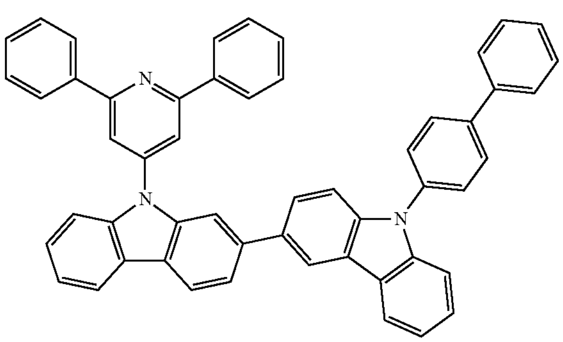
B-88
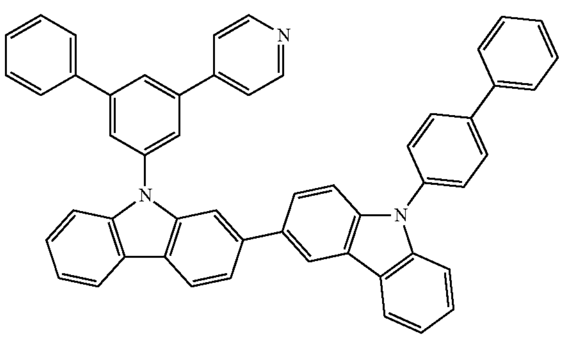
B-89
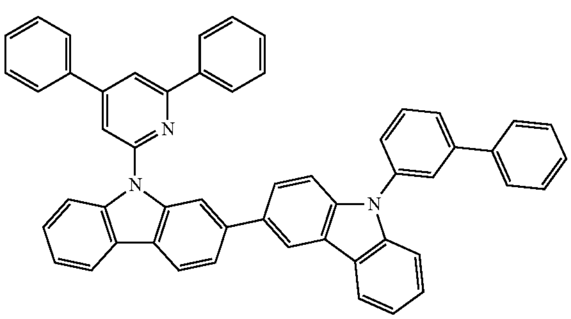
B-90
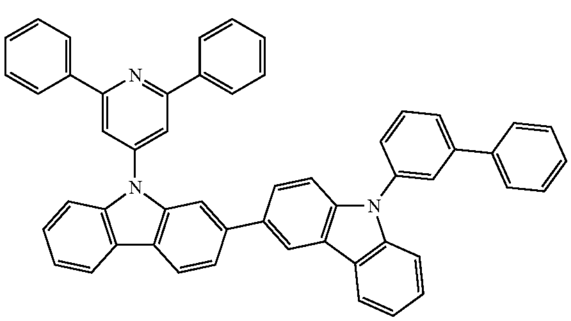
-continued
B-91
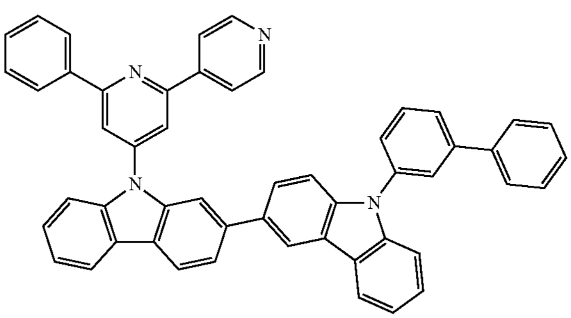
B-92
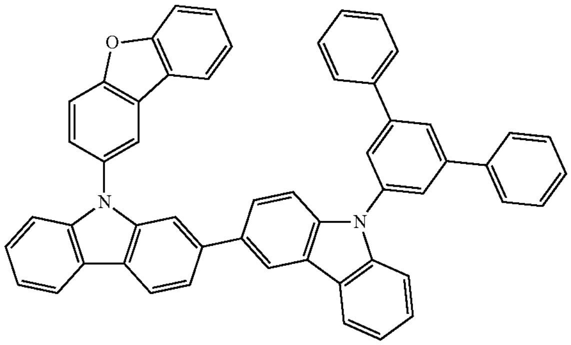
B-93
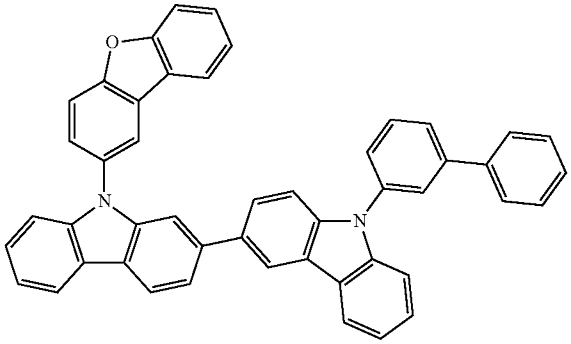
B-94
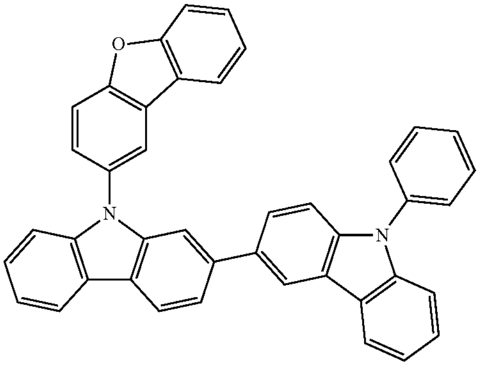

-continued
B-95
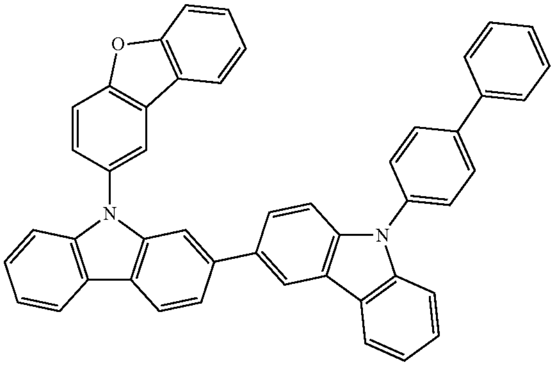
B-96
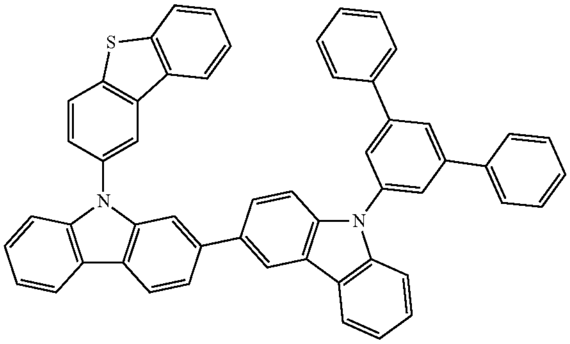
B-97
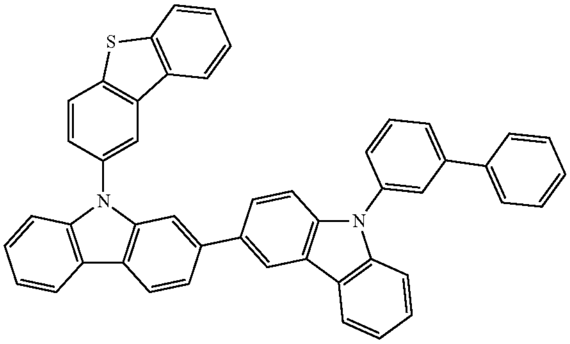
B-98
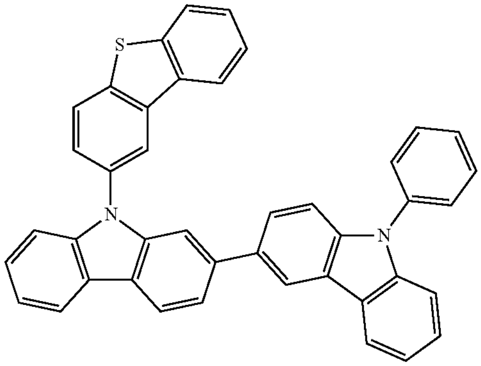
-continued
B-99
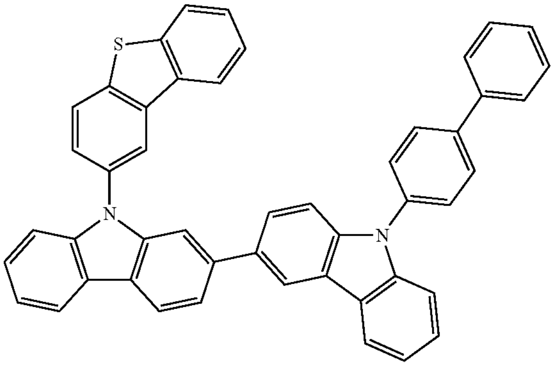
B-100
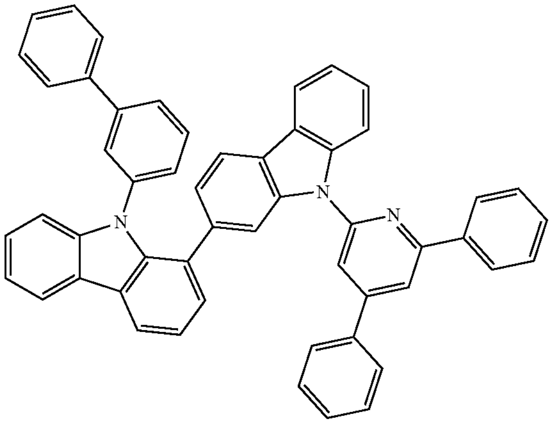
B-101
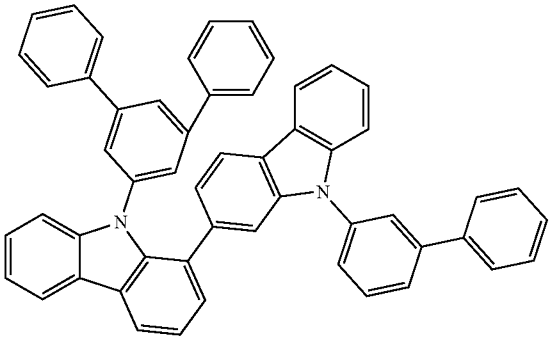
B-102
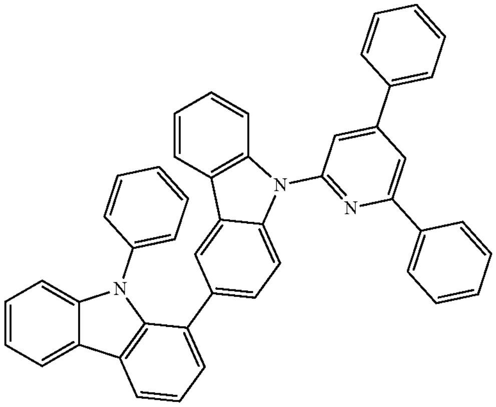

-continued
B-103
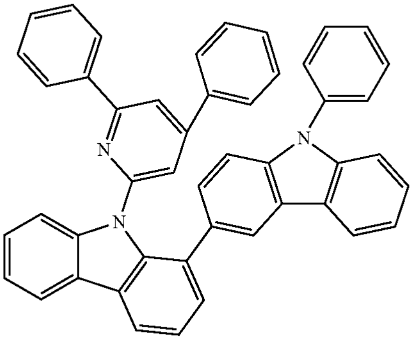
B-104
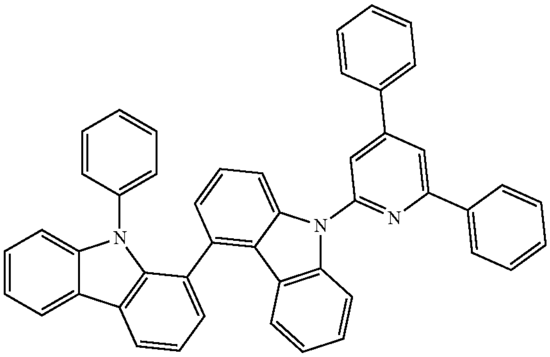
B-105
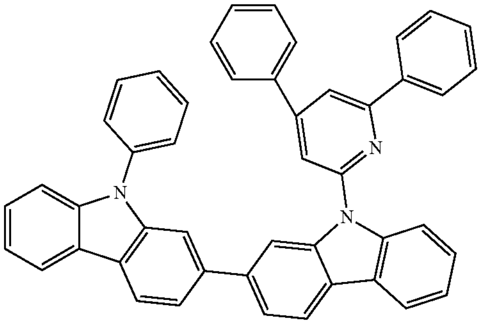
B-106
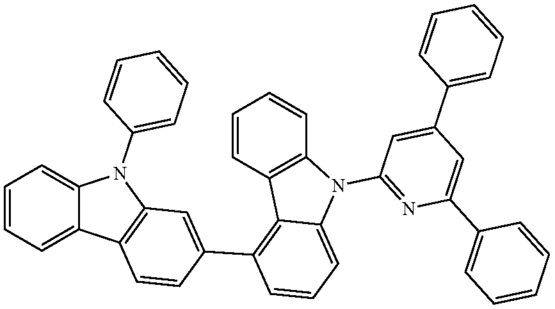
-continued
B-107
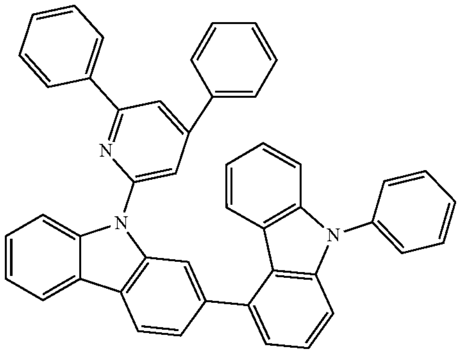
B-108
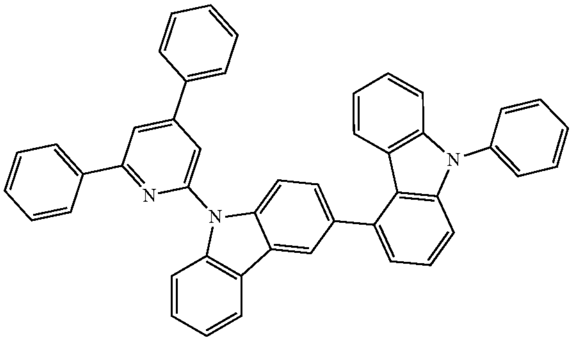
B-109
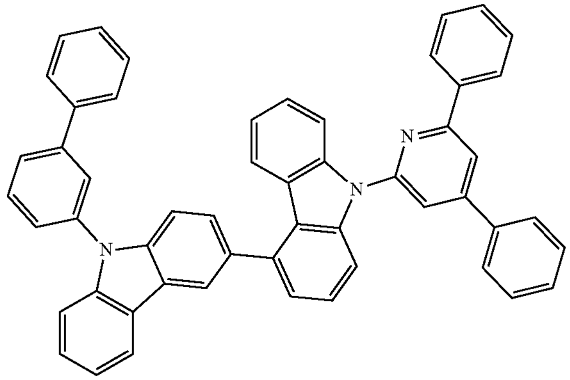
B-110
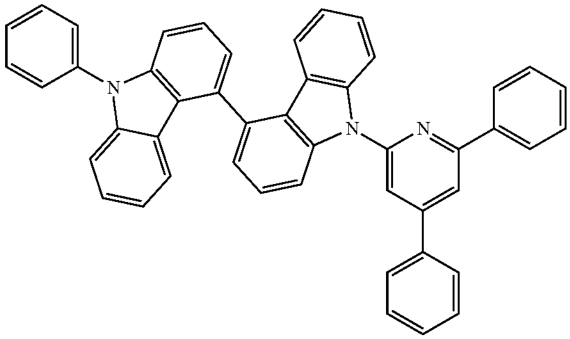

-continued

B-111

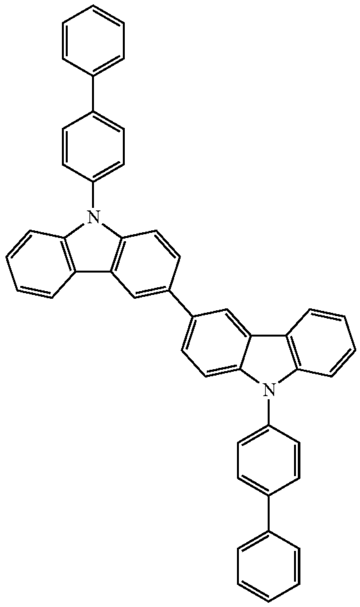

B-112

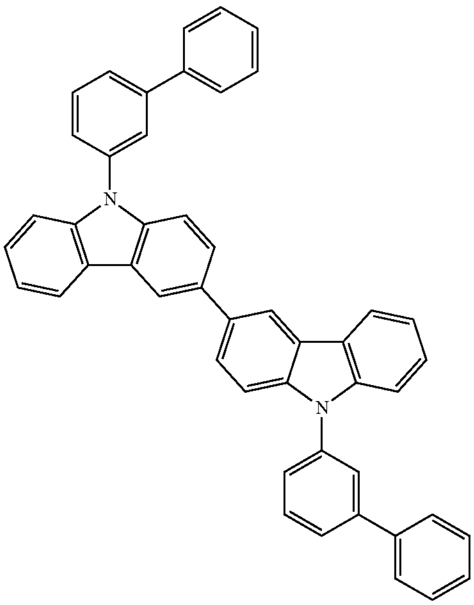

-continued

B-113

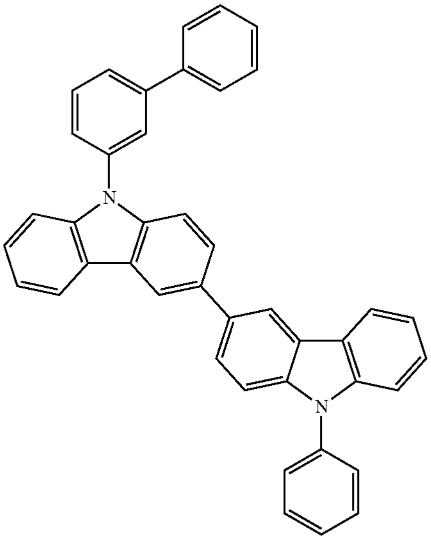

A compound represented by the above Chemical Formula 2-II or 2-III has a structure where a substituted or unsubstituted carbazole group and a substituted or unsubstituted triphenylene group are bonded.

The $Ar^1$ of the above Chemical Formula 2-II is a substituent having hole or electron characteristics, and may be, for example a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted carbazolyl group, a substituted or unsubstituted benzofuranyl group, a substituted or unsubstituted benzothiophenyl group, a substituted or unsubstituted fluorenyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted triphenylene group, a substituted or unsubstituted dibenzothiopheneyl group, a substituted or unsubstituted dibenzofuranyl group, or a combination thereof.

The compound represented by the above Chemical Formula 2-II may be, for example compounds selected from compounds listed in the following Group 6, but is not limited thereto.

[Group 6]

-continued
C-10
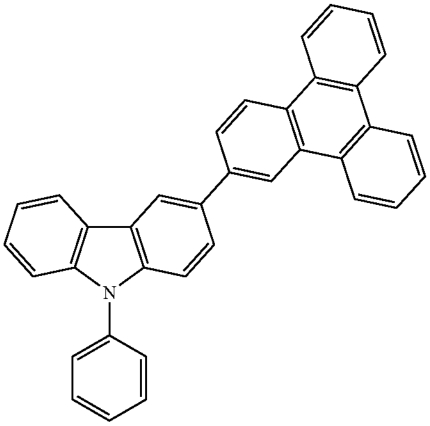
C-11
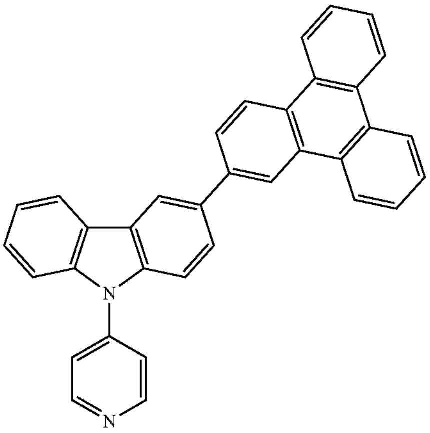
C-12
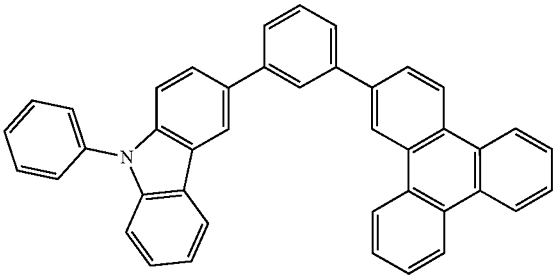
C-13
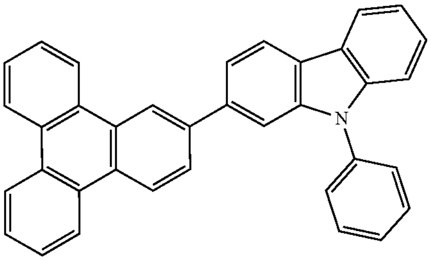
-continued
C-14
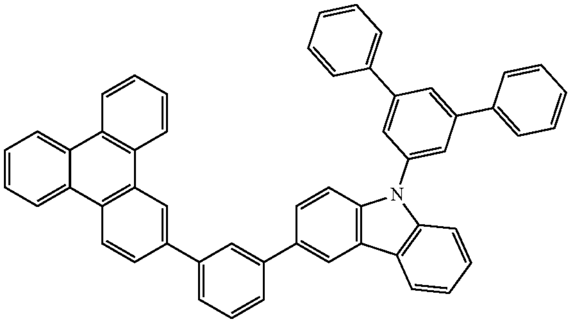
C-15
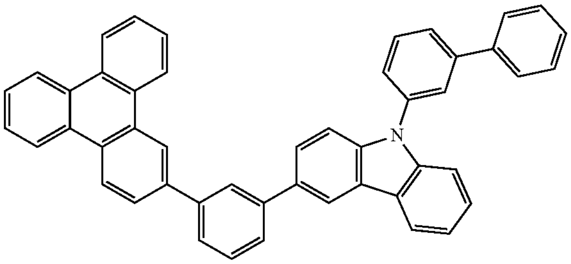
C-16
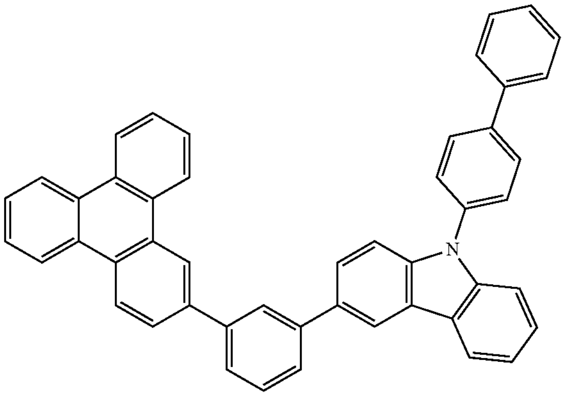
C-17
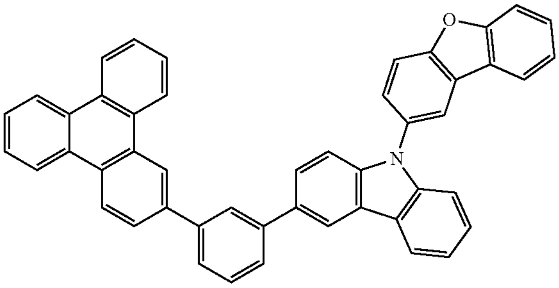

-continued
C-18
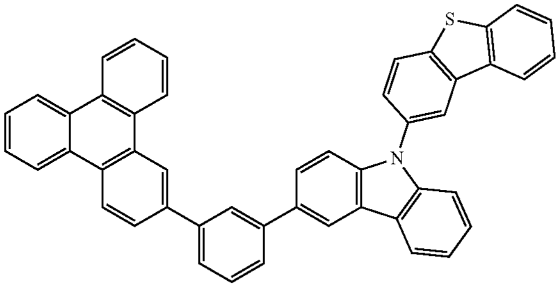
C-19
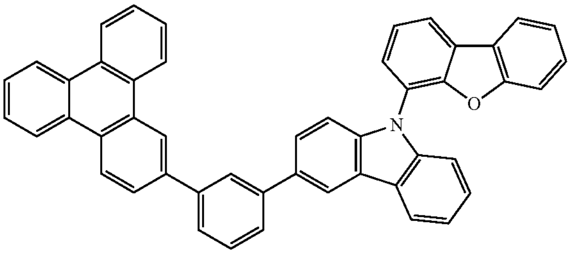
C-20
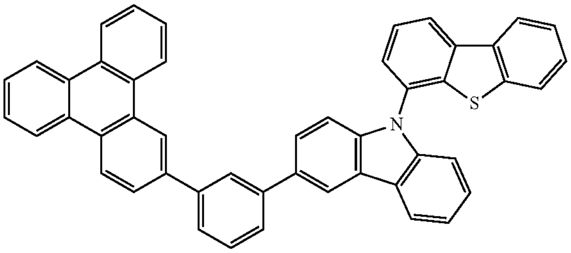
C-21
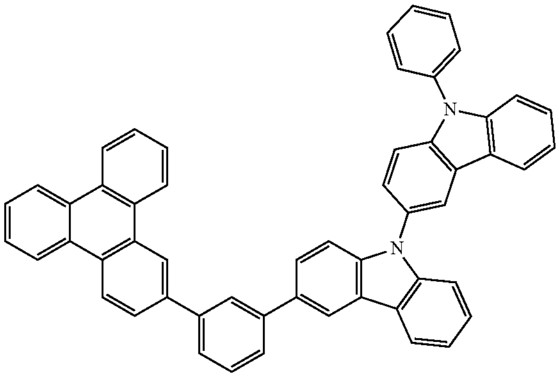
C-22
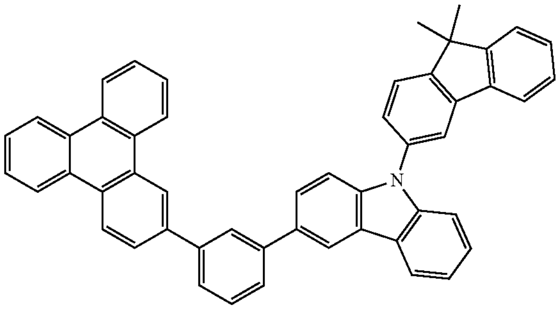
-continued
C-23
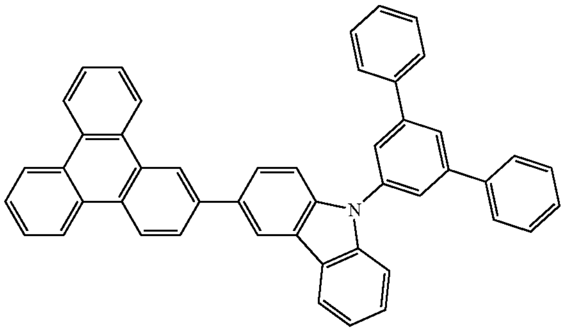
C-24
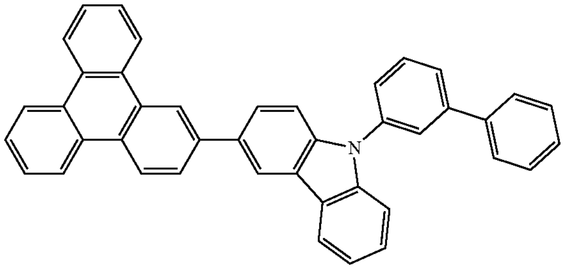
C-25
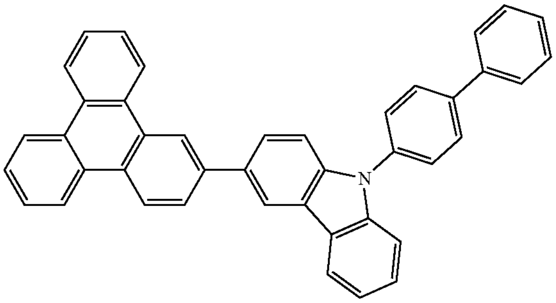
C-26
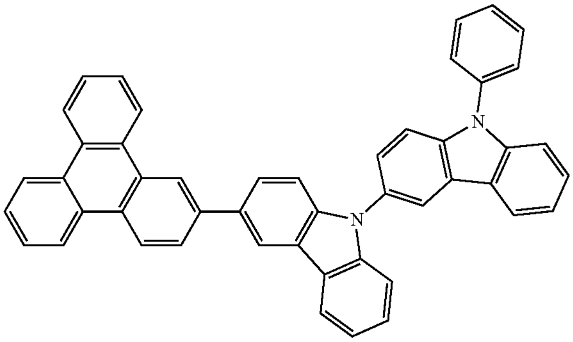
C-27
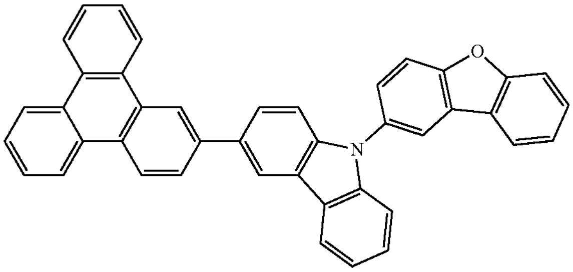

-continued
C-28
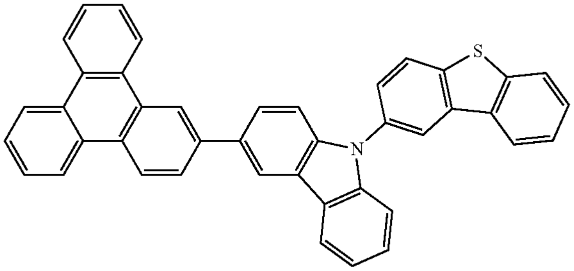
C-29
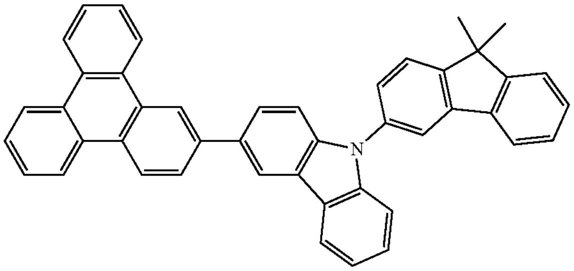
C-30
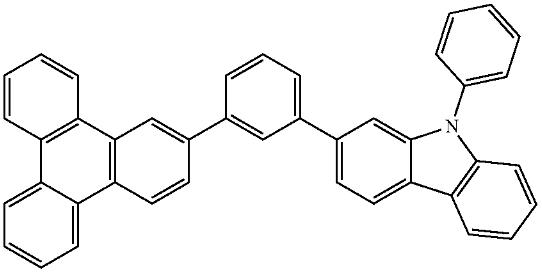
C-31
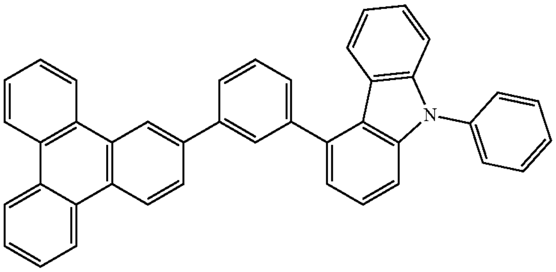
C-32
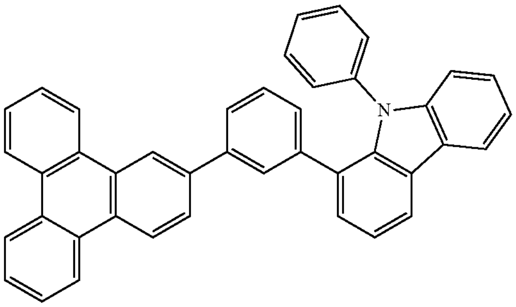
-continued
C-33
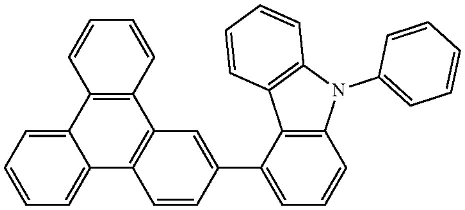
The compound represented by the above Chemical Formula 2-III may be, for example compounds selected from the following Group 7, but is not limited thereto.
[Group 7]
D-10
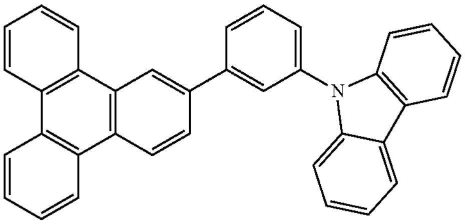
D-11
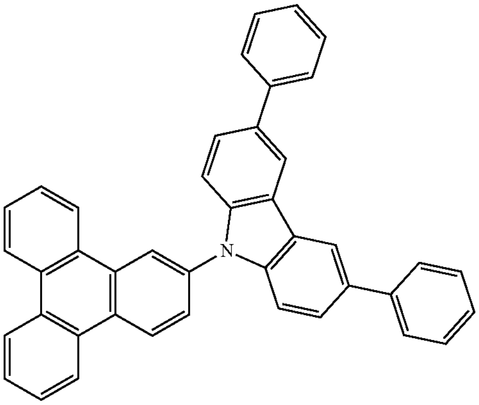
D-12
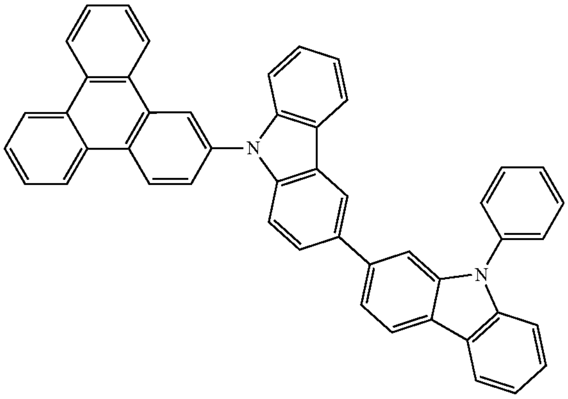

-continued
D-13
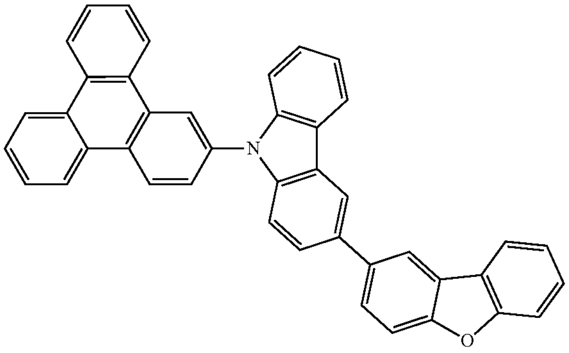
D-14
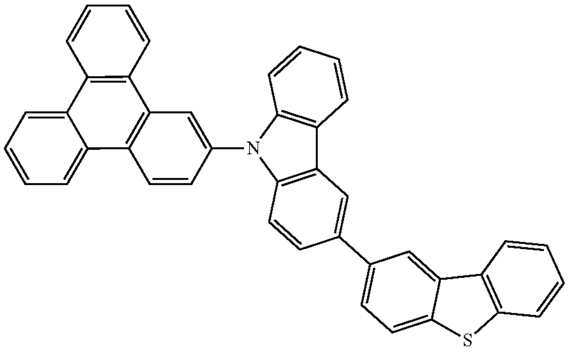
D-15
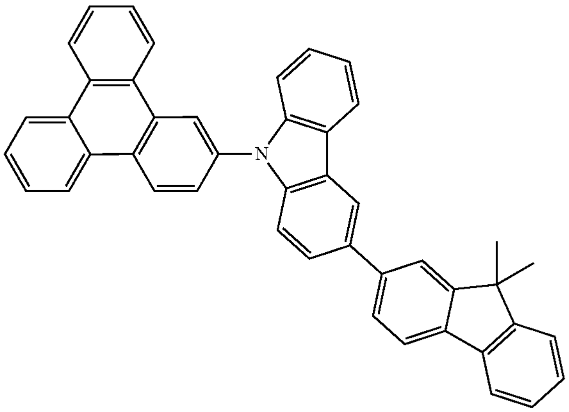
D-16
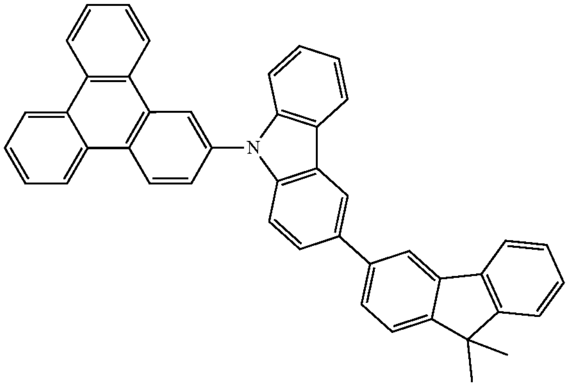
-continued
D-17
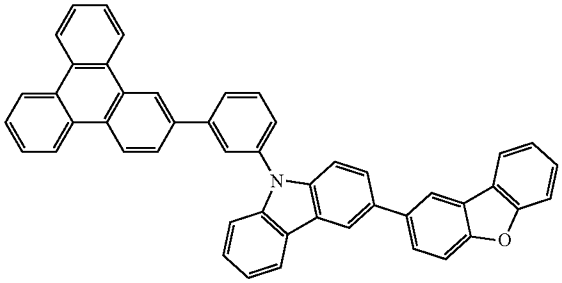
D-18
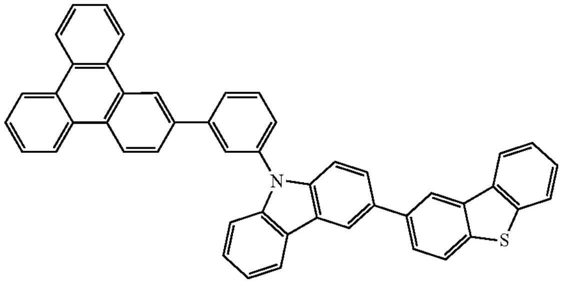
D-19
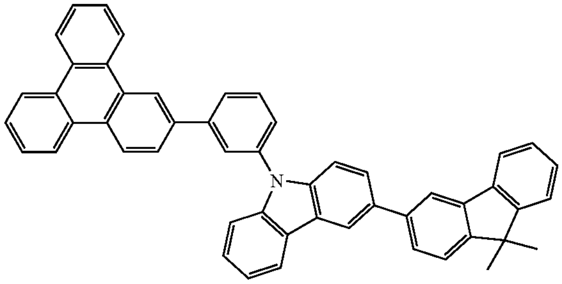
D-20
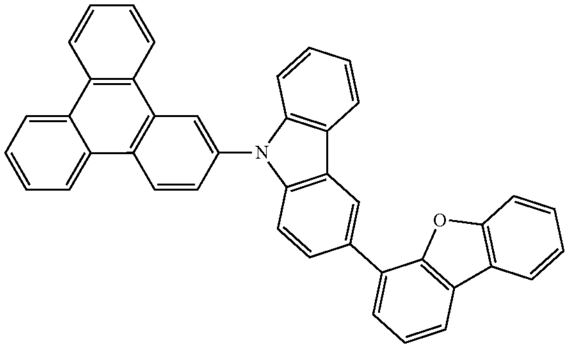

-continued
D-21
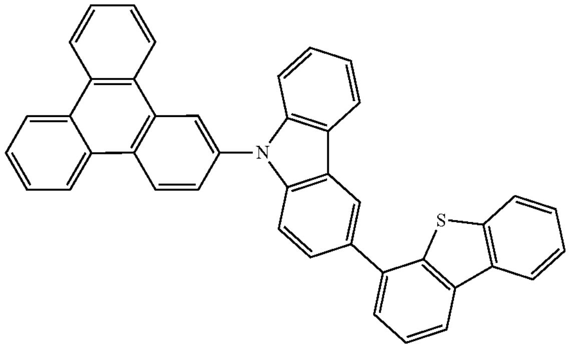
D-22
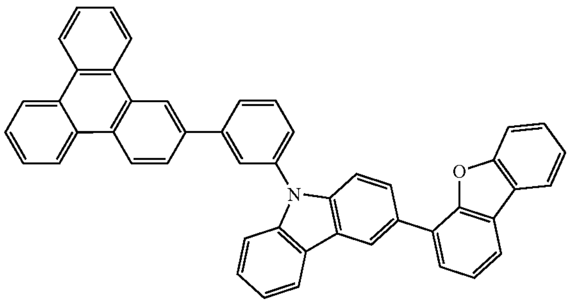
D-23
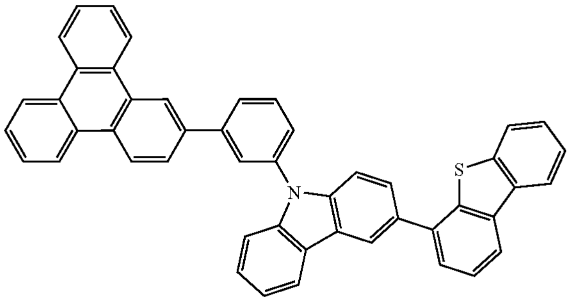
D-24
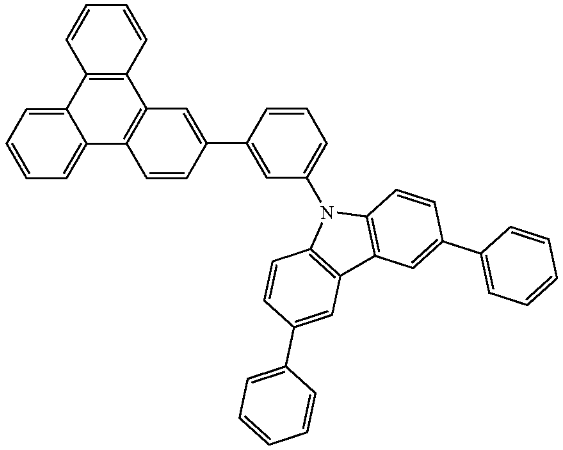
-continued
D-25
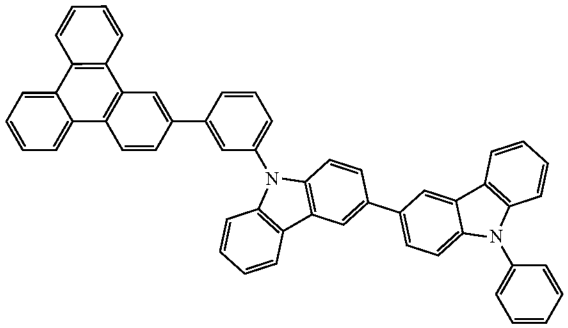
D-26
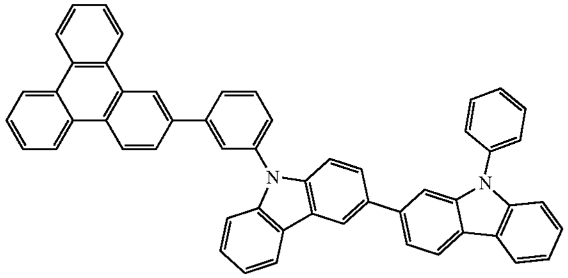
D-27
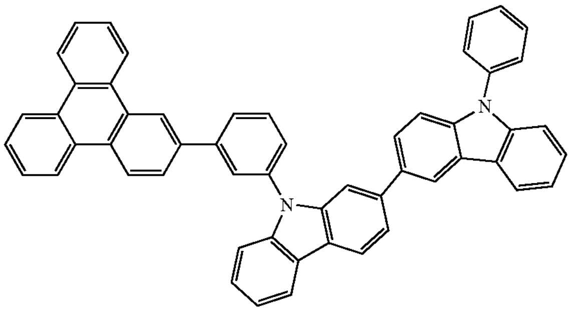
D-28
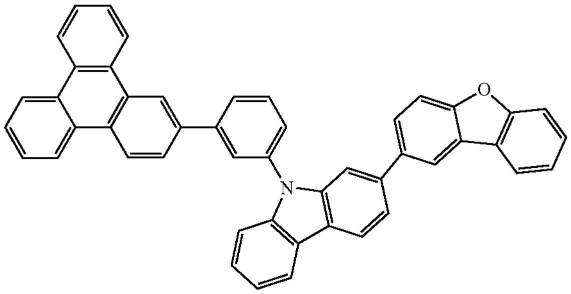
D-29
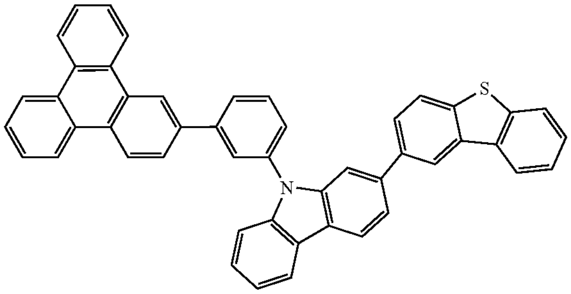

At least one or more kinds of the second host compound may be used.

The first and second host compounds may be variously combined and thus, provide various compositions.

As described above, since the first host compound has bipolar characteristics in which electron characteristics are relatively strong, while the second host compound has bipolar characteristics in which hole characteristic is relatively strong, the first and second host compounds may be used together to increase mobility of electrons and holes and thus, to remarkably improve luminous efficiency compared with when the first and second host compounds are used alone.

When the material having only electron or hole characteristics is used to form an emission layer, excitons are relatively more produced due to recombination of electrons and holes at the interface of the emission layer and the electron transport layer (ETL) or hole transport layer (HTL). As a result, the excitons in the emission layer may interact with the exitons produced at the interface of the emission layer and the electron transport layer (ETL) or hole transport layer (HTL) and thus, may cause a roll-off, which is that luminous efficiency is sharply deteriorated and thus, light emitting life-span characteristics is also sharply deteriorated. In order to solve this problem, the first and second host compounds are simultaneously introduced into the emission layer to balance carriers in the emission layer, so that a light emitting area may not be either the interface of the emission layer and the electron transport layer or hole transport layer (HTL) and thus, remarkably improving roll-off and simultaneously life-span characteristics.

The first host compound and the second host compound may be included in a weight ratio of, for example 1:10 to 10:1. Within the range, bipolar characteristics may be realized more efficiently and efficiency and life-span may be improved.

The composition may further include at least one host compound except the above first host compound and the second host compound.

The composition may further include a dopant. The dopant may be a red, green, or blue dopant, for example a phosphorescent dopant.

The dopant is mixed with the first host compound and the second host compound in a small amount to cause light emission, and may be generally a material such as a metal complex that emits light by multiple excitation into a triplet or more. The dopant may be, for example an inorganic, organic, or organic/inorganic compound, and one or more kinds thereof may be used.

Examples of the phosphorescent dopant may be an organic metal compound including Ir, Pt, Os, Ti, Zr, Hf, Eu, Tb, Tm, Fe, Co, Ni, Ru, Rh, Pd, or a combination thereof. The phosphorescent dopant may be, for example a compound represented by the following Chemical Formula Z, but is not limited thereto.

$L_2MX$ [Chemical Formula Z]

In the above Chemical Formula Z, M is a metal, and L and X are the same or different, and are a ligand to form a complex compound with M.

The M may be, for example Ir, Pt, Os, Ti, Zr, Hf, Eu, Tb, Tm, Fe, Co, Ni, Ru, Rh, Pd or a combination thereof, and the L and X may be, for example a bidentate ligand.

The composition may form a film using a dry film-forming method such as chemical vapor deposition or a solution method.

Hereinafter, an organic optoelectric device to which the composition is applied is described.

The organic optoelectric device may be any device to convert electrical energy into photoenergy and vice versa without particular limitation, and may be, for example an organic photoelectric device, an organic light emitting diode, an organic solar cell, and an organic photo-conductor drum.

The organic optoelectric device includes an anode and a cathode facing each other, and at least one organic layer interposed between the anode and the cathode, wherein the organic layer includes the above composition.

Herein, an organic light emitting diode as one example of an organic optoelectric device is described referring to drawings.

FIGS. 1 and 2 are cross-sectional views of each organic light emitting diode according to one embodiment.

Referring to FIG. 1, an organic light emitting diode 100 according to one embodiment includes an anode 120 and a cathode 110 facing each other and an organic layer 105 interposed between the anode 120 and cathode 110.

The anode 120 may be made of a conductor having a high work function to help hole injection, and may be for example metal, metal oxide and/or a conductive polymer. The anode 120 may be, for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or SnO2 and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a low work function to help electron injection, and may be for example metal, metal oxide and/or a conductive polymer. The cathode 110 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, LiO2/Al, LiF/Ca, LiF/Al and BaF2/Ca, but is not limited thereto.

The organic layer 105 may include an emission layer 130 including the above composition.

The emission layer 130 may include, for example the above composition.

Referring to FIG. 2, an organic light emitting diode 200 further includes a hole auxiliary layer 140 as well as an emission layer 230. The hole auxiliary layer 140 may further increase hole injection and/or hole mobility between the anode 120 and emission layer 230 and block electrons. The hole auxiliary layer 140 may be, for example a hole transport layer (HTL), a hole injection layer (HIL), and/or an electron blocking layer, and may include at least one layer.

In one embodiment, an organic light emitting diode may further include an electron transport layer (ETL), an electron injection layer (EIL), a hole injection layer (HIL), and the like, as an organic layer 105 in FIG. 1 or FIG. 2.

The organic light emitting diodes 100 and 200 may be manufactured by forming an anode or a cathode on a substrate, forming an organic layer in accordance with a dry coating method such as evaporation, sputtering, plasma plating, and ion plating; and forming a cathode or an anode thereon.

The organic light emitting diode may be applied to an organic light emitting diode (OLED) display.

MODE FOR INVENTION

Hereinafter, the embodiments are illustrated in more detail with reference to examples. These examples, however, are not in any sense to be interpreted as limiting the scope of the invention.

Synthesis of First Host Compound

Synthesis Example 1: Synthesis of Intermediate I-1

[Reaction Scheme 1]

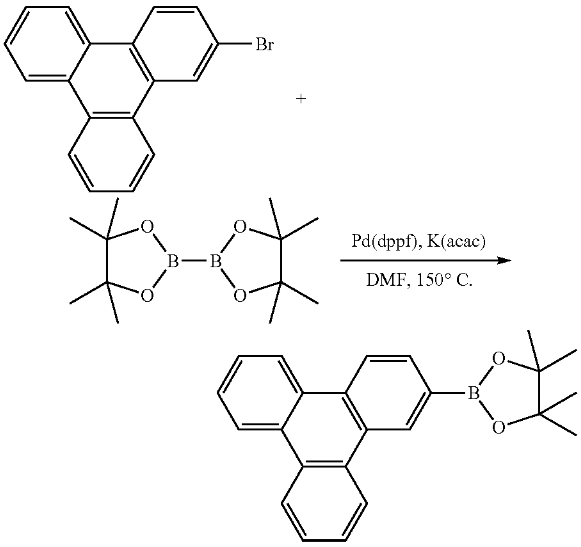

I-1

100 g (326 mmol) of 2-bromotriphenylene was dissolved in 1 L of dimethylformamide (DMF) under a nitrogen environment, 99.2 g (391 mmol) of bis(pinacolato)diboron, 2.66 g (3.26 mmol) of 1,1'-bis(diphenylphosphine)dichloropalladium (II), and 80 g (815 mmol) of potassium acetate were added thereto, and the mixture was heated and refluxed at 150 °C for 5 hours. When the reaction was complete, water was added to the reaction solution, and the mixture was filtered and then, dried in a vacuum oven. The obtained residue was separated and purified through flash column chromatography, obtain in 113 g (98%) of the compound I-1.

HRMS (70 eV, EI+): m/z calcd for C24H23BO2: 354.1791, found: 354.

Elemental Analysis: C, 81%; H, 7%

Synthesis Example 2: Synthesis of Intermediate I-2

[Reaction Scheme 2]

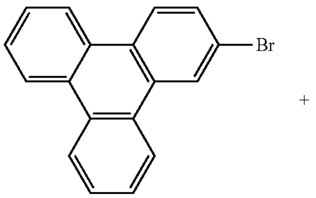

-continued

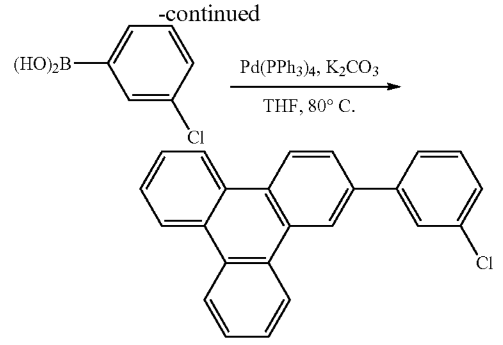

I-2

32.7 g (107 mmol) of 2-bromotriphenylene was dissolved in 0.3 L of tetrahydrofuran (THF) in a nitrogen environment, 20 g (128 mmol) of 3-chlorophenyl boronic acid and 1.23 g (1.07 mmol) of tetrakis(triphenylphosphine)palladium were added thereto, and the mixture was agitated. 36.8 g (267 mmol) of potassium carbonate saturated in water was added to the agitated resultant, and the resulting mixture was heated and refluxed at 80 °C for 24 hours. When the reaction was complete, water was added to the reaction solution, the mixture was extracted with dichloromethane (DCM), and the extract was treated with anhydrous $MgSO_4$ to remove moisture therefrom, filtered, and concentrated under a reduced pressure. The obtained residue was separated and purified through flash column chromatography, obtaining 22.6 g (63%) of the compound I-2.

HRMS (70 eV, EI+): m/z calcd for C24H15Cl: 338.0862, found: 338.

Elemental Analysis: C, 85%; H, 5%

Synthesis Example 3: Synthesis of Intermediate I-3

[Reaction Scheme 3]

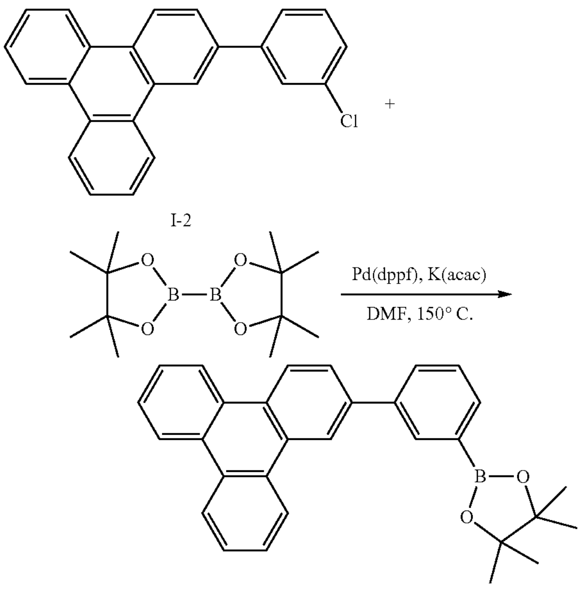

I-3

22.6 g (66.7 mmol) of the compound I-2 was dissolved in 0.3 L of dimethylformamide (DMF) under a nitrogen environment, 25.4 g (100 mmol) of bis(pinacolato)diboron, 0.54 g (0.67 mmol) of (1,1'-bis(diphenylphosphine)ferrocene) dichloropalladium (II), and 16.4 g (167 mmol) of potassium acetate were added thereto, and the mixture was heated and refluxed at 150 °C for 48 hours. When the reaction was complete, water was added to the reaction solution, and the mixture was filtered and dried in a vacuum oven. The obtained residue was separated and purified through flash column chromatography, obtaining 18.6 g (65%) of a compound I-3.

HRMS (70 eV, EI+): m/z calcd for C30H27BO2: 430.2104, found: 430.

Elemental Analysis: C, 84%; H, 6%

Synthesis Example 4: Synthesis of Intermediate I-4

[Reaction Scheme 4]

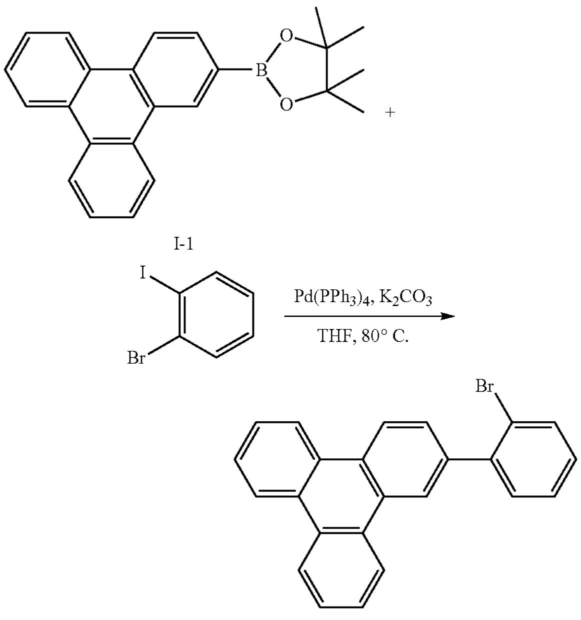

I-1

I-4

100 g (282 mmol) of the compound I-1 was dissolved in 1 L of tetrahydrofuran (THF) under a nitrogen environment, 95.9 g (339 mmol) of 1-bromo-2-iodobenzene and 3.26 g (2.82 mmol) of tetrakis(triphenylphosphine)palladium were added thereto, and the mixture was agitated. 97.4 g (705 mmol) of potassium carbonate saturated in water was added thereto, and the resulting mixture was heated and refluxed at 80 °C for 53 hours. When the reaction was complete, water was added to the reaction solution, the mixture was extracted with dichloromethane (DCM), and the extract was treated with anhydrous $MgSO_4$ to remove moisture therefrom, filtered, and concentrated under a reduced pressure. The obtained residue was separated and purified through flash column chromatography, obtaining 95.1 g (88%) of the compound I-4.

HRMS (70 eV, EI+): m/z calcd for C24H15Br: 382.0357, found: 382.

Elemental Analysis: C, 75%; H, 4%

Synthesis Example 5: Synthesis of Intermediate I-5

[Reaction Scheme 5]

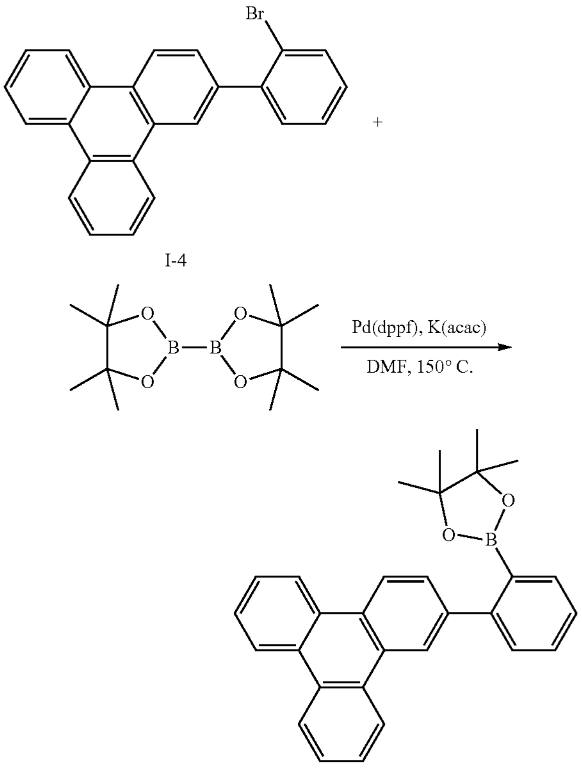

I-4

I-5

90 g (35 mmol) of the compound I-4 was dissolved in 0.8 L of dimethylformamide (DMF) under a nitrogen environment, 71.6 g (282 mmol) of bis(pinacolato)diboron, 1.92 g (2.35 mmol) of 1,1'-bis(diphenylphosphine)ferrocene)dichloropalladium (II), and 57.7 g (588 mmol) of potassium acetate were added thereto, and the mixture was heated and refluxed at 150 °C for 35 hours. When the reaction was complete, water was added to the reaction solution, and the mixture was filtered and dried in a vacuum oven. The obtained residue was separated and purified through flash column chromatography obtaining 74.8 g (74%) of the compound I-5.

HRMS (70 eV, EI+): m/z calcd for C30H27BO2: 430.2104, found: 430.

Elemental Analysis: C, 84%; H, 6%

Synthesis Example 6: Synthesis of Intermediate I-6

[Reaction Scheme 6]

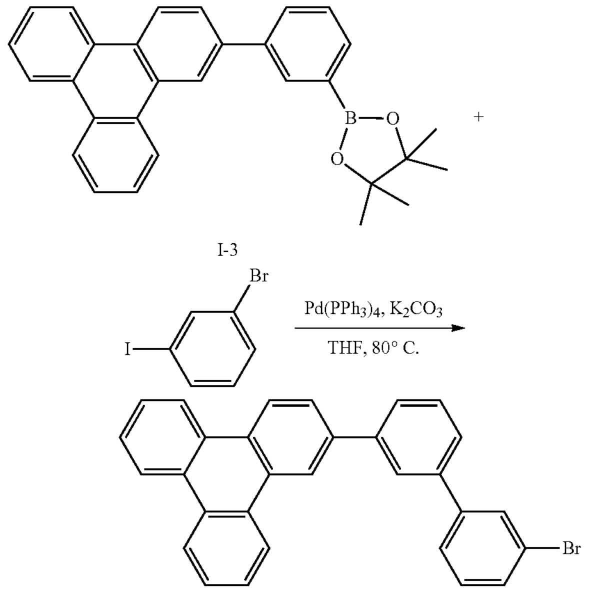

I-3

I-6

50 g (116 mmol) of the compound I-3 was dissolved in 0.5 L of tetrahydrofuran (THF) under a nitrogen environment, 39.4 g (139 mmol) of 1-bromo-3-iodobenzene and 1.34 g (1.16 mmol) of tetrakis(triphenylphosphine)palladium were added thereto, and the mixture was agitated. 40.1 g (290 mmol) of potassium carbonate saturated in water was added thereto, and the resulting mixture was heated and refluxed at 80 °C for 12 hours. When the reaction was complete, water was added to the reaction solution, and the mixture was extracted with dichloromethane (DCM), and the extract was treated with anhydrous $MgSO_4$ to remove moisture therefrom and then, filtered and concentrated under a reduced pressure. This obtained residue was separated and purified through flash column chromatography, obtaining 42.6 g (80%) of the compound I-6.

HRMS (70 eV, EI+): m/z calcd for C30H19Br: 458.0670, found: 458.

Elemental Analysis: C, 78%; H, 4%

Synthesis Example 7: Synthesis of Intermediate I-7

[Reaction Scheme 7]

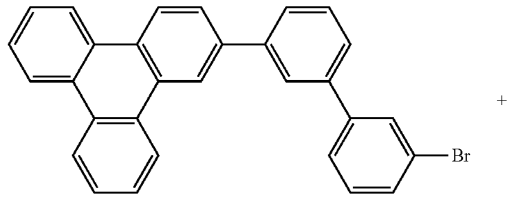

I-6

-continued

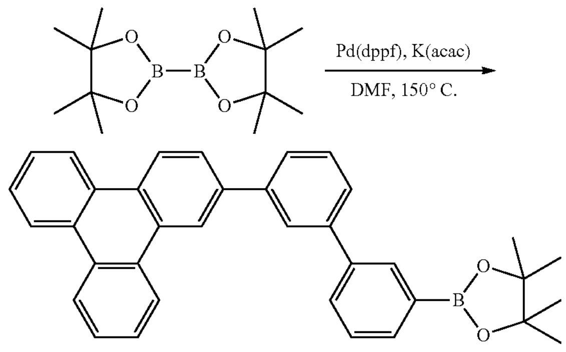

I-7

40 g (87.1 mmol) of the compound I-6 was dissolved in 0.3 L of dimethylformamide (DMF) under a nitrogen environment, 26.5 g (104 mmol) of bis(pinacolato)diboron, 0.71 g (0.87 mmol) of 1,1'-bis(diphenylphosphine)ferrocene)dichloropalladium (II), and 21.4 g (218 mmol) of potassium acetate were added thereto, and the mixture was heated and refluxed at 150 °C for 26 hours. When the reaction was complete, water was added to the reaction solution, and the mixture was filtered and dried in a vacuum oven. The obtained residue was separated and purified through flash column chromatography, obtaining 34 g (77%) of the compound I-7.

HRMS (70 eV, EI+): m/z calcd for C36H31BO2: 506.2417, found: 506.

Elemental Analysis: C, 85%; H, 6%

Synthesis Example 8: Synthesis of Intermediate I-8

[Reaction Scheme 8]

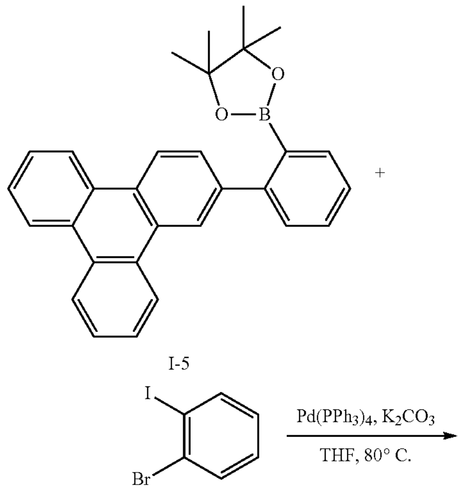

I-5

-continued

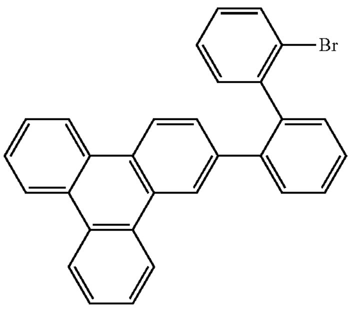

I-8

70 g (163 mmol) of the compound I-5 was dissolved in 0.6 L of tetrahydrofuran (THF) in a nitrogen environment, 55.2 g (195 mmol) of 1-bromo-2-iodobenzene and 1.88 g (1.63 mmol) of tetrakis(triphenylphosphine)palladium were added thereto, and the mixture was agitated. 56.3 g (408 mmol) of potassium carbonate saturated in water was added thereto, and the mixture was heated and refluxed at 80 °C for 12 hours. When the reaction was complete, water was added to the reaction solution, the mixture was extracted with dichloromethane (DCM), and the extract was treated with anhydrous $MgSO_4$ to remove moisture therefrom and then, filtered and concentrated under a reduced pressure. This obtained residue was separated and purified through flash column chromatography, obtaining 68.1 g (91%) of the compound I-8.

HRMS (70 eV, EI+): m/z calcd for C30H19Br: 458.0670, found: 458.

Elemental Analysis: C, 78%; H, 4%

Synthesis Example 9: Synthesis of Intermediate I-9

[Reaction Scheme 9]

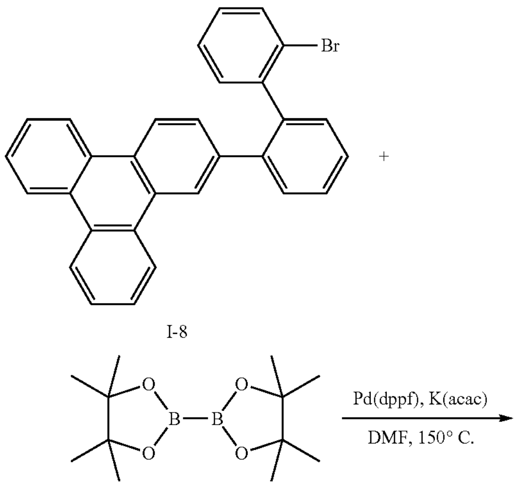

I-8

-continued

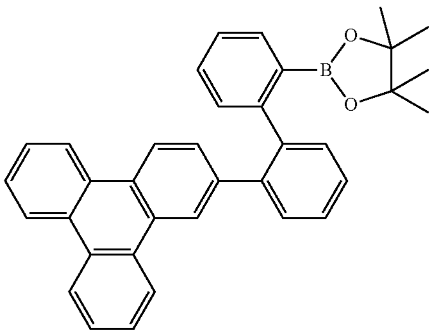

I-9

40 g (87.1 mmol) of the compound I-8 was dissolved in 0.3 L of dimethylformamide (DMF) under a nitrogen environment, 26.5 g (104 mmol) of bis(pinacolato)diboron, 0.71 g (0.87 mmol) of (1,1'-bis(diphenylphosphine)ferrocene) dichloropalladium (II), and 21.4 g (218 mmol) of potassium acetate were added thereto, and the mixture was heated and refluxed at 150 °C for 23 hours. When the reaction was complete, water was added to the reaction solution, and the mixture was filtered and dried in a vacuum oven. This obtained residue was separated and purified through flash column chromatography, obtaining 30.4 g (69%) of the compound I-9.

HRMS (70 eV, EI+): m/z calcd for C36H31BO2: 506.2417, found: 506.

Elemental Analysis: C, 85%; H, 6%

Synthesis Example 10: Synthesis of Intermediate I-10

[Reaction Scheme 10]

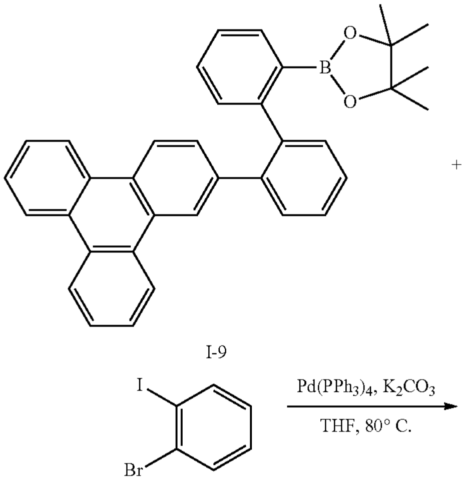

I-9

-continued

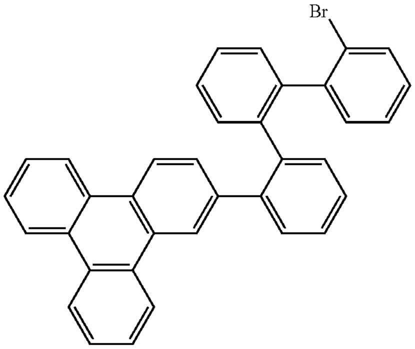

I-10

30 g (59.2 mmol) of the compound I-9 was dissolved in 0.3 L of tetrahydrofuran (THF) under a nitrogen environment, 20.1 g (71.1 mmol) of 1-bromo-2-iodobenzene and 0.68 g (0.59 mmol) of tetrakis(triphenylphosphine)palladium were added thereto, and the mixture was agitated. 20.5 g (148 mmol) of potassium carbonate saturated in water was added thereto, and the mixture was heated and refluxed at 80 °C for 16 hours. When the reaction was complete, water was added to the reaction solution, the mixture was extracted with dichloromethane (DCM), and the extract was treated with anhydrous $MgSO_4$ to remove moisture therefrom and then, filtered and concentrated under a reduced pressure. The obtained residue was separated and purified through flash column chromatography, obtaining 32.4 g (85%) of the compound I-10.

HRMS (70 eV, EI+): m/z calcd for C36H23Br: 534.0983, found: 534.

Elemental Analysis: C, 81%; H, 4%

Synthesis Example 11: Synthesis of Intermediate I-11

[Reaction Scheme 11]

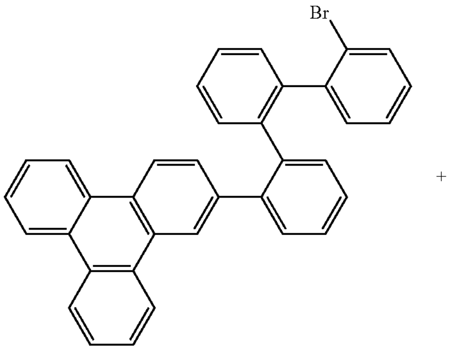

I-10

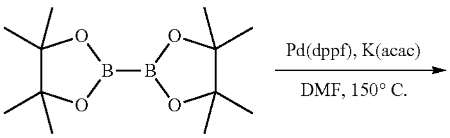

-continued

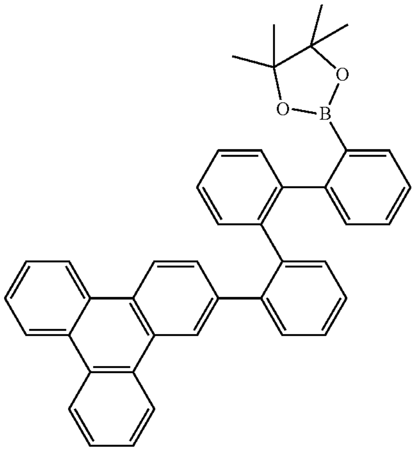

I-11

30 g (56 mmol) of the compound I-10 was dissolved in 0.3 L of dimethylformamide (DMF) under a nitrogen environment, 17.1 g (67.2 mmol) of bis(pinacolato)diboron, 0.46 g (0.56 mmol) of (1,1'-bis(diphenylphosphine)ferrocene)dichloropalladium (II), and 13.7 g (140 mmol) of potassium acetate were added thereto, and the mixture was heated and refluxed at 150 °C for 25 hours. When the reaction was complete, water was added to the reaction solution, and the mixture was filtered and dried in a vacuum oven. The obtained residue was separated and purified through flash column chromatography, obtaining 22.8 g (70%) of the compound I-11.

HRMS (70 eV, EI+): m/z calcd for C42H35BO2: 582.2730, found: 582.

Elemental Analysis: C, 87%; H, 6%

Synthesis Example 12: Synthesis of Compound A-1

[Reaction Scheme 12]

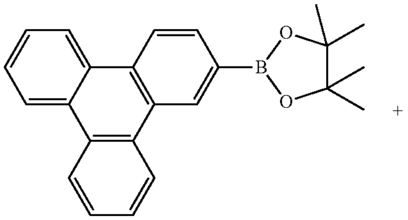

I-1

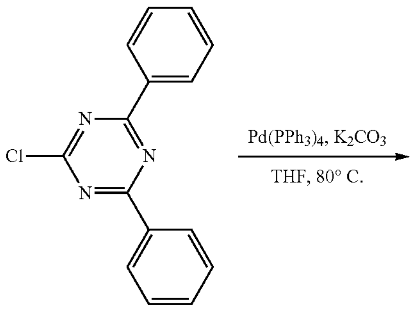

-continued

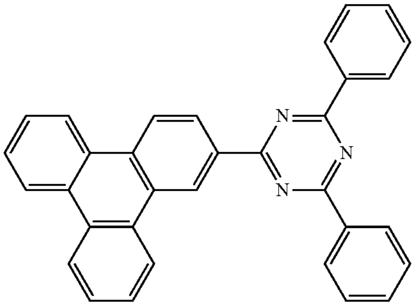

A-1

20 g (56.5 mmol) of the compound I-1 was dissolved in 0.2 L of tetrahydrofuran (THF) in a nitrogen environment, 15.1 g (56.5 mmol) of 2-chloro-4,6-diphenyl-1,3,5-triazine and 0.65 g (0.57 mmol) of tetrakis(triphenylphosphine) palladium were added thereto, and the mixture was agitated. 19.5 g (141 mmol) of potassium carbonate saturated in water was added thereto, and the mixture was heated and refluxed at 80 °C for 20 hours. When the reaction was complete, water was added to the reaction solution, the mixture was extracted with dichloromethane (DCM), and the extract was treated with anhydrous $MgSO_4$ to remove moisture therefrom and then, filtered and concentrated under a reduced pressure. The obtained residue was separated and purified through flash column chromatography, obtaining 22.1 g (85%) of the compound A-1.

HRMS (70 eV, EI+): m/z calcd for C33H21N3: 459.1735, found: 459.

Elemental Analysis: C, 86%; H, 5%

Synthesis Example 13: Synthesis of Compound A-13

[Reaction Scheme 13]

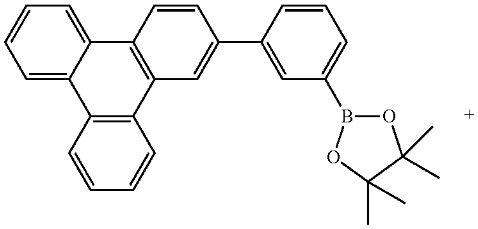

I-3

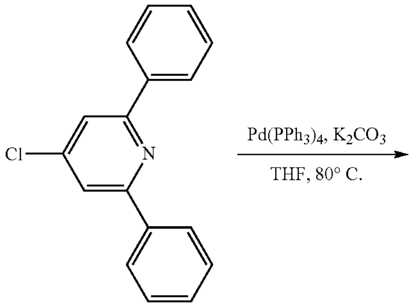

-continued

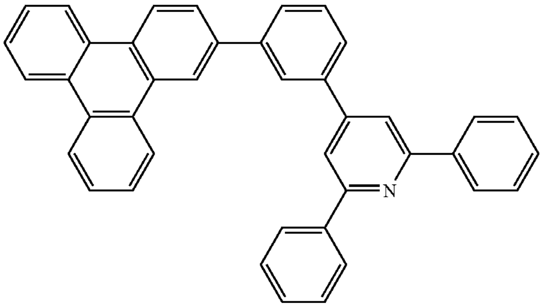

A-13

20 g (46.5 mmol) of the compound I-3 was dissolved in 0.2 L of tetrahydrofuran (THF) under a nitrogen environment, 12.4 g (46.5 mmol) of 4-chloro-2,6-diphenylpyridine and 0.54 g (0.47 mmol) of tetrakis(triphenylphosphine) palladium were added thereto, and the mixture was agitated. 16.1 g (116 mmol) of potassium carbonate saturated in water was added thereto, and the mixture was heated and refluxed at 80 °C for 17 hours. When the reaction was complete, water was added to the reaction solution, the mixture was extracted with dichloromethane (DCM), and the extract was treated with anhydrous $MgSO_4$ to remove moisture therefrom and then, filtered and concentrated under a reduced pressure. This obtained residue was separated and purified through flash column chromatography, obtaining 18.9 g (76%) of the compound A-13.

HRMS (70 eV, EI+): m/z calcd for C41H27N: 533.2143, found: 533.

Elemental Analysis: C, 92%; H, 5%

Synthesis Example 14: Synthesis of Compound A-14

[Reaction Scheme 14]

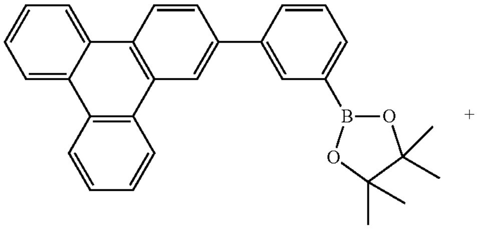

I-3

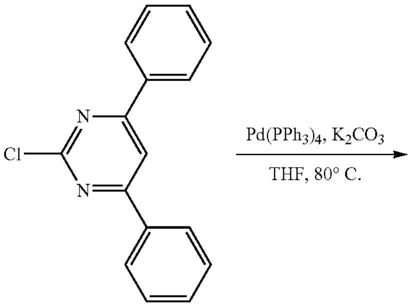

-continued

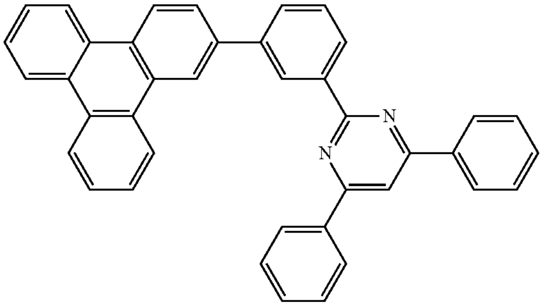

A-14

20 g (46.5 mmol) of the compound I-3 was dissolved in 0.2 L of tetrahydrofuran (THF) under a nitrogen environment, 12.4 g (46.5 mmol) of 2-chloro-4,6-diphenylpyrimidine and 0.54 g (0.47 mmol) of tetrakis(triphenylphosphine) palladium were added thereto, and the mixture was agitated. 16.1 g (116 mmol) of potassium carbonate saturated in water was added thereto, and the mixture was heated and refluxed at 80 °C for 15 hours. When the reaction was complete, water was added to the reaction solution, the mixture was extracted with dichloromethane (DCM), and the extract was treated with anhydrous $MgSO_4$ to remove moisture therefrom and then, filtered and concentrated under a reduced pressure. The obtained residue was separated and purified through flash column chromatography, obtaining 20.4 g (82%) of the compound A-14.

HRMS (70 eV, EI+): m/z calcd for C40H26N2: 534.2096, found: 534.

Elemental Analysis: C, 90%; H, 5%

Synthesis Example 15: Synthesis of Compound A-15

[Reaction Scheme 15]

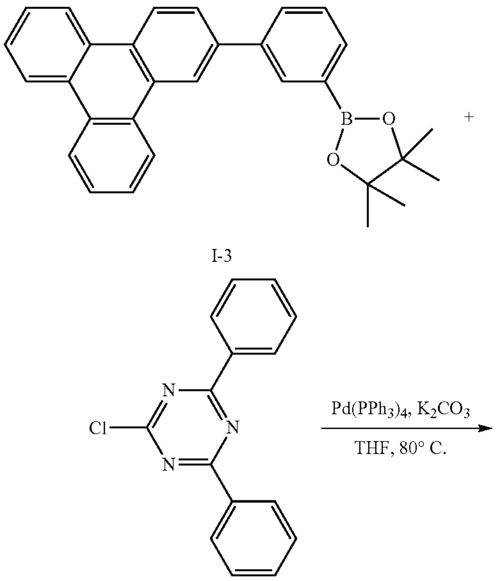

I-3

-continued

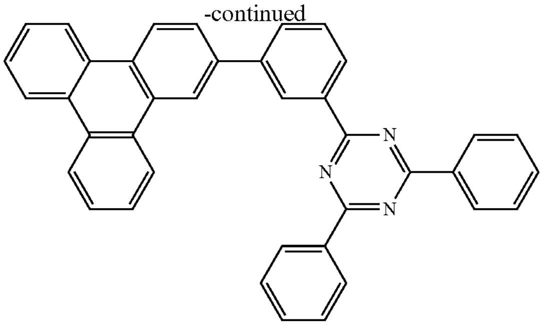

A-15

20 g (46.5 mmol) of the compound I-3 was dissolved in 0.2 L of tetrahydrofuran (THF) under a nitrogen environment, 12.4 g (46.5 mmol) of 2-chloro-4,6-diphenyl-1,3,5-triazine and 0.54 g (0.47 mmol) of tetrakis(triphenylphosphine)palladium were added thereto, and the mixture was agitated. 16.1 g (116 mmol) of potassium carbonate saturated in water was added thereto, and the mixture was heated and refluxed at 80 °C for 20 hours. When the reaction was complete, water was added to the reaction solution, the mixture was extracted with dichloromethane (DCM), and the extract was treated with anhydrous $MgSO_4$ to remove moisture therefrom and filtered and then, concentrated under a reduced pressure. The obtained residue was separated and purified through flash column chromatography, obtaining 21.2 g (85%) of the compound A-15.

HRMS (70 eV, EI+): m/z calcd for C39H25N3: 535.2048, found: 535.

Elemental Analysis: C, 87%; H, 5%

Synthesis Example 16: Synthesis of Compound A-24

[Reaction Scheme 16]

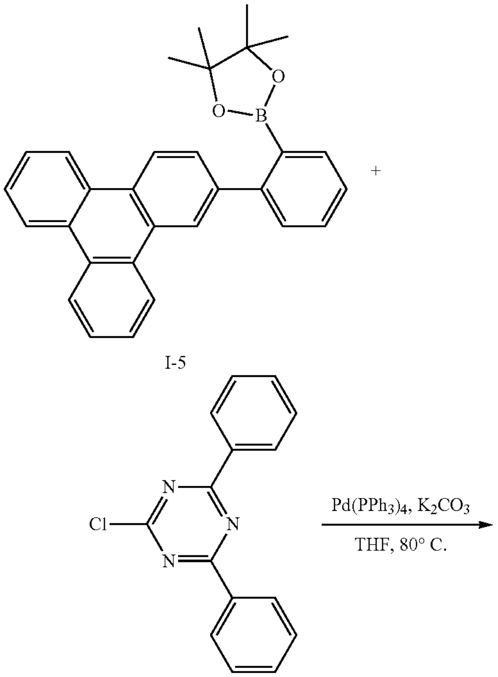

I-5

-continued

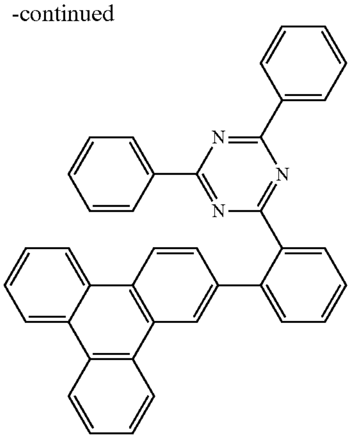

A-24

20 g (46.5 mmol) of the compound I-5 was dissolved in 0.2 L of tetrahydrofuran (THF) under a nitrogen environment, 12.4 g (46.5 mmol) of 2-chloro-4,6-diphenyl-1,3,5-triazine and 0.54 g (0.47 mmol) of tetrakis(triphenylphosphine)palladium were added thereto, and the mixture was agitated. 16.1 g (116 mmol) of potassium carbonate saturated in water was added thereto, and the mixture was heated and refluxed at 80 °C for 27 hours. When the reaction was complete, water was added to the reaction solution, the mixture was extracted with dichloromethane (DCM), and the extract was treated with anhydrous $MgSO_4$ to remove moisture therefrom and then, filtered and concentrated under a reduced pressure. This obtained residue was separated and purified through flash column chromatography, obtaining 19.7 g (79%) of the compound A-24.

HRMS (70 eV, EI+): m/z calcd for C39H25N3: 535.2048, found: 535.

Elemental Analysis: C, 87%; H, 5%

Synthesis Example 17: Synthesis of Compound A-33

[Reaction Scheme 17]

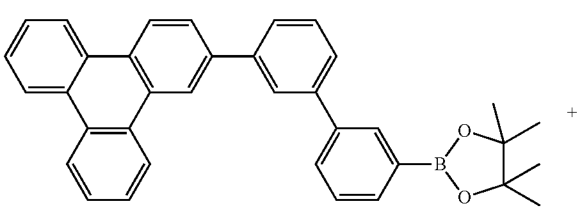

I-7

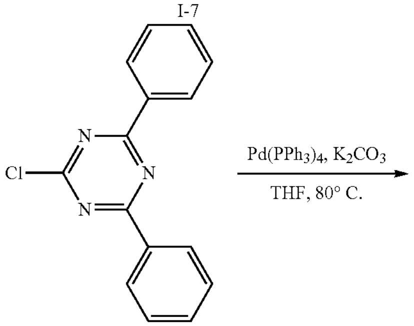

-continued

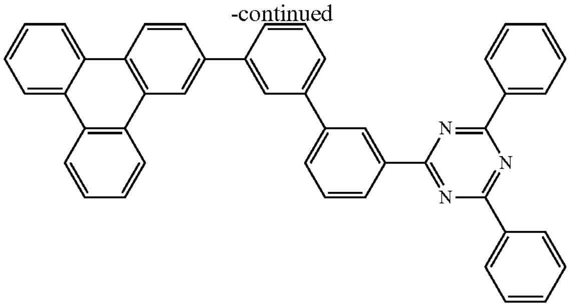

A-33

20 g (39.5 mmol) of the compound I-7 was dissolved in 0.2 L of tetrahydrofuran (THF) under a nitrogen environment, 10.6 g (39.5 mmol) of 2-chloro-4,6-diphenyl-1,3,5-triazine and 0.46 g (0.4 mmol) of tetrakis(triphenylphosphine)palladium were added thereto, and the mixture was agitated. 13.6 g (98.8 mmol) of potassium carbonate saturated in water was added thereto, and the mixture was heated and refluxed at 80 °C for 23 hours. When the reaction was complete, water was added to the reaction solution, the mixture was extracted with dichloromethane (DCM), and the extract was treated with anhydrous $MgSO_4$ to remove moisture therefrom and then, filtered and concentrated under a reduced pressure. The obtained residue was separated and purified through flash column chromatography, obtaining 17.9 g (74%) of the compound A-33.

HRMS (70 eV, EI+): m/z calcd for C45H29N3: 611.2361, found: 611.

Elemental Analysis: C, 88%; H, 5%

Synthesis Example 18: Synthesis of Compound A-69

[Reaction Scheme 18]

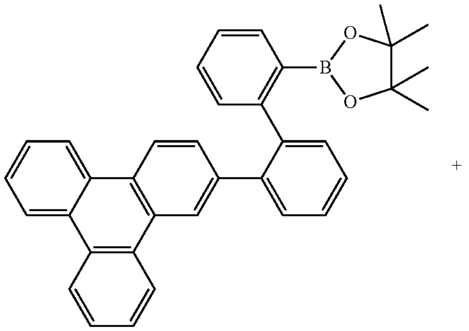

I-9

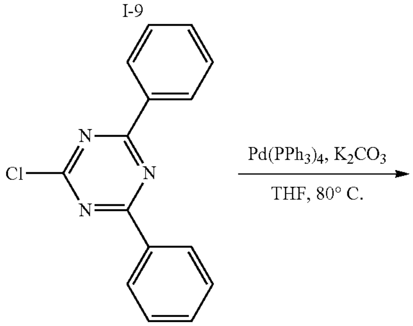

-continued

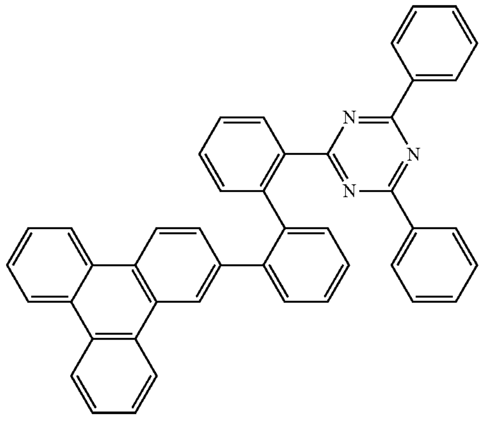

A-69

20 g (39.5 mmol) of the compound I-9 was dissolved in 0.2 L of tetrahydrofuran (THF) under a nitrogen environment, 10.6 g (39.5 mmol) of 2-chloro-4,6-diphenyl-1,3,5-triazine and 0.46 g (0.4 mmol) of tetrakis(triphenylphosphine)palladium were added thereto, and the mixture was agitated. 13.6 g (98.8 mmol) of potassium carbonate saturated in water was added thereto, and the resulting mixture was heated and refluxed at 80 °C for 32 hours. When the reaction was complete, water was added to the reaction solution, the mixture was extracted with dichloromethane (DCM), and the extract was treated with anhydrous $MgSO_4$ to remove moisture therefrom and then, filtered and concentrated under a reduced pressure. This obtained residue was separated and purified through flash column chromatography, obtaining 15.2 g (63%) the compound A-69.

HRMS (70 eV, EI+): m/z calcd for C45H29N3: 611.2361, found: 611.

Elemental Analysis: C, 88%; H, 5%

Synthesis Example 19: Synthesis of Compound A-87

[Reaction Scheme 19]

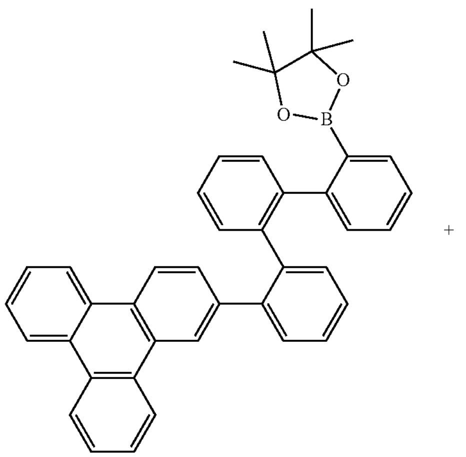

I-11

-continued

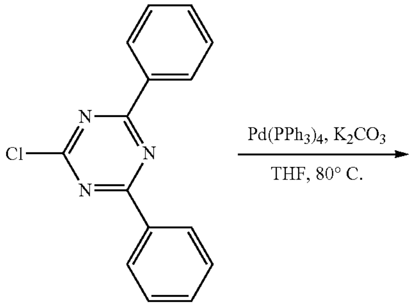

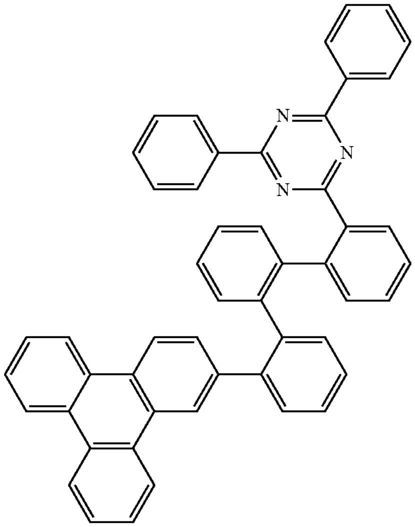

A-87

20 g (34.3 mmol) of the compound I-11 was dissolved in 0.15 L of tetrahydrofuran (THF) under a nitrogen environment, 9.19 g (34.3 mmol) of 2-chloro-4,6-diphenyl-1,3,5-triazine and 0.4 g (0.34 mmol) of tetrakis(triphenylphosphine)palladium were added thereto, and the mixture was agitated. 11.9 g (85.8 mmol) of potassium carbonate saturated in water was added thereto, and the resulting mixture was heated and refluxed at 80 °C for 29 hours. When the reaction was complete, water was added to the reaction solution, the mixture was extracted with dichloromethane (DCM), and the extract was treated with anhydrous $MgSO_4$ to remove moisture therefrom and then, filtered and concentrated under a reduced pressure. The obtained residue was separated and purified through flash column chromatography, obtaining 16.3 g (69%) of the compound A-87.

HRMS (70 eV, EI+): m/z calcd for C51H33N3: 687.2674, found: 687.

Elemental Analysis: C, 89%; H, 5%

Synthesis 1 of Second Host Compound: Synthesis of Compound C-10

[Reaction Scheme 20]

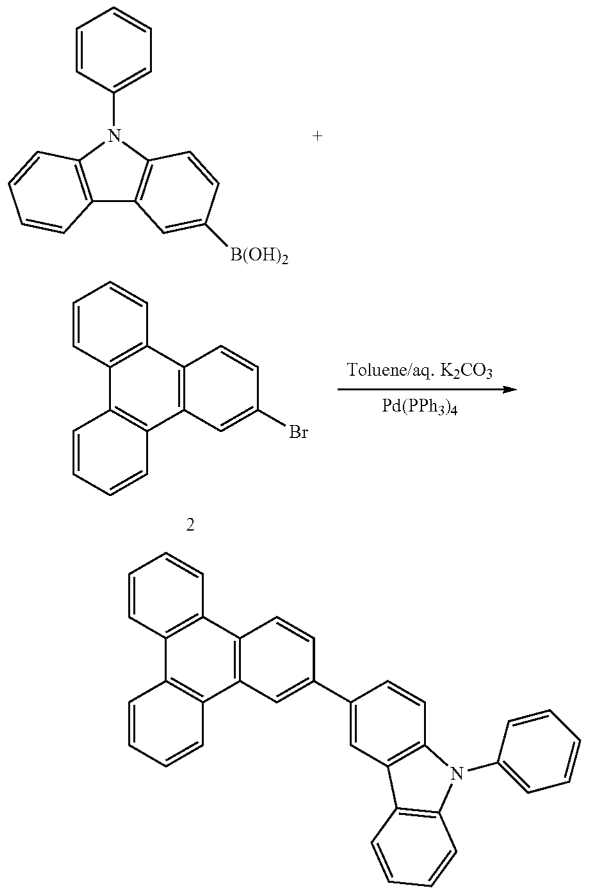

2

C-10

10 g (34.83 mmol) of phenylcarbazolyl boronic acid, 11.77 g (38.31 mmol) of the compound 2, and 14.44 g (104.49 mmol) of potassium carbonate, and 0.80 g (0.7 mmol) of tetrakis-(triphenylphosphine)palladium (0) were suspended in 140 ml of toluene and 50 ml of distilled water, and the suspended solution was refluxed and agitated for 12 hours. Subsequently, the resultant was extracted with dichloromethane and distilled water, and the obtained organic layer was silica gel-filtered. Subsequently, after removing an organic solution therefrom, a solid product was obtained through a silica gel column with hexane:dichloromethane=7:3(v/v) and then, recrystallized with dichloromethane and n-hexane, obtaining 14.4 g (a yield: 88%) of a compound C-10.

HRMS (70 eV, EI+): m/z calcd for C36H23N: 469.18, found: 469.

Elemental Analysis: C, 92%; H, 5%

Synthesis 2 of Second Host Compound: Synthesis of Compound B-10

[Reaction Scheme 21]

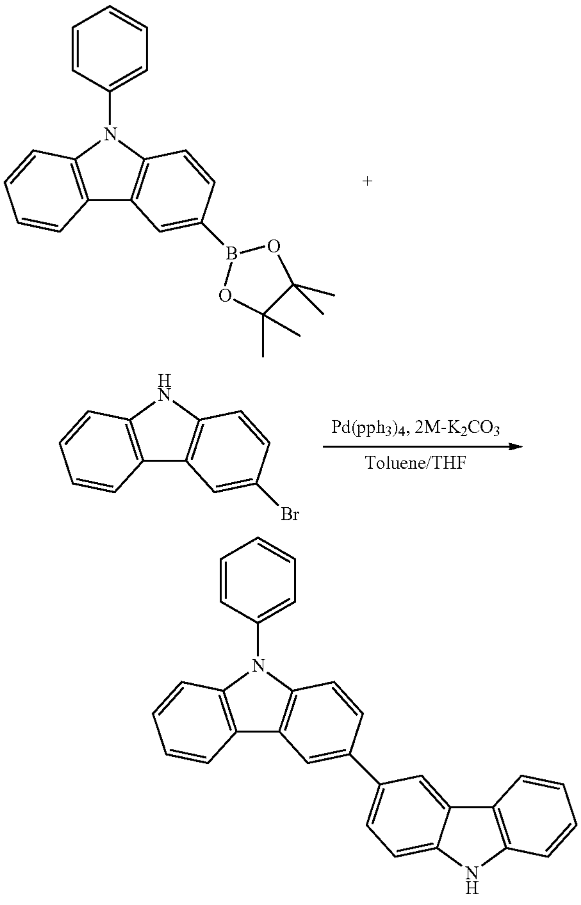

(J)

(J) +

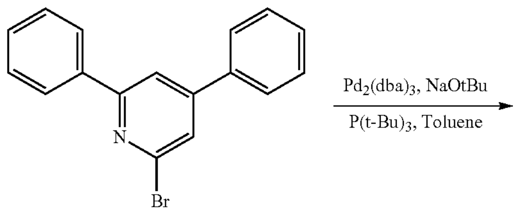

-continued

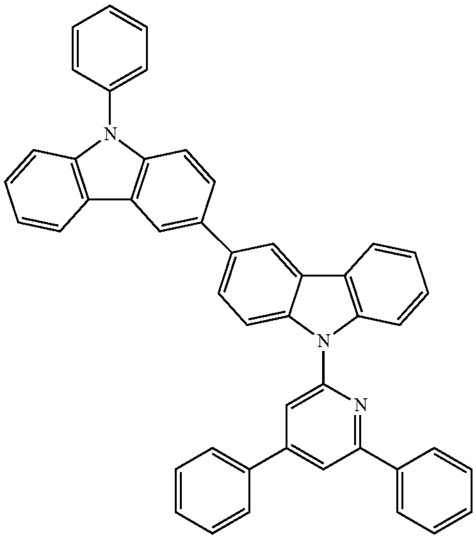

B-10

First Step: Synthesis of Compound J 26.96 g (81.4 mmol) of N-phenyl carbazole-3-boronic acid pinacolate and 23.96 g (97.36 mmol) of 3-bromo carbazole were mixed with 230 mL of tetrahydrofuran and 100 ml of a 2 M-potassium carbonate aqueous solution, and the mixture was heated and refluxed under a nitrogen stream for 12 hours. When the reaction was complete, a solid produced by pouring the reactant into methanol was filtered and then, dissolved in chlorobenzene, activated carbon and anhydrous magnesium sulfate were added thereto, and the mixture was agitated. The solution was filtered and recrystallized by using chlorobenzene and methanol, obtaining 22.6 g of a compound J (a yield: 68%).

HRMS (70 eV, EI+): m/z calcd for C30H20N2: 408.16, found: 408.

Elemental Analysis: C, 88%; H, 5%

Second Step: Synthesis of Compound B-10

22.42 g (54.88 mmol) of the compound J, 20.43 g (65.85 mmol) of 2-bromo-4,6-diphenylpyridine, and 7.92 g (82.32 mmol) of tertiarybutoxy sodium were dissolved in 400 ml of toluene, and 1.65 g (1.65 mmol) of palladium dibenzylideneamine and 1.78 g (4.39 mmol) of tertiarybutyl phosphorus were added in a dropwise fashion. The reaction solution was heated and refluxed at 110 °C under a nitrogen stream for 12 hours. When the reaction was complete, a solid produced by pouring methanol to the reactant was filtered and then, dissolved in chlorobenzene, activated carbon and anhydrous magnesium sulfate were added thereto, and the mixture was agitated. The solution was filtered and recrystallized with chlorobenzene and methanol, obtaining 28.10 g of a compound B-10 (a yield: 80%).

HRMS (70 eV, EI+): m/z calcd for C47H31N3: 637.25, found: 637.

Elemental Analysis: C, 89%; H, 5%

Synthesis 3 of Second Host Compound: Synthesis of Compound B-31

[Reaction Scheme 22]

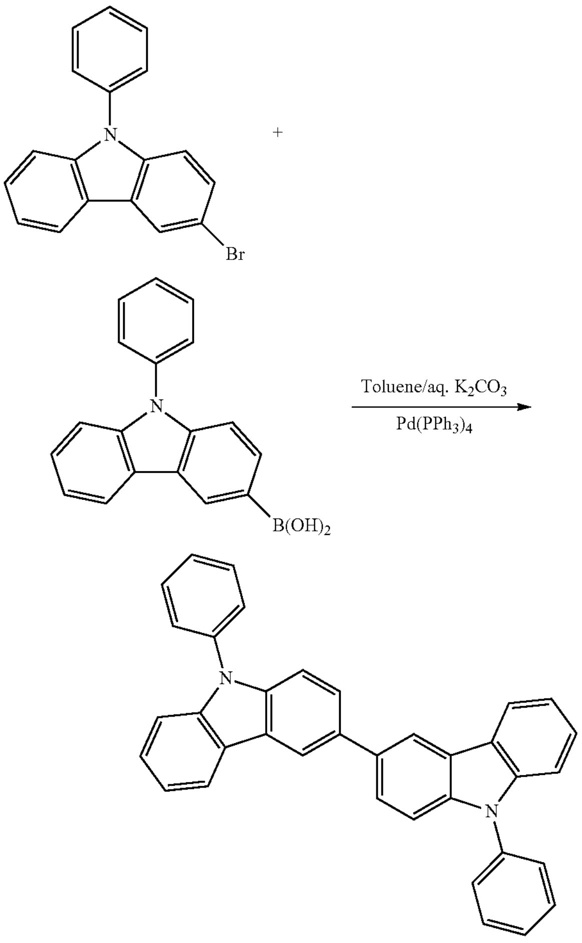

B-31

9.97 g (30.95 mmol) of phenylcarbazolyl bromide, 9.78 g (34.05 mmol) of phenylcarbazolyl boronic acid, 12.83 g (92.86 mmol) of potassium carbonate, and 1.07 g (0.93 mmol) of tetrakis-(triphenylphosphine)palladium (0) were suspended in 120 ml of toluene and 50 ml of distilled water, and the suspended solution was refluxed and agitated for 12 hours. Subsequently, the resultant was extracted with dichloromethane and distilled water, and an organic layer was silica gel-filtered therefrom. Subsequently, after removing an organic solution therefrom, a solid product obtained therefrom was recrystallized with dichloromethane and n-hexane, obtaining 13.8 g of a compound B-31 (a yield: 92%).

HRMS (70 eV, EI+): m/z calcd for C36H24N2: 484.19, found: 484.

Elemental Analysis: C, 89%; H, 5%

Synthesis 4 of Second Host Compound: Synthesis of Compound B-34

[Reaction Scheme 23]

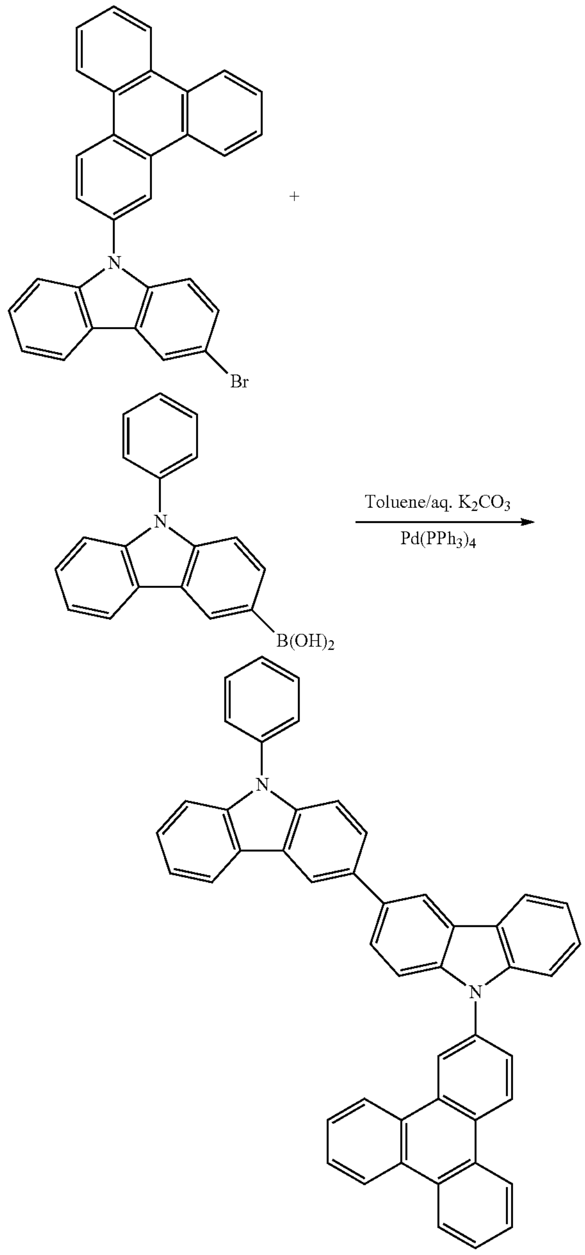

B-34

14.62 g (30.95 mmol) of triphenyl carbazolyl bromide, 9.78 g (34.05 mmol) of phenylcarbazolyl boronic acid, 12.83 g (92.86 mmol) of potassium carbonate, and 1.07 g (0.93 mmol) of tetrakis-(triphenylphosphine)palladium (0) were suspended in 120 ml of toluene and 50 ml of distilled water, and the suspended solution was refluxed and agitated for 12 hours. Subsequently, the resultant was extracted with dichloromethane and distilled water, and an organic layer produced therein was silica gel-filtered. Subsequently, a solid product obtained after removing an organic solution therefrom was recrystallized with dichloromethane and n-hexane, obtaining 16.7 g of a compound B-34 (a yield: 85%).

HRMS (70 eV, EI+): m/z calcd for C47H29N2: 621.23, found: 621.

Elemental Analysis: C, 91%; H, 5%

Synthesis 5 of Second Host Compound: Synthesis of Compound B-43

[Reaction Scheme 24]

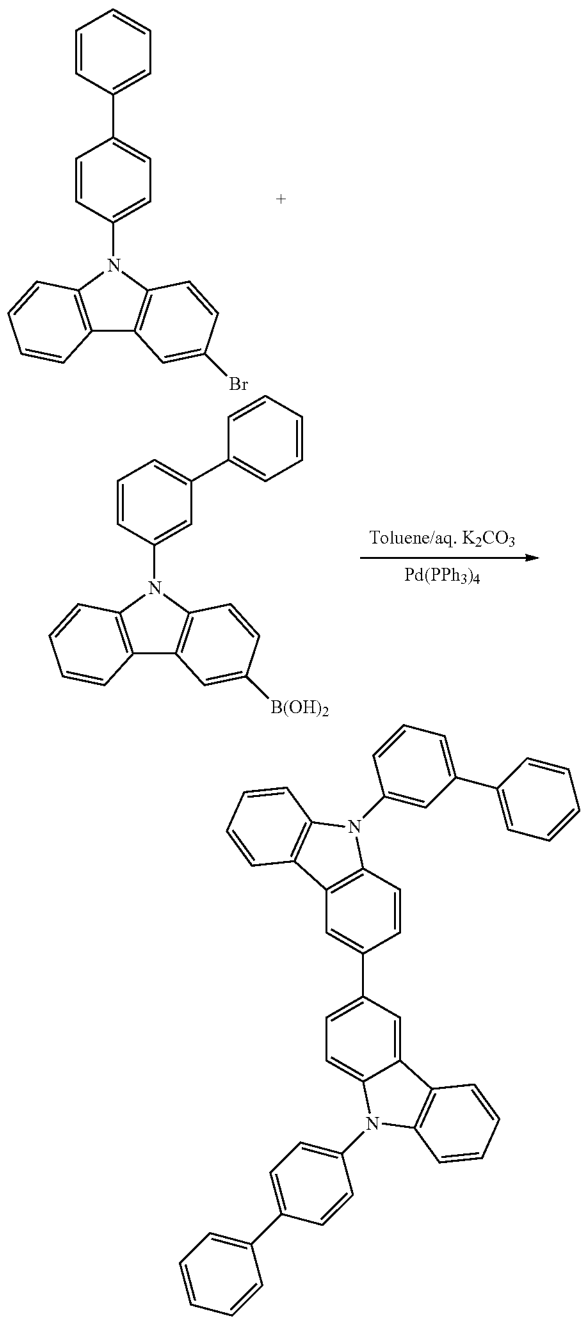

B-43

12.33 g (30.95 mmol) of biphenylcarbazolyl bromide, 12.37 g (34.05 mmol) of biphenylcarbazolyl boronic acid, 12.83 g (92.86 mmol) of potassium carbonate, and 1.07 g (0.93 mmol) of tetrakis-(triphenylphosphine)palladium (0) were suspended in 120 ml of toluene and 50 ml of distilled water, and the suspended solution was refluxed and agitated for 12 hours. Subsequently, the resultant was extracted with dichloromethane and distilled water, and an organic layer produced therein was silica gel-filtered. Subsequently, a solid product obtained after removing an organic solution therefrom was recrystallized with dichloromethane and n-hexane, obtaining 18.7 g of a compound B-43 (a yield: 92%).

HRMS (70 eV, EI+): m/z calcd for $C_{48}H_{32}N_2$: 636.26, found: 636.

Elemental Analysis: C, 91%; H, 5%

Manufacture of Organic Light Emitting Diode

Example 1

A glass substrate coated with ITO (Indium tin oxide) to be 1500 Å thick was ultrasonic wave-washed with a distilled water. Subsequently, the glass substrate was ultrasonic wave-washed with a solvent such as isopropyl alcohol, acetone, methanol, and the like, moved to a plasma cleaner, cleaned by using oxygen plasma for 10 minutes, and then, moved to a vacuum depositor. This obtained ITO transparent electrode was used as a anode, N4,N4'-diphenyl-N4,N4'-bis (9-phenyl-9H-carbazol-3-yl)biphenyl-4,4'-diamine) (a compound A) was vacuum-deposited on the ITO substrate upper to form a 700 Å-thick hole injection layer (HIL), 1,4,5,8,9,11-hexaazatriphenylene-hexacarbonitrile (HAT-CN) (a compound B) was deposited to be 50 Å-thick on the injection layer, and N-(biphenyl-4-yl)-9,9-dimethyl-N-(4-(9-phenyl-9H-carbazol-3-yl)phenyl)-9H-fluoren-2-amine (a compound C) was deposited to be 1020 Å-thick to form a hole transport layer (HTL). On the hole transport layer (HTL), a 400 Å-thick emission layer was formed by simultaneously using the synthesized compound A-33 and the compound B-10 as a host, which was doped with 10 wt % of tris(4-methyl-2,5-diphenylpyridine)iridium (III) (a compound D) as a dopant. Herein, the compound A-33 and the compound B-10 were used in a weight ratio of 4:1.

Subsequently, 8-(4-(4-(naphthalen-2-yl)-6-(naphthalen-3-yl)-1,3,5-triazin-2-yl)phenyl)quinoline) (a compound E) and Liq were simultaneously vacuum-deposited in a ratio of 1:1 on the emission layer upper to form a 300 Å-thick electron transport layer (ETL), and 15 Å-thick Liq and 1200 Å-thick Al were sequentially vacuum-deposited to form a cathode on the electron transport layer (ETL), manufacturing an organic light emitting diode.

The organic light emitting diode had a five-layered organic thin film structure and specifically, a structure of ITO/A 700 Å/B 50 Å/C 1020 Å/EML[A-33:B-10:D=X:X:10%]400 Å/E:Liq 300 Å/Liq 15 Å/Al 1200 Å.

(X=a weight ratio)

Example 2

An organic light emitting diode was manufactured according to the same method as Example 1 except for using the compound A-33 and the compound B-10 in a weight ratio of 1:1.

Example 3

An organic light emitting diode was manufactured according to the same method as Example 1 except for using the compound A-33 and the compound B-10 in a weight ratio of 1:4.

Example 4

An organic light emitting diode was manufactured according to the same method as Example 1 except for using the compound B-31 instead of the compound B-10.

Example 5

An organic light emitting diode was manufactured according to the same method as Example 4 except for using the compound A-33 and the compound B-31 in a ratio of 1:1.

Example 6

An organic light emitting diode was manufactured according to the same method as Example 1 except for using the compound C-10 instead of the compound B-10.

Example 7

An organic light emitting diode was manufactured according to the same method as Example 6 except for using the compound A-33 and the compound C-10 in a weight ratio of 1:1.

Example 8

An organic light emitting diode was manufactured according to the same method as Example 6 except for using the compound A-33 and the compound C-10 in a weight ratio of 1:4.

Example 9

An organic light emitting diode was manufactured according to the same method as Example 1 except for using the compound B-34 instead of the compound B-10.

Example 10

An organic light emitting diode was manufactured according to the same method as Example 9 except for using the compound A-33 and the compound B-34 in a weight ratio of 1:1.

Example 11

An organic light emitting diode was manufactured according to the same method as Example 1 except for using the compound A-33 and the compound B-43 in a weight ratio of 1:1.

Comparative Example 1

An organic light emitting diode was manufactured according to the same method as Example 1 except for using 4,4'-di(9H-carbazol-9-yl)biphenyl (CBP) as a single host instead of the two kinds of the compound A-33 and the compound B-10.

Comparative Example 2

An organic light emitting diode was manufactured according to the same method as Example 1 except for using the compound A-33 as a single host instead of the two kinds of the compound A-33 and the compound B-10.

Comparative Example 3

An organic light emitting diode was manufactured according to the same method as Example 1 except for using the compound B-10 as a single host instead of the two kinds of the compound A-33 and the compound B-10.

Comparative Example 4

An organic light emitting diode was manufactured according to the same method as Example 1 except for using the compound B-31 as a single host instead of the two kinds of the compound A-33 and the compound B-10.

Comparative Example 5

An organic light emitting diode was manufactured according to the same method as Example 1 except for using the compound C-10 as a single host instead of the two kinds of the compound A-33 and the compound B-10.

Comparative Example 6

An organic light emitting diode was manufactured according to the same method as Example 1 except for using the compound B-34 as a single host instead of the two kinds of the compound A-33 and the compound B-10.

Comparative Example 7

An organic light emitting diode was manufactured according to the same method as Example 1 except for using the compound B-43 as a single host instead of the two kinds of the compound A-33 and the compound B-10.

Evaluation Luminous efficiency and life-span of each organic light emitting diode according to Examples 1 to 11 and Comparative Examples 1 to 7 were measured.

The measurements were specifically performed in the following method, and the results were provided in the following Table 1.

(1) Measurement of Current Density Change Depending on Voltage Change

Current values flowing in the unit device of the manufactured organic light emitting diodes were measured for, while increasing the voltage from 0V to 10V using a current-voltage meter (Keithley 2400), and the measured current values were divided by an area to provide the results.

(2) Measurement of Luminance Change Depending on Voltage Change

Luminance of the manufactured organic light emitting diodes was measured for luminance, while increasing the voltage from 0V to 10V using a luminance meter (Minolta Cs-1000A).

(3) Measurement of Luminous Efficiency

Current efficiency (cd/A) at the same current density (10 mA/cm2) were calculated by using the luminance, current density, and voltages obtained from items (1) and (2).

(4) Measurement of Roll-Off

An efficiency roll-off was calculated as a percentage by using (Max value−value at 6000 cd/$m^2$/Max value) in the (3).

(5) Measurement of Life-Span

Luminance (cd/$m^2$) was maintained at 6000 cd/$m^2$ and a time at current efficiency (cd/A) decreases to 97% was measured.

TABLE 1

| | First host | Second host | First host:Second host (wt/wt) | Luminous efficiency (cd/A) | Roll-off (%) | Life-span T97 (h) |
|---|---|---|---|---|---|---|
| Example1 | A-33 | B-10 | 4:1 | 39.8 | 25.5 | 300 |
| Example2 | A-33 | B-10 | 1:1 | 45.1 | 17.3 | 350 |
| Example3 | A-33 | B-10 | 1:4 | 43.3 | 8.7 | 200 |
| Example4 | A-33 | B-31 | 4:1 | 45.6 | 19.2 | 350 |
| Example5 | A-33 | B-31 | 1:1 | 52.9 | 10.4 | 150 |
| Example6 | A-33 | C-10 | 4:1 | 38.6 | 27.5 | 350 |
| Example7 | A-33 | C-10 | 1:1 | 42.3 | 24.8 | 350 |
| Example8 | A-33 | C-10 | 1:4 | 46 | 17.5 | 220 |
| Example9 | A-33 | B-34 | 4:1 | 40.7 | 23.2 | 540 |
| Example10 | A-33 | B-34 | 1:1 | 47 | 14.4 | 630 |
| Example11 | A-33 | B-43 | 1:1 | 44 | 20.7 | 720 |
| Comparative Example1 | | CBP | — | 19.3 | 0.9 | 0.5 |
| Comparative Example2 | | A-33 | — | 31.1 | 30.3 | 150 |
| Comparative Example3 | | B-10 | — | 34.8 | 6.2 | 10 |
| Comparative Example4 | | B-31 | — | 2.3 | 2.5 | — |
| Comparative Example5 | | C-10 | — | 15.3 | 4.1 | 10 |
| Comparative Example6 | | B-34 | — | 17 | 3.8 | 10 |
| Comparative Example7 | | B-43 | — | 2.6 | 1.4 | 10 |

* Impossible to measure life-span of a device having luminance of less than or equal to 6000 cd/$m^2$ Referring to Table 1, the organic light emitting diodes according to Examples 1 to 11 showed remarkably improved luminous efficiency, roll-off, and life-span characteristics compared with the organic light emitting diodes according to Comparative Examples 1 to 7.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the above embodiments should be understood to be exemplary but not limiting the present invention in any way.

The invention claimed is:

1. A composition, comprising:

a first compound selected from the compounds listed in the following Group 1; and a second compound represented by the following Chemical Formula 2-I:

[Group 1]

-continued
[A-1]
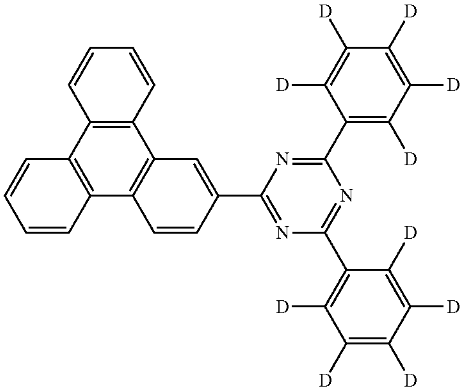
[A-2]
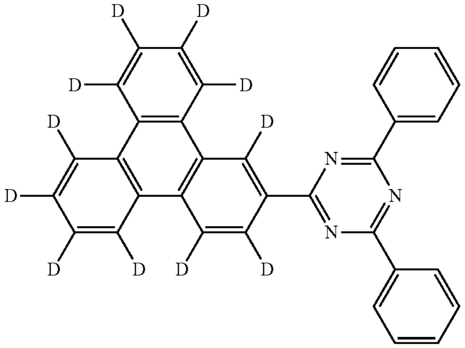
[A-3]
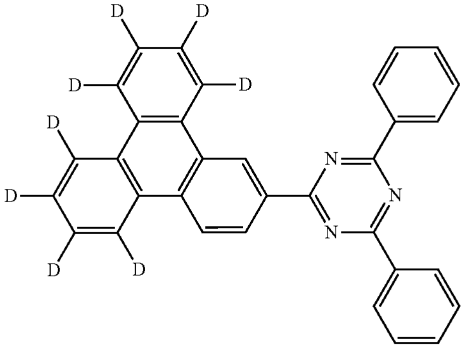
[A-4]
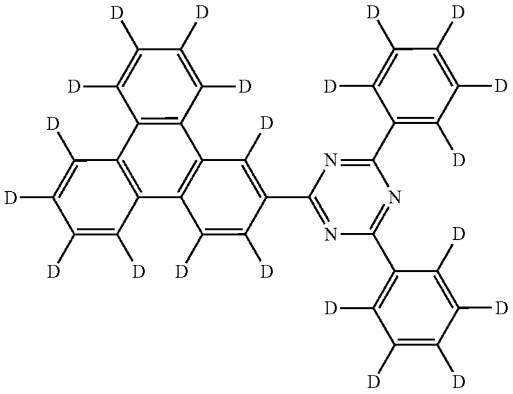
-continued
[A-5]
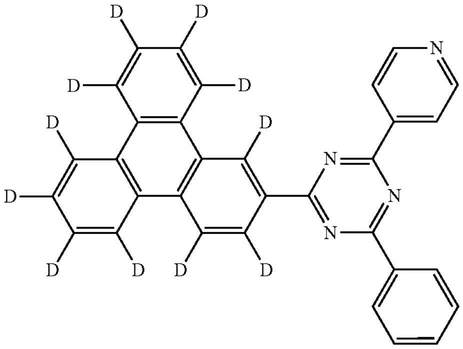
[A-6]
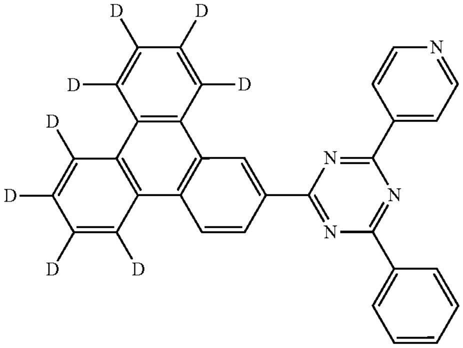
[A-7]
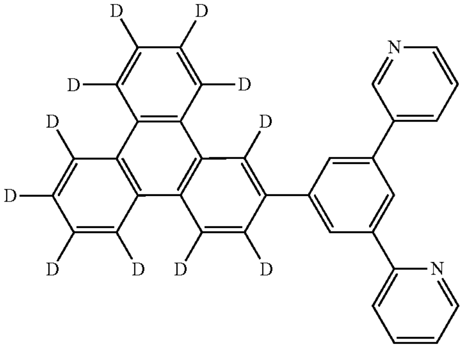
[A-8]
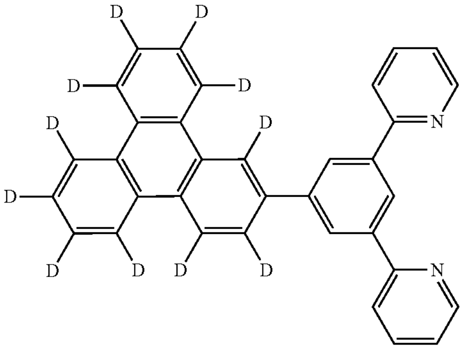

-continued
[A-9]
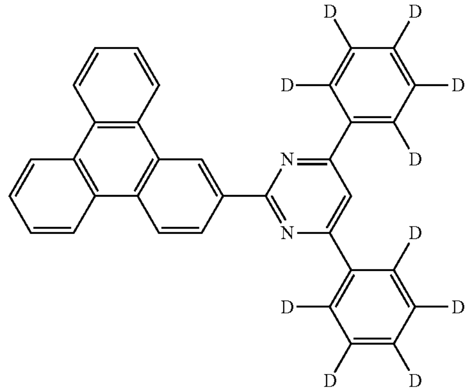
[A-10]
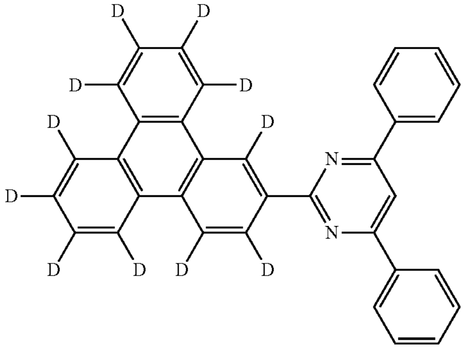
[A-11]
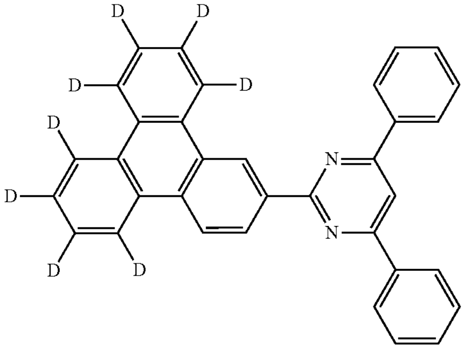
[A-12]
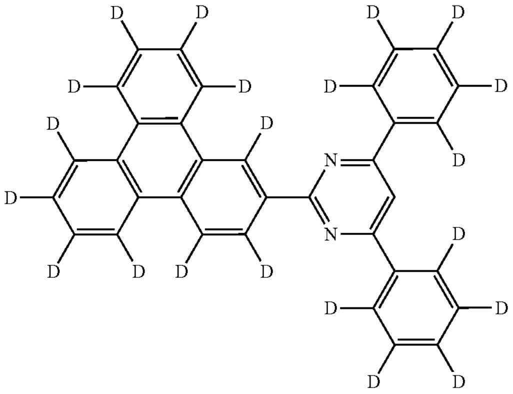
-continued
[A-13]
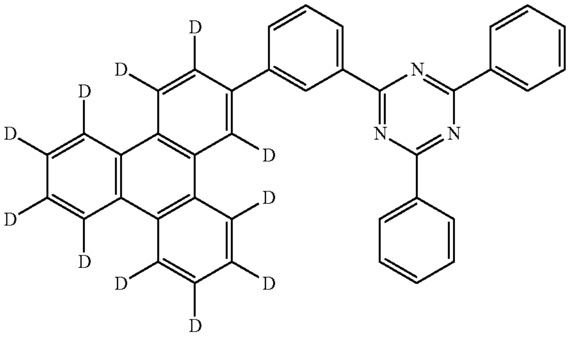
[A-14]
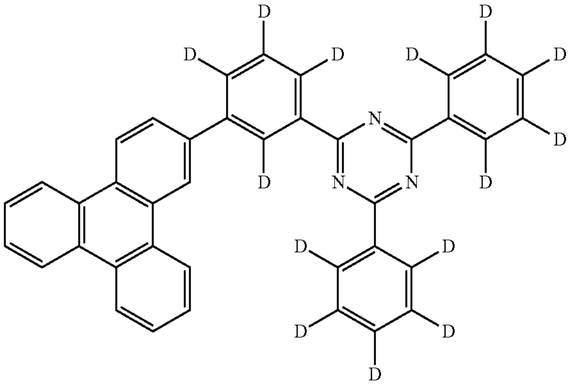
[A-15]
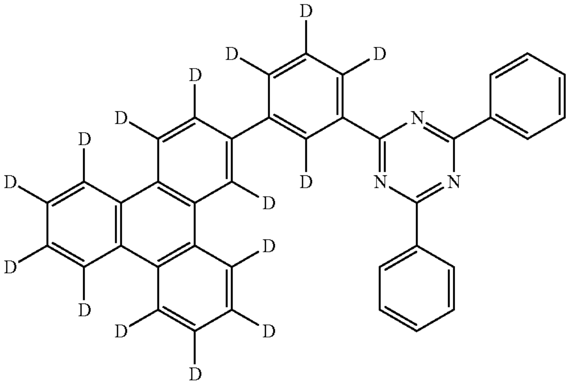
[A-16]
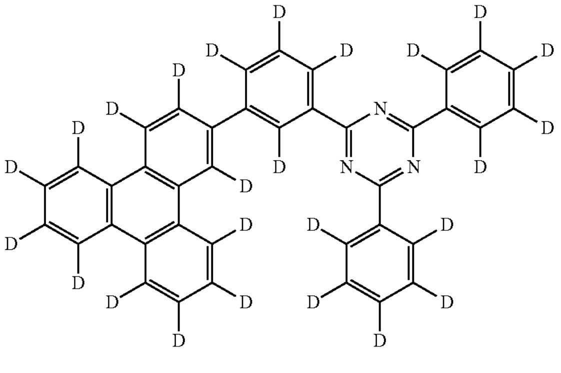

-continued
[A-17]
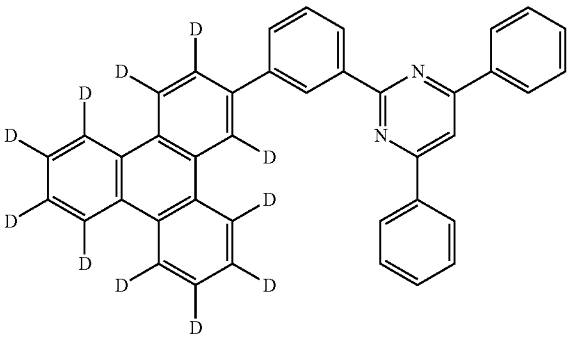
[A-18]
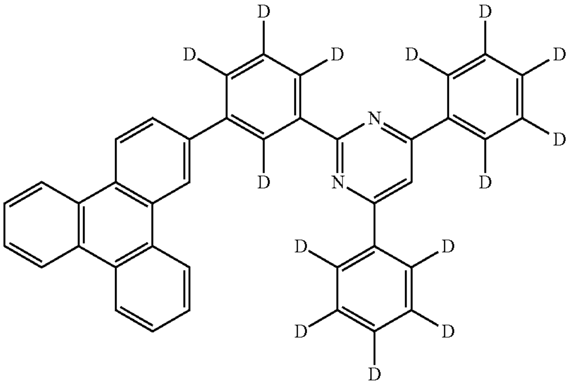
[A-19]
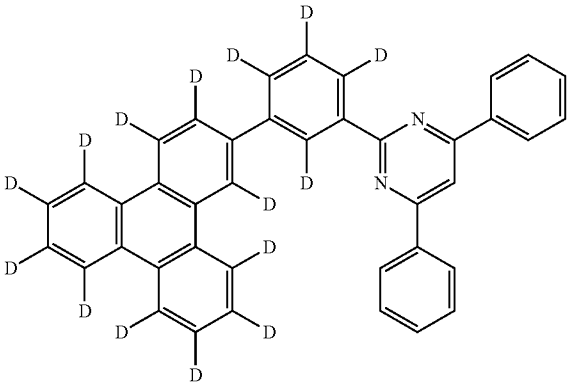
[A-20]
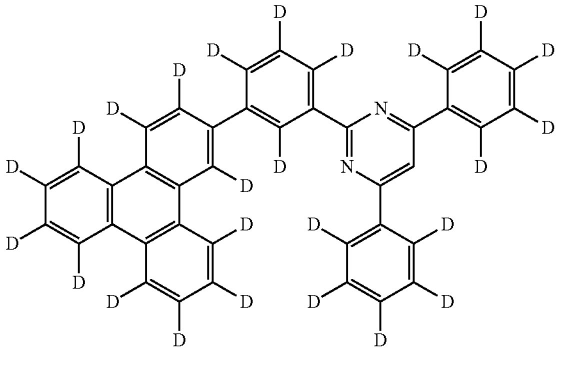
-continued
[A-21]
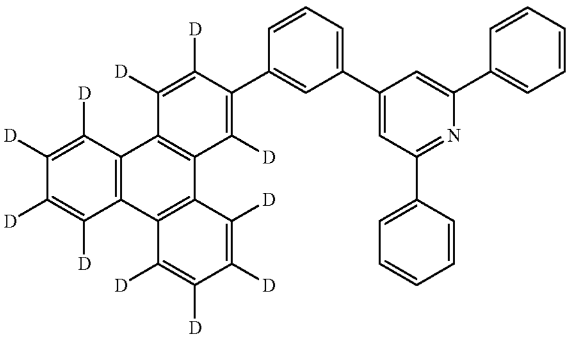
[A-22]
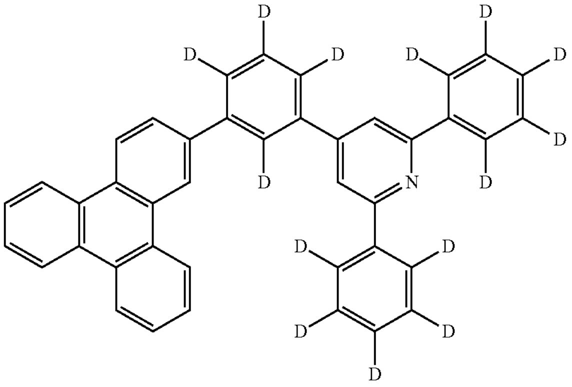
[A-23]
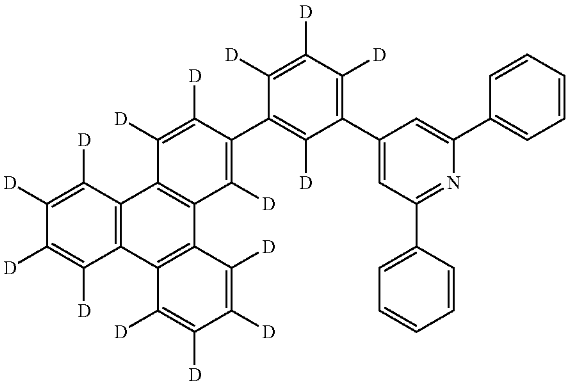
[A-24]
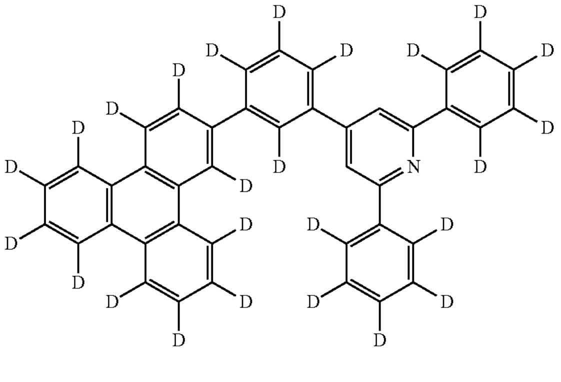

-continued
[A-25]
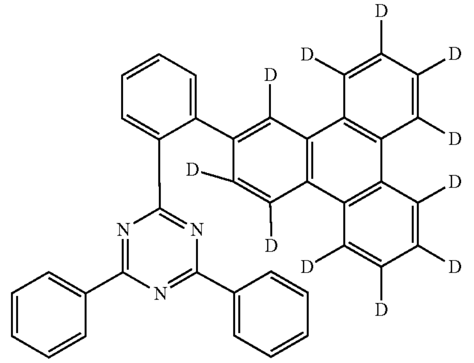
[A-26]
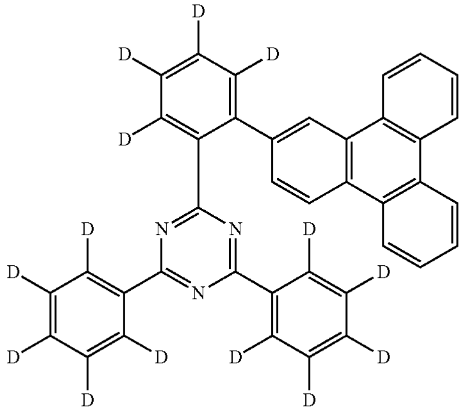
[A-27]
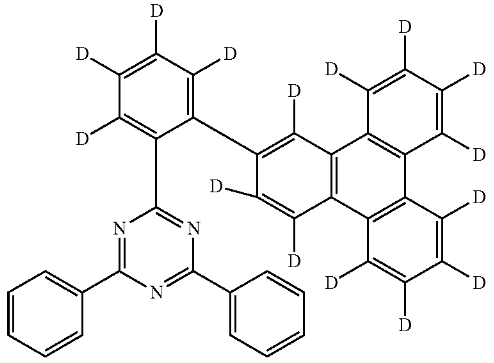
[A-28]
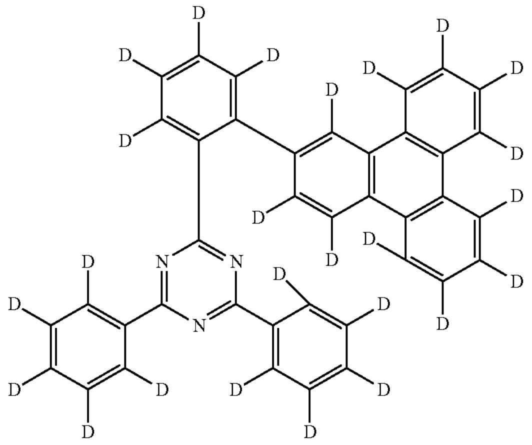
-continued
[A-29]
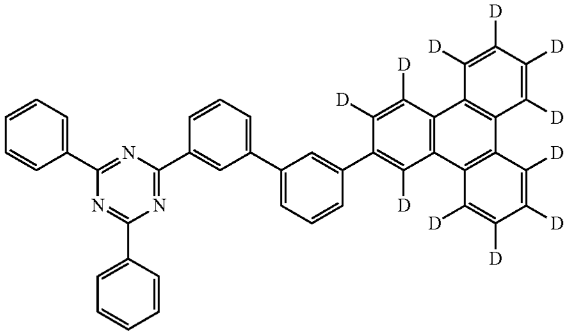
[A-30]
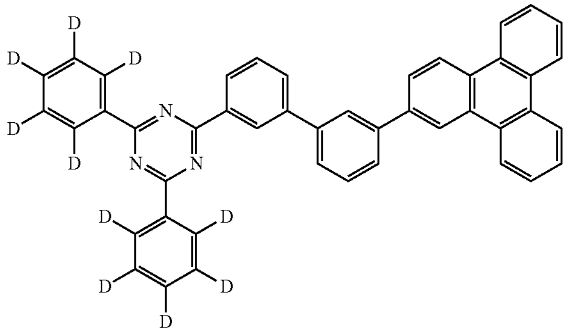
[A-31]
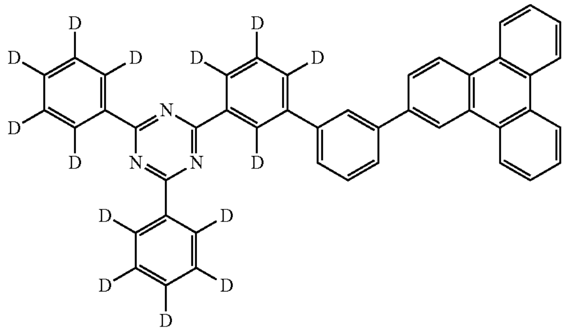
[A-32]
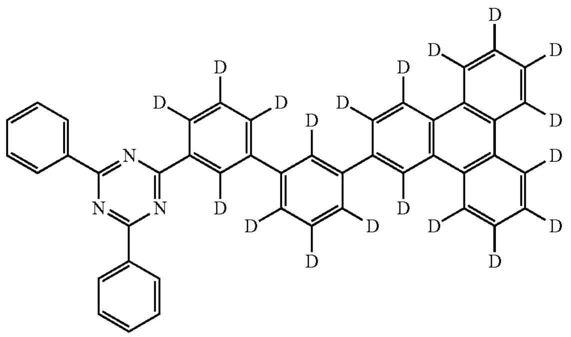

-continued
[A-33]
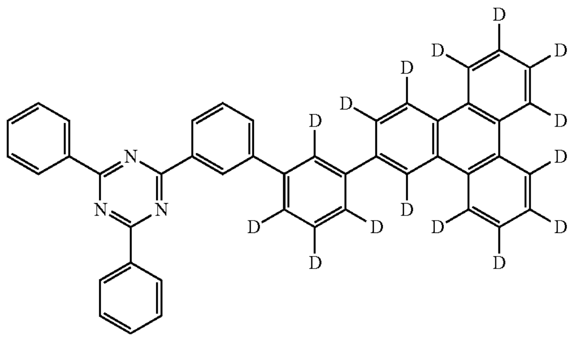
[A-34]
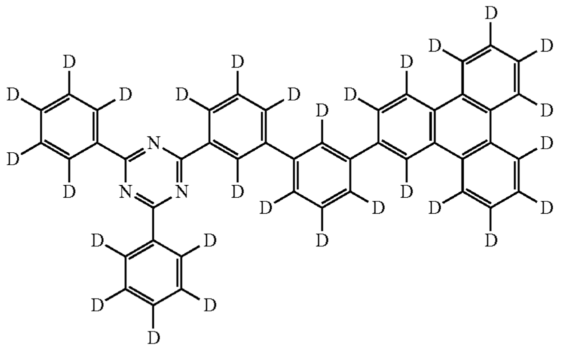
[A-35]
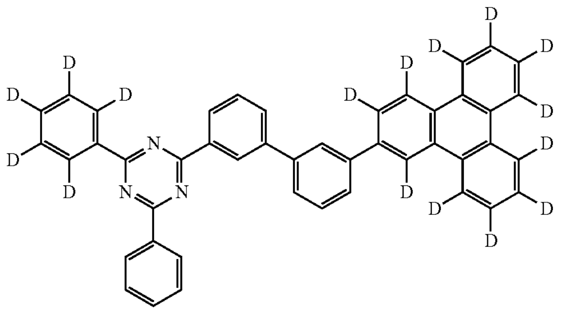
[A-36]
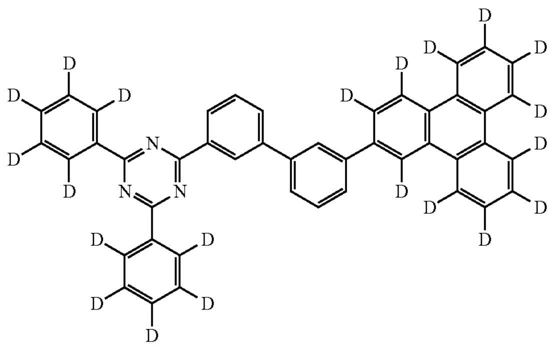
-continued
[A-37]
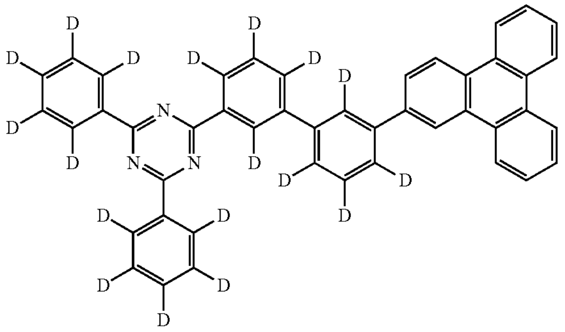
[A-38]
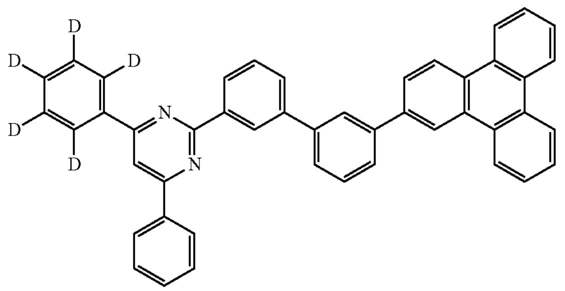
[A-39]
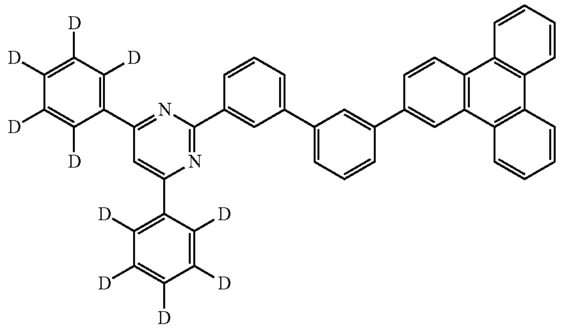
[A-40]
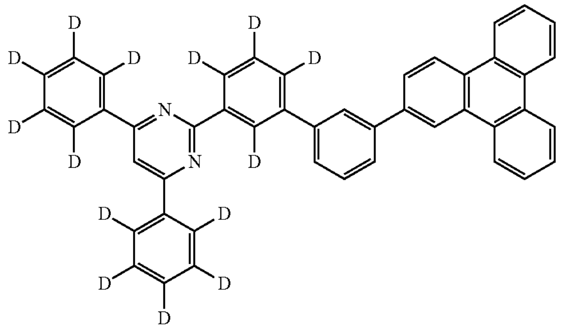

-continued
[A-41]
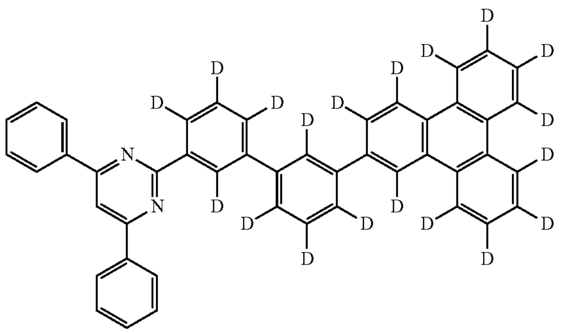
[A-42]
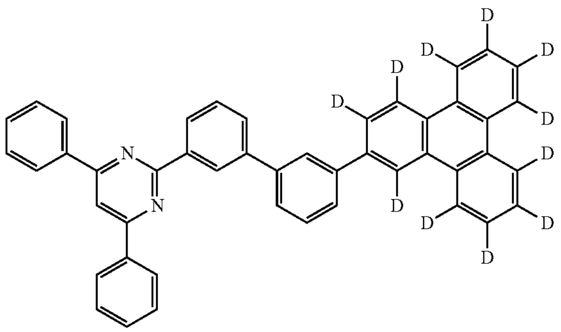
[A-43]
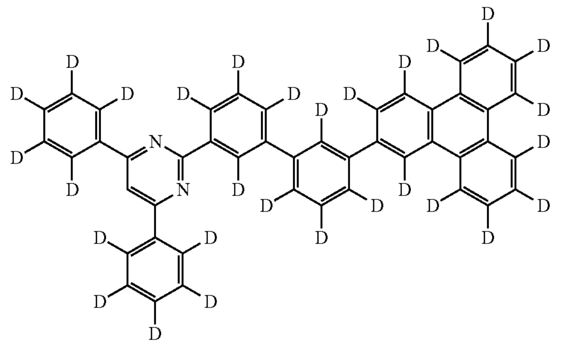
[A-44]
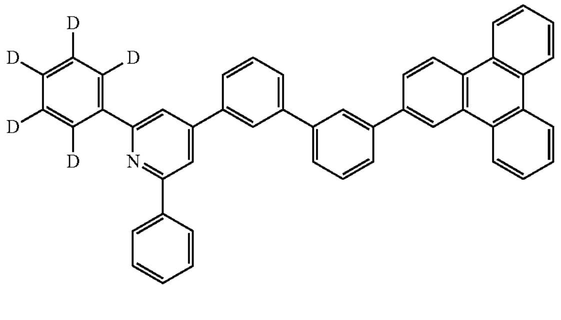
-continued
[A-45]
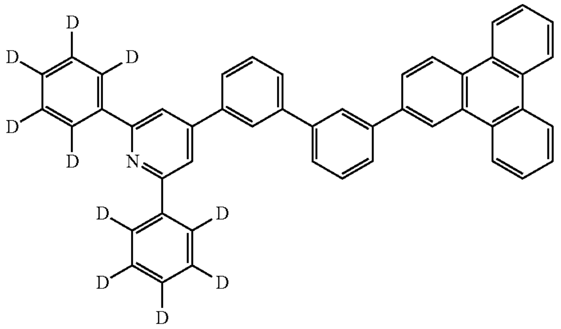
[A-46]
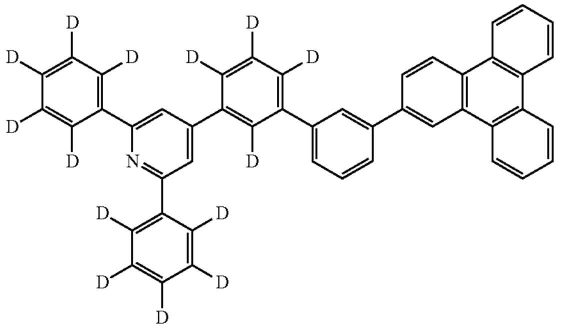
[A-47]
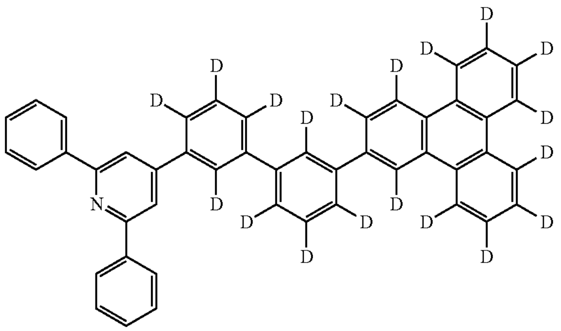
[A-48]
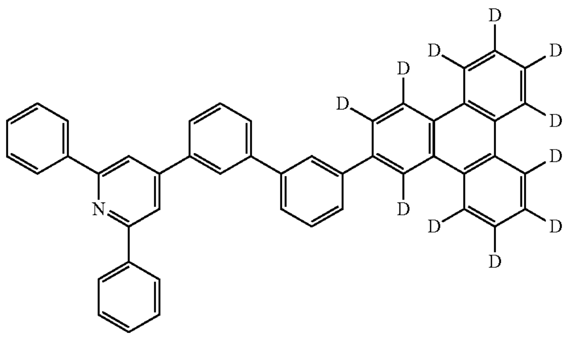

-continued
[A-49]
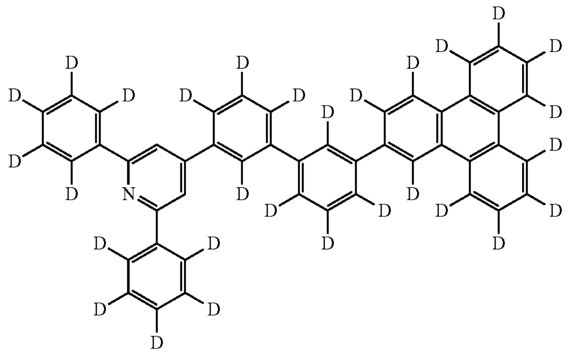
[A-50]
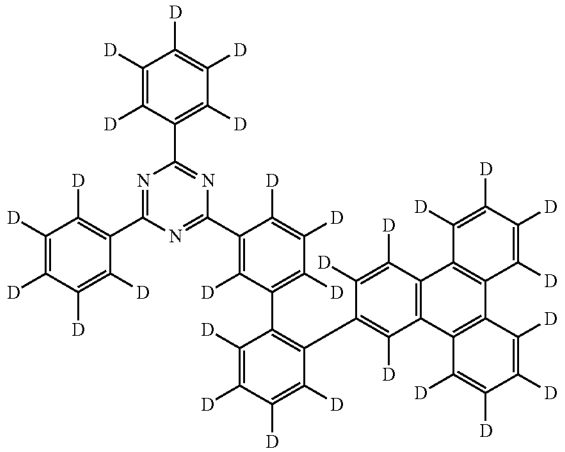
[A-51]
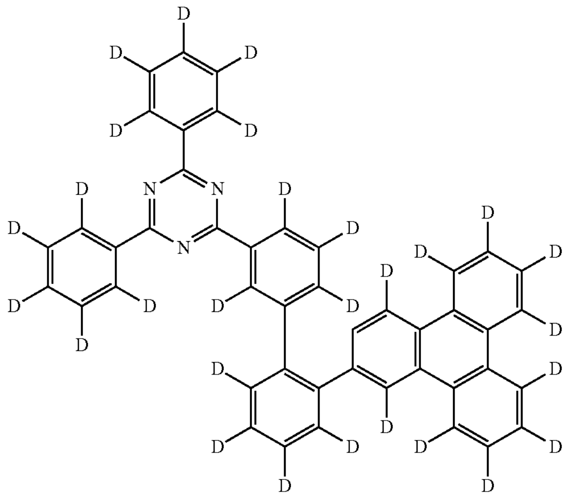
-continued
[A-52]
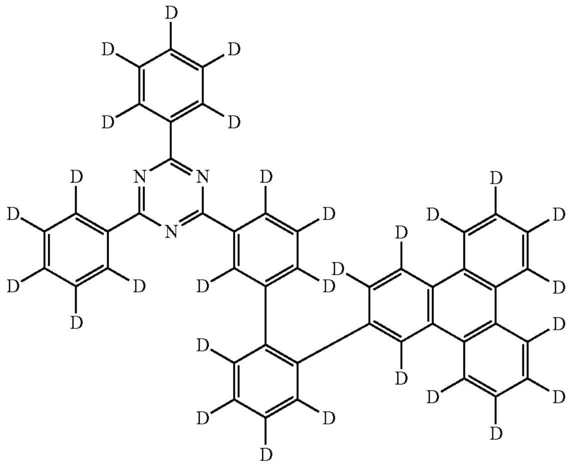
[A-53]
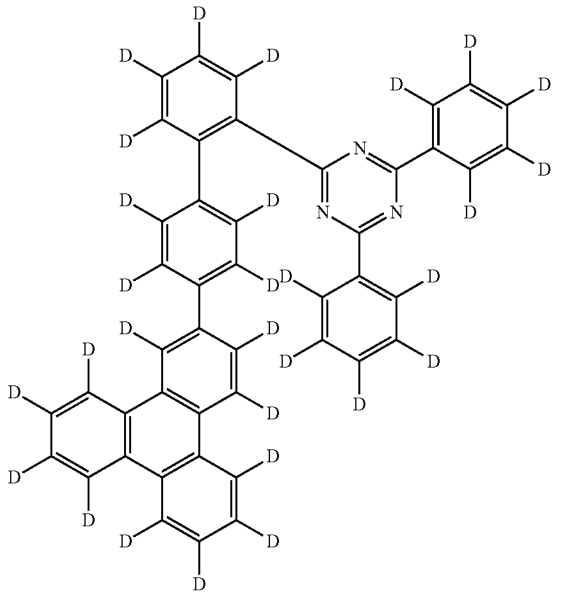
[A-54]
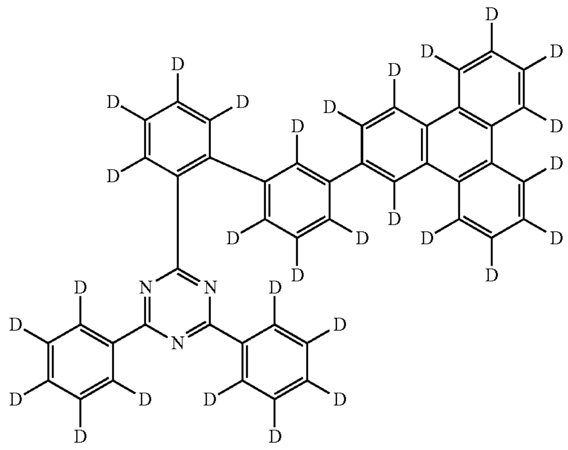

-continued
[A-55]
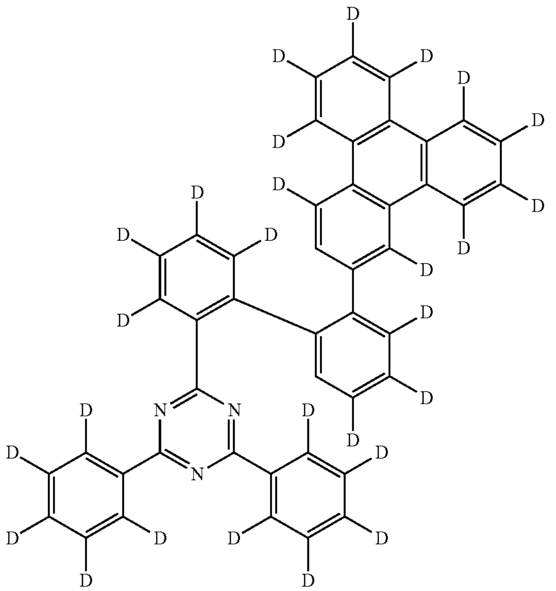
[A-56]
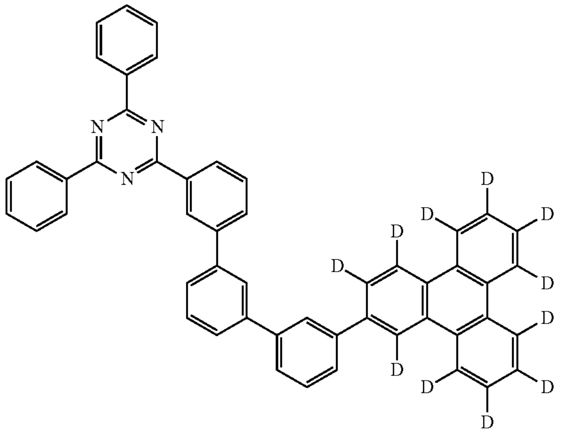
[A-57]
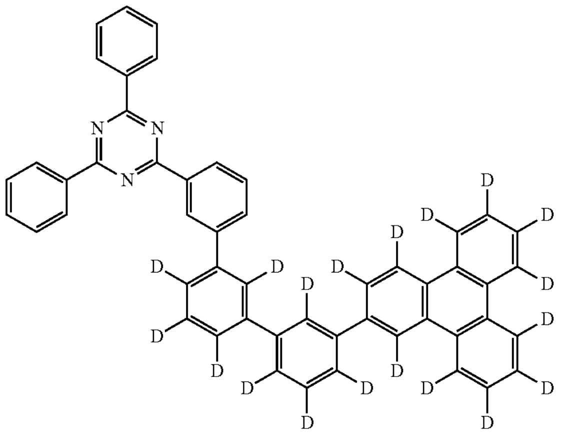
-continued
[A-58]
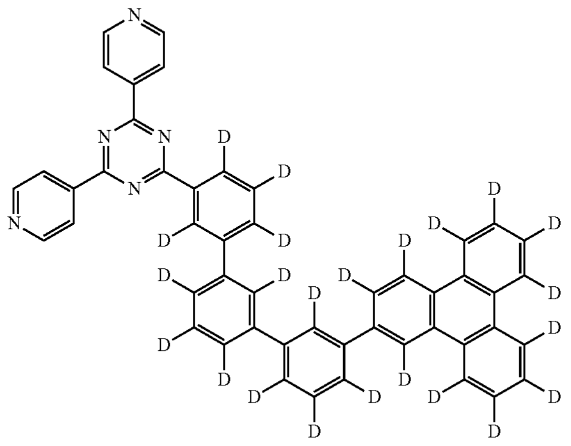
[A-59]
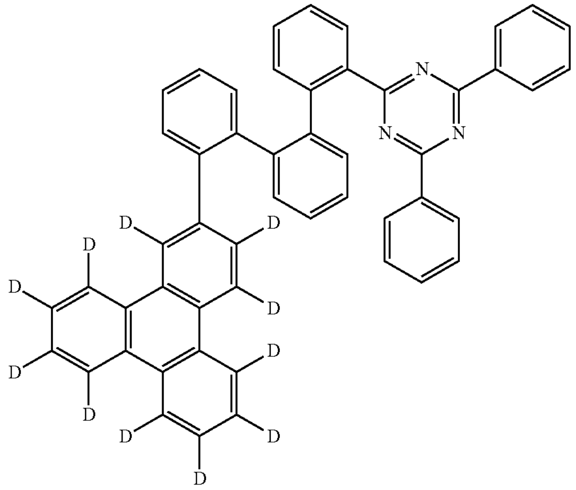
[A-60]
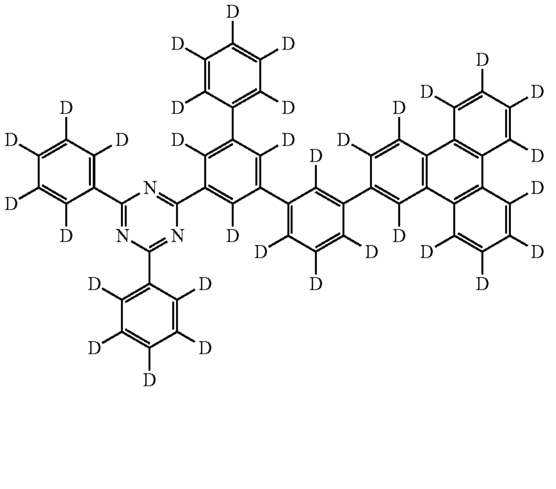

-continued
[A-61]
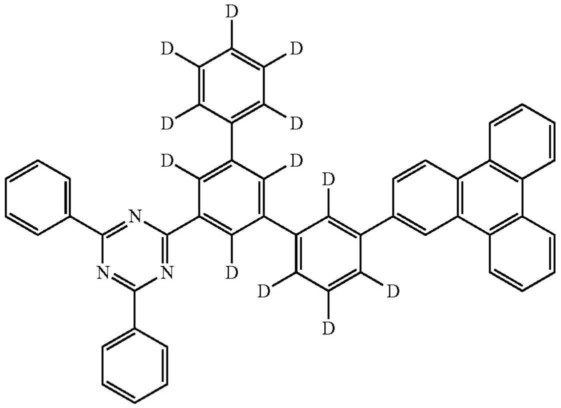
[A-62]
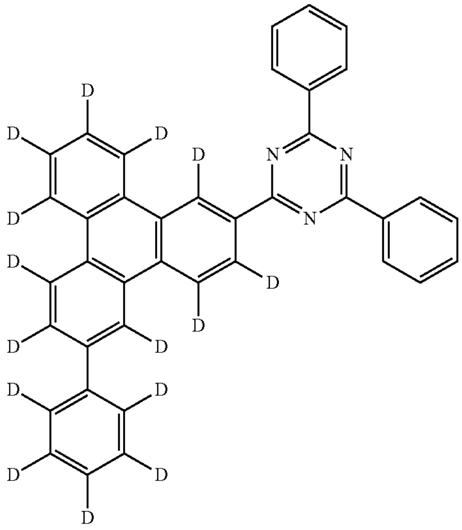
[A-63]
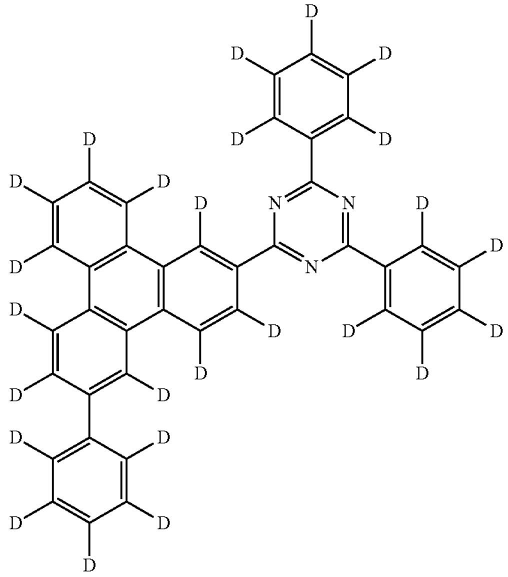
-continued
[A-64]
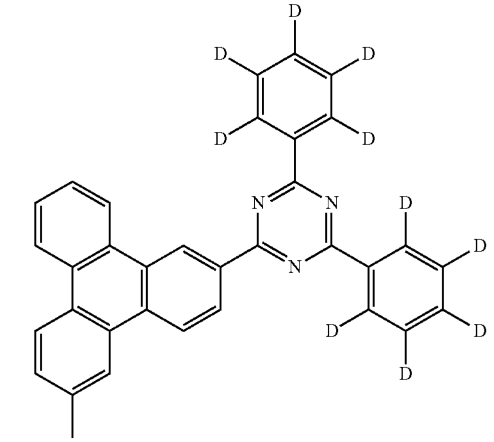
[A-65]
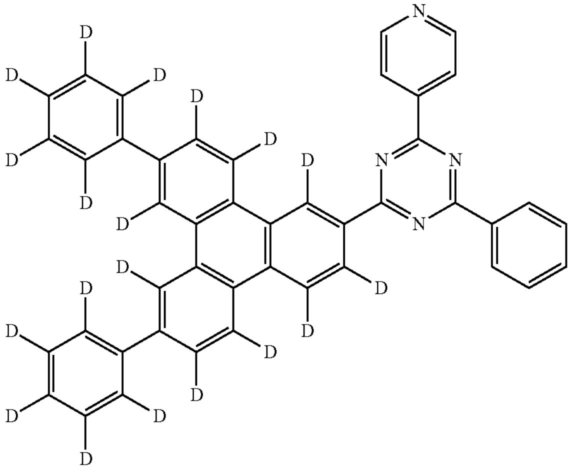
[A-66]
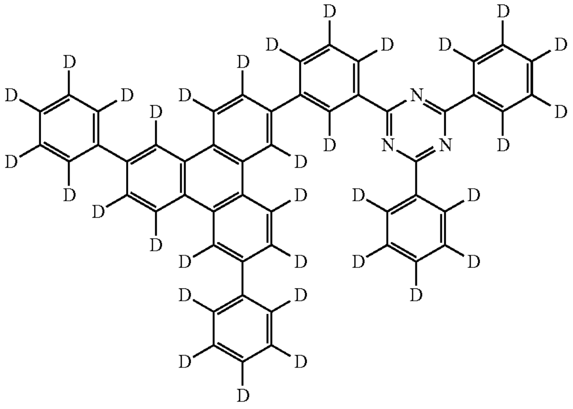

-continued

[A-67]

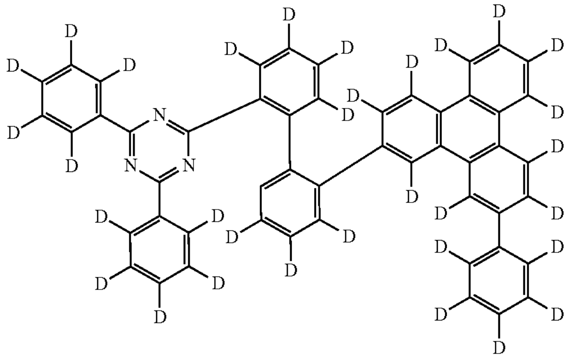

[A-68]

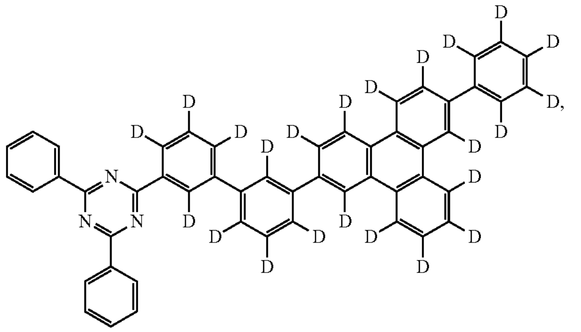

[Chemical Formula 2-I]

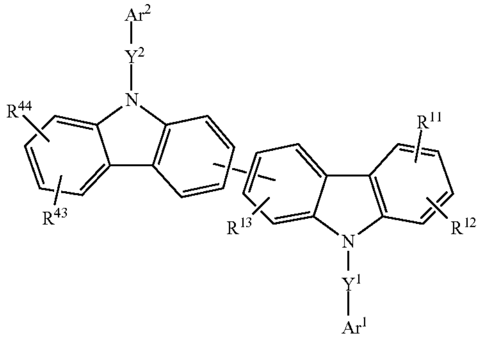

wherein $Y^1$ and $Y^2$ of Chemical Formula 2-I are independently a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof, wherein the heteroarylene group of $Y^1$ and $Y^2$ of Chemical Formula 2-I is an arylene group that has 1 to 3 hetero atoms selected from the group consisting of O, S, P, and Si in an aromatic ring thereof, wherein $Ar^1$ and $Ar^2$ of Chemical Formula 2-I are independently a substituted or unsubstituted C6 to C30 aryl group, a substituted or unsubstituted C2 to C30 heteroaryl group, or a combination thereof, wherein "substituted" for $Ar^1$ and $Ar^2$ of Chemical Formula 2-I refers to replacement of a hydrogen with a deuterium, a halogen, a hydroxy group, an amino group, a C1 to C30 amine group, a nitro group, a C1 to C40 silyl group, a C1 to C30 alkyl group, a C1 to C10 alkylsilyl group, a C3 to C30 cycloalkyl group, a C3 to C30 heterocycloalkyl group, a C6 to C30 aryl group, a C1 to C20 alkoxy group, a fluoro group, a C1 to C10 trifluoroalkyl group, or a cyano group, wherein the heteroaryl group of $Ar^1$ and $Ar^2$ of Chemical Formula 2-I is an aryl group that has 1 to 3 hetero atoms selected from the group consisting of O, S, P, and Si in an aromatic ring thereof, wherein moieties $—Y^1—Ar^1$ and $—Y^2—Ar^2$ of Chemical Formula 2-I do not include any of a dibenzofuranyl group, a dibenzothiopheneyl group, a benzofuranyl group, or a benzothiophenyl group, and wherein $R^{11}$ to $R^{13}$ and $R^{43}$ to $R^{44}$ of Chemical Formula 2-I are independently hydrogen, deuterium, a substituted or unsubstituted C1 to C20 alkyl group, a substituted or unsubstituted C6 to C50 aryl group, a substituted or unsubstituted C2 to C50 heteroaryl group, or a combination thereof.

2. The composition as claimed in claim 1, wherein at least one of Y, $Y^2$, $Ar^1$, $Ar^2$, $R^{11}$ to $R^{13}$, $R^{43}$ and $R^{44}$ of Chemical Formula 2-I comprises at least one deuterium.

3. The composition as claimed in claim 1, wherein the first compound is selected from the compounds listed in the following Group 1A:

[Group 1A]

[A-5]

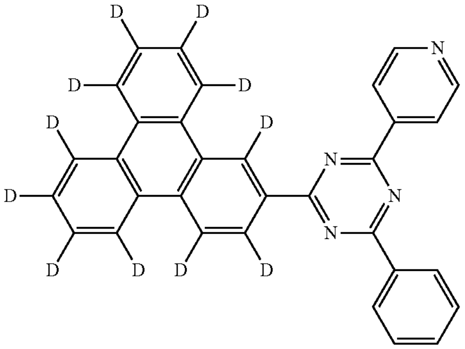

[A-6]

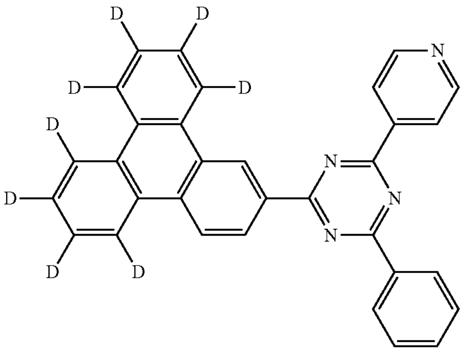

-continued

[A-7]

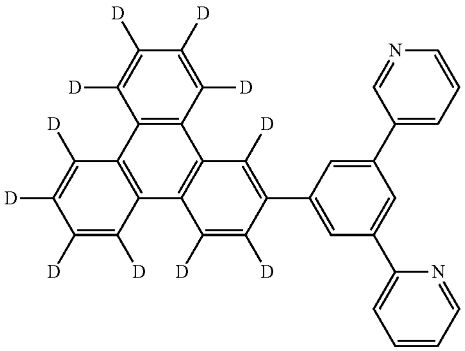

[A-8]

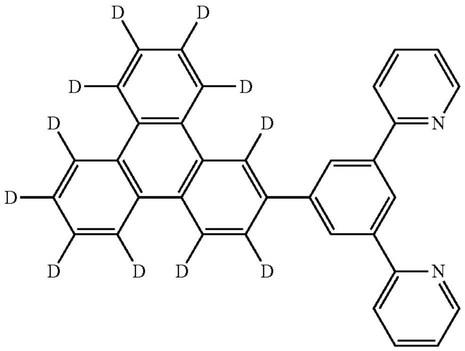

[A-58]

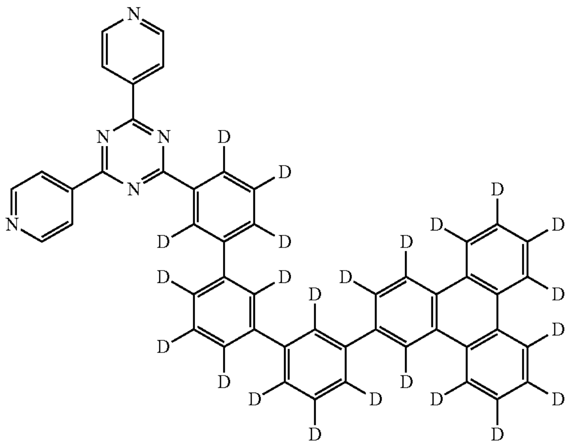

-continued

[A-65]

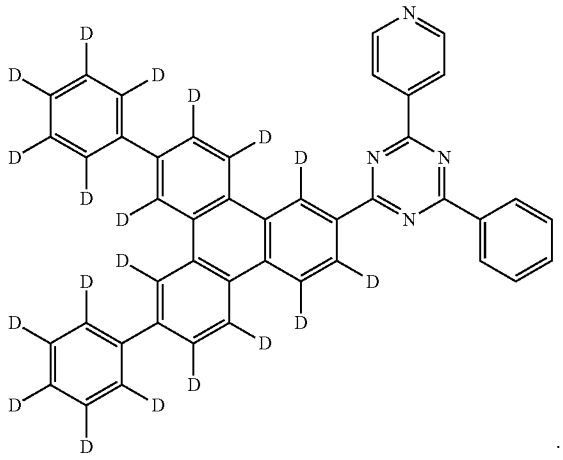

4. An organic optoelectronic device, comprising:

an anode and a cathode facing each other, and at least one organic layer between the anode and the cathode, wherein the at least one organic layer includes the composition as claimed in claim 1.

5. The organic optoelectronic device as claimed in claim 4, wherein:

the at least one organic layer includes a light emitting layer, and the light emitting layer includes the composition.

6. A display device comprising the organic optoelectronic device as claimed in claim 4.

* * * * *